(12) United States Patent
Liu et al.

(10) Patent No.: US 10,421,993 B2
(45) Date of Patent: *Sep. 24, 2019

(54) METHODS AND COMPOSITIONS FOR REDUCING NON-SPECIFIC AMPLIFICATION PRODUCTS

(71) Applicant: Paragon Genomics, Inc., Hayward, CA (US)

(72) Inventors: Zhitong Liu, Foster City, CA (US); Jeffrey Juehui Liu, Foster City, CA (US); Guoying Liu, San Ramon, CA (US); Tao Chen, San Francisco, CA (US)

(73) Assignee: Paragon Genomics, Inc., Hayward, CA (US)

( * ) Notice: Subject to any disclaimer, the term of this patent is extended or adjusted under 35 U.S.C. 154(b) by 277 days.

This patent is subject to a terminal disclaimer.

(21) Appl. No.: 15/290,981

(22) Filed: Oct. 11, 2016

(65) Prior Publication Data

US 2017/0022551 A1    Jan. 26, 2017

Related U.S. Application Data

(63) Continuation-in-part of application No. 15/041,644, filed on Feb. 11, 2016, now Pat. No. 9,464,318.

(60) Provisional application No. 62/114,788, filed on Feb. 11, 2015, provisional application No. 62/150,600, filed on Apr. 21, 2015.

(51) Int. Cl.
  *C12Q 1/68*   (2018.01)
  *C12Q 1/6848* (2018.01)
  *C12Q 1/6806* (2018.01)

(52) U.S. Cl.
  CPC ......... *C12Q 1/6848* (2013.01); *C12Q 1/6806* (2013.01)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,965,188 A | 10/1990 | Mullis et al. |

(Continued)

FOREIGN PATENT DOCUMENTS

| WO | WO2005/095605 A1 | 10/2005 |
| WO | WO2006/127423 A2 | 11/2006 |

(Continued)

OTHER PUBLICATIONS

Babon et al.; The use of resolvases T4 endonuclease VII and T7 endonuclease I in mutation detection; From Methods in Molecular Biology; vol. 152: DNA Repair Protocols: Prokaryotic systems; Edited by P. Vaughan; © Humana Press Inc.; Totowa, NJ; pp. 187-199; Jul. 2000.

(Continued)

*Primary Examiner* — Samuel C Woolwine
(74) *Attorney, Agent, or Firm* — Shay Glenn LLP

(57) ABSTRACT

Methods, compositions, systems and kits to amplify or improve amplification of target-specific amplification products by reducing non-specific amplification products (e.g., primer-dimers) when amplifying multiple different nucleotide regions. The methods, compositions, systems and kits described herein may include, or include the use of, one or more resolvases that recognize and bind to and/or cut an aberrant DNA structure.

20 Claims, 26 Drawing Sheets

Specification includes a Sequence Listing.

(56) References Cited

U.S. PATENT DOCUMENTS

| | | | |
|---|---|---|---|
| 5,168,038 | A | 12/1992 | Tecott et al. |
| 5,210,015 | A | 5/1993 | Gelfand et al. |
| 5,399,491 | A | 3/1995 | Kacian et al. |
| 5,539,082 | A | 7/1996 | Nielsen et al. |
| 5,750,341 | A | 5/1998 | Macevicz |
| 5,854,033 | A | 12/1998 | Lizardi |
| 5,925,517 | A | 7/1999 | Tyagi et al. |
| 6,174,670 | B1 | 1/2001 | Wittwer et al. |
| 6,670,461 | B1 | 12/2003 | Wengel et al. |
| 8,586,310 | B2 | 11/2013 | Mitra et al. |
| 8,673,560 | B2 | 3/2014 | Leamon et al. |
| 8,685,678 | B2 | 4/2014 | Casbon et al. |
| 9,464,318 | B2 | 10/2016 | Liu |
| 9,752,188 | B2 | 9/2017 | Schmitt et al. |
| 2004/0185484 | A1 | 9/2004 | Costa et al. |
| 2008/0014634 | A1 | 1/2008 | Greener et al. |
| 2009/0123913 | A1 | 5/2009 | Barany et al. |
| 2013/0261027 | A1 | 10/2013 | Li et al. |
| 2014/0227705 | A1 | 8/2014 | Vogelstein et al. |
| 2014/0329245 | A1 | 11/2014 | Spier et al. |
| 2014/0378317 | A1 | 12/2014 | Fu et al. |

FOREIGN PATENT DOCUMENTS

| | | |
|---|---|---|
| WO | WO2012/149438 A1 | 11/2012 |
| WO | WO2015/063154 A1 | 5/2015 |

OTHER PUBLICATIONS

Lowell et al.; Heteroduplex resolution using T7 endonuclease I in microbial community analyses; Bio Techniques; 28(4); pp. 676-681; Apr. 2000.

Takishita et al.; Genetic diversity of microbial eukaryotes in anoxic sediment of the saline meromictic lake namako-ike (japan): on the detection of anaerobic or anoxic-tolerant lineages of eukaryotes; Protist; 158(1); pp. 51-64; Jan. 2007.

Chen et al.; Generation and analysis of a barcode-tagged insertion mutant library in the fission yeast schizosaccharomyces pombe; BMC Genomics; 13(1); 18 pages; retrieved from the internet (http://www.biomedcentral.com/1471-2164/13/161; Dec. 2012.

Fuhrmann et al.; Removal of mismatched bases from synthetic genes by enzymatic mismatch cleavage; Nucleic Acids Research; 33(6); 8 pages; doi:10.1093/nar/gni058; Jan. 2005.

Allawi et al.; Thermodynamics and NMR of internal GO T mismatches in DNA; Biochemistry; 36(340; pp. 10581-10594; Aug. 1997.

Bernard et al.; Color multiplexing hybridization probes using the apolipoprotein E locus as a model system for genotyping; Anal. Biochem.; 273(2); pp. 221-228; Sep. 10, 1999.

Casbon et al.; A method for counting PCR template molecules with application to next-generation sequencing; Nucleic Acids Res.; 39(12); 8 pages; e81.doi: 10.1093/nar/gkr217; Jul. 2011.

Crooke et al.; Section review biologicals and immunologicals: Progress in the development and patenting of antisense drug discovery technology; Expert Opinion on Therapeutic Patents; 6(9); pp. 855-870; Sep. 1, 1996.

Fu et al.; Counting individual DNA molecules by the stochastic attachment of diverse labels; Proc. Natl. Acad. Sci. USA; 108(22); pp. 9026-9031; May 31, 2011.

Gregory et al.; Targeted single molecule mutation detection with massively parallel sequencing; Nucleic Acids Res.; 44(3); 11 pages; e22. doi:10.1093/nar/gkv915; Feb. 18, 2016.

Hoffmann et al.; DNA bar coding and pyrosequencing to identify rare HIV drug resistance mutations; Nucleic Acids Res.; 35(13); 8pages; e91, doi:10.1093/nar/gkm435; ; Jun. 18, 2007.

Kanehisa ; Use of statistical criteria for screening potential homologies in nucleic acid sequences; Nucleic Acids Res.; 12(1 prt 1); pp. 203-213; Jan. 11, 1984.

Kivioja et al.; Counting absolute numbers of molecules using unique molecular identifiers; Nat. Methods; 9(1); pp. 72-74; (Author Manuscript); Nov. 20, 2011.

Leone et al; Molecular beacon probes combined with amplification by NASBA enable homogeneous, real-time detection of RNA; Nucleic Acids Res.; 26(9); pp. 2150-2155; May 1, 1998.

Mackay et al.; Real-time PCR in virology; Nucleic Acids Research; 30(6); pp. 1292-1305; Mar. 15, 2002.

Mardis; The impact of next-generation sequencing technology on genetics; Treand in Genetics; 24(3); pp. 133-141; Mar. 1, 2008.

Mesmaeker et al.; Backbone modifications in oligonucleotides and peptide nucleic acid systems; Current Opinion in Structural Biology; 5(3); pp. 343-355; Jun. 1995.

Newman et al.; Integrated digital error suppression for imptoved detection of circulating tumor DNA; Nature Biotechnology; 34(5); pp. 547-555, doi:10.1038/nbt.3520; (Author Manuscript); May 2016.

Schmitt et al.; Detection of ultra-rare mutations by next-generation sequencing; Proc. Natl. Acad. Sci. USA; 109(36); pp. 14508-14513; Sep. 4, 2012.

Shendure et al.; Next-generation DNA sequencing; Nature Biotechnology; 26(10); pp. 1135-1145; Oct. 2008.

Stahlberg et al.; Simple, multiplexed, PCR-based barcoding of DNA enables sensitive mutation detection in liquid biopsies using sequencing; Nucleic Acids Res.; 44(11); pp. 1-7; e105. doi: 10.1093/nar/gkw224; Jun. 20, 2016.

Su et al.; Next-generation sequencing and its applications in molecular diagnostics; Expert Rev. Mol. Diagn.; 11(3); pp. 333-343; Apr. 2011.

Uhlman et al.; Antisense oligonucleotides: a new therapeutic principle; Chemical Reviews; 90(4); pp. 543-584; Jun. 1, 1990.

Wang et al.; Targeted sequencing of both DNA strands barcoded and captured individually by RNA probes to identify genome-wide ultra-rare mutations; Scientific Reports; 7(1); 14 pages; 3356 DOI:10.1038/s41598-017-03448-8; Jun. 13, 2017.

Young et al.; Efficient isolation of genes by using antibody probes; Proc. Natl. Acad. Sci.USA; 80(5); pp. 1194-1198; Mar. 1983.

Zhang et al.; The impact of next-generation sequencing on genomics; J. Genet. Genomics; 38(3); pp. 95-109; (Author Manuscript) Mar. 20, 2011.

Liu et al.; U.S. Appl. No. 15/867,031 entitled "Methods and compositions for reducing redundant molecular barcodes created in primer extension reactions," filed Jan. 10, 2018.

| QC specifications | 207 plex |
|---|---|
| GENOME_SIZE | 3095693983 |
| TARGET_TERRITORY | 22027 |
| TOTAL_READS | 1775168 |
| PF_READS | 1775168 |
| PF_BASES | 259075294 |
| PF_UNIQUE_READS | 1775168 |
| PCT_PF_READS | 1 |
| PCT_PF_UQ_READS | 1 |
| PF_UQ_READS_ALIGNED | 1765598 |
| PF_SELECTED_PAIRS | 841003 |
| PF_SELECTED_UNIQUE_PAIRS | 841003 |
| PCT_PF_UQ_READS_ALIGNED | 99.46% |
| PF_UQ_BASES_ALIGNED | 256516961 |
| ON_AMPLICON_BASES | 244963005 |
| NEAR_AMPLICON_BASES | 351058 |
| OFF_AMPLICON_BASES | 11202898 |
| ON_TARGET_BASES | 180783975 |
| ON_TARGET_FROM_PAIR_BASES | 180228719 |
| PCT_AMPLIFIED_BASES | 95.63% |
| PCT_OFF_AMPLICON | 4.37% |
| ON_AMPLICON_VS_SELECTED | 99.86% |
| MEAN_AMPLICON_COVERAGE | 7688 |
| MEAN_TARGET_COVERAGE | 8207 |
| FOLD_ENRICHMENT | 92777 |
| ZERO_CVG_TARGETS_PCT | 0 |
| FOLD_80_BASE_PENALTY | 1.6709 |
| PCT_TARGET_BASES_2X | 100.00% |
| PCT_TARGET_BASES_10X | 100.00% |
| PCT_TARGET_BASES_20X | 100.00% |
| PCT_TARGET_BASES_30X | 100.00% |
| PCT_TARGET_BASES_40X | 100.00% |
| PCT_TARGET_BASES_50X | 100.00% |
| PCT_TARGET_BASES_100X | 99.97% |
| AT_DROPOUT | 3.51 |
| GC_DROPOUT | 5.57 |
| Percent amplicon at >=20% of mean | 98.55% |

FIG. 22

| QC specifications | 207 plex long primers |
|---|---|
| GENOME_SIZE | 3095693983 |
| TARGET_TERRITORY | 22027 |
| TOTAL_READS | 1973434 |
| PF_READS | 1973434 |
| PF_BASES | 286209162 |
| PF_UNIQUE_READS | 1973434 |
| PCT_PF_READS | 1 |
| PCT_PF_UQ_READS | 1 |
| PF_UQ_READS_ALIGNED | 1966028 |
| PF_SELECTED_PAIRS | 971600 |
| PF_SELECTED_UNIQUE_PAIRS | 971600 |
| PCT_PF_UQ_READS_ALIGNED | 99.62% |
| PF_UQ_BASES_ALIGNED | 284260202 |
| ON_AMPLICON_BASES | 281224635 |
| NEAR_AMPLICON_BASES | 26889 |
| OFF_AMPLICON_BASES | 3008678 |
| ON_TARGET_BASES | 206078511 |
| ON_TARGET_FROM_PAIR_BASES | 205803244 |
| PCT_AMPLIFIED_BASES | 98.94% |
| PCT_OFF_AMPLICON | 1.06% |
| ON_AMPLICON_VS_SELECTED | 99.99% |
| MEAN_AMPLICON_COVERAGE | 8826 |
| MEAN_TARGET_COVERAGE | 9356 |
| FOLD_ENRICHMENT | 96116 |
| ZERO_CVG_TARGETS_PCT | 0 |
| FOLD_80_BASE_PENALTY | 1.4993 |
| PCT_TARGET_BASES_2X | 100.00% |
| PCT_TARGET_BASES_10X | 100.00% |
| PCT_TARGET_BASES_20X | 100.00% |
| PCT_TARGET_BASES_30X | 99.97% |
| PCT_TARGET_BASES_40X | 99.97% |
| PCT_TARGET_BASES_50X | 99.97% |
| PCT_TARGET_BASES_100X | 99.38% |
| AT_DROPOUT | 3.6731 |
| GC_DROPOUT | 4.6105 |
| Percent amplicon at >=20% of mean | 97.52% |

FIG. 23

| QC specifications | 4000 plex |
|---|---|
| GENOME_SIZE | 3095693983 |
| AMPLICON_TERRITORY | 1688650 |
| TARGET_TERRITORY | 1688650 |
| TOTAL_READS | 6113730 |
| PF_READS | |
| PF_BASES | 6113730 |
| PF_UNIQUE_READS | 6113730 |
| PCT_PF_READS | 100% |
| PCT_PF_UQ_READS | 100% |
| PF_UQ_READS_ALIGNED | |
| PF_SELECTED_PAIRS | |
| PF_SELECTED_UNIQUE_PAIRS | 6002474 |
| PCT_PF_UQ_READS_ALIGNED | 98.18% |
| PF_UQ_BASES_ALIGNED | 890189928 |
| ON_AMPLICON_BASES | 792305883 |
| NEAR_AMPLICON_BASES | 92483794 |
| OFF_AMPLICON_BASES | 5400251 |
| ON_TARGET_BASES | 792305883 |
| PCT_AMPLIFIED_BASES | 99.39% |
| PCT_OFF_AMPLICON | 0.61% |
| ON_AMPLICON_VS_SELECTED | 89.55% |
| MEAN_AMPLICON_COVERAGE | 469 |
| MEAN_TARGET_COVERAGE | 470 |
| FOLD_ENRICHMENT | 1632 |
| ZERO_CVG_TARGETS_PCT | 0.15% |
| FOLD_80_BASE_PENALTY | 2.50 |
| PCT_TARGET_BASES_2X | 99.61% |
| PCT_TARGET_BASES_10X | 98.96% |
| PCT_TARGET_BASES_20X | 98.20% |
| PCT_TARGET_BASES_30X | 97.47% |
| AT_DROPOUT | 0.35 |
| GC_DROPOUT | 3.93 |
| Percent target at >=20% of mean | 95.20% |

FIG. 24

| ABL1 | ERBB2 | IDH1 | NOTCH1 | STK11 |
|------|-------|------|--------|-------|
| AKT1 | ERBB3 | IDH2 | NPM1 | TERT |
| ALK | ERBB4 | JAK2 | NRAS | TP53 |
| APC | EZH2 | JAK3 | PDGFRA | TSC1 |
| ATM | FBXW7 | KDR | PIK3CA | VHL |
| BRAF | FGFR1 | KIT | PIK3R1 | |
| BRCA1 | FGFR2 | KRAS | PTCH1 | |
| BRCA2 | FGFR3 | MAP2K1 | PTEN | |
| CDH1 | FLT3 | MET | PTPN11 | |
| CDKN2A | FOXL2 | MLH1 | RB1 | |
| CSF1R | GNA11 | MPL | RET | |
| CTNNB1 | GNAQ | MSH6 | SMAD4 | |
| DDR2 | GNAS | MTOR | SMARCB1 | |
| DNMT3A | HNF1A | NF1 | SMO | |
| EGFR | HRAS | NF2 | SRC | |

| Gene | Mutation | Expected Frequency | Observed Frequency | Standard Deviation |
|---|---|---|---|---|
| EGFR | p.E746_A750>VP | 5.0 | 5.8 | 1.0 |
| EGFR | p.L858R | 5.0 | 4.4 | 0.7 |
| EGFR | p.T790M | 5.0 | 4.6 | 1.0 |
| EGFR | p.V769-D770insASV | 5.0 | 4.3 | 1.2 |
| KRAS | p.G12D | 6.3 | 7.2 | 1.5 |
| NRAS | p.A59T | 6.3 | 5.5 | 1.0 |
| NRAS | p.Q61K | 6.3 | 6.4 | 1.2 |
| PIK3CA | p.E545K | 6.3 | 6.2 | 1.4 |

| Gene | Mutation | Expected Frequency | Observed Frequency | Standard Deviation |
|---|---|---|---|---|
| EGFR | p.E746_A750>VP | 1.0 | 1.3 | 0.4 |
| EGFR | p.L858R | 1.0 | 0.9 | 0.2 |
| EGFR | p.T790M | 1.0 | 1.2 | 0.7 |
| EGFR | p.V769-D770insASV | 1.0 | 0.7 | 0.2 |
| KRAS | p.G12D | 1.3 | 1.4 | 0.5 |
| NRAS | p.A59T | 1.3 | 1.4 | 0.5 |
| NRAS | p.Q61K | 1.3 | 1.4 | 0.5 |
| PIK3CA | p.E545K | 1.3 | 1.4 | 0.4 |

FIG. 32

METHODS AND COMPOSITIONS FOR REDUCING NON-SPECIFIC AMPLIFICATION PRODUCTS

CROSS REFERENCE TO RELATED APPLICATIONS

This patent application claims priority as a continuation-in-part of U.S. patent application Ser. No. 15/041,644, filed on Feb. 11, 2016, and titled "METHODS AND COMPOSITIONS FOR REDUCING NON-SPECIFIC AMPLIFICATION PRODUCTS", which claimed priority to U.S. provisional patent applications: U.S. Provisional Patent Application No. 62/114,788, filed on Feb. 11, 2015, and titled "A METHOD FOR ELIMINATING NONSPECIFIC AMPLIFICATION PRODUCTS IN MULTIPLEX PCR", and U.S. Provisional Patent Application No. 62/150,600, filed on Apr. 21, 2015, and titled "METHODS AND COMPOSITIONS FOR REDUCING NON-SPECIFIC AMPLIFICATION PRODUCTS". Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Feb. 14, 2019, is named 13982-700.500 SL.txt and is 3,636 bytes in size.

FIELD

The methods, compositions, systems and kits described herein relate to the amplification of nucleotide sequences. In particular, the methods, compositions, systems and kits described herein relate to the reduction of non-specific amplification products (e.g., primer-dimers) when amplifying multiple different nucleotide regions, such as during multiplex PCR including next generation sequencing (NGS).

BACKGROUND

In a uniplex PCR reaction (hereinafter referred to as uniplex PCR), the reaction typically contains template DNA, two primers flanking a single amplification site, a thermostable DNA polymerase, dNTPs and buffer. The resulting amplification products, the amplicons, are usually the target DNA fragment(s). The occasional non-specific amplification products are usually removed by fine-tuning PCR conditions, such as the annealing temperature, magnesium concentration, or through more stringent design of the primers.

Multiplex PCR refers to amplifying a plurality of target DNA fragments simultaneously in the same tube or well. This involves placing more than one pair of primers together. In practical applications, usually from tens to tens of thousands of different kinds of target DNA fragments are expected to be amplified simultaneously in a single tube. Multiplex PCR provides extraordinary simplicity, throughput, and economic advantages over uniplex PCR when different DNA fragments are needed to be amplified together in a single tube. It is also frequently used when dealing with precious samples (e.g., clinical samples).

Multiplex PCR already finds broad applications in detection and clinical diagnosis of genes and microorganisms in humans, animals, crops and plants, in species authentication, and more recently, in sample and library preparation for next generation sequencing (including, but not limited to, de novo sequencing and targeted re-sequencing). In gene testing and diagnosis, multiplex PCR is used in assays of single nucleotide polymorphisms (SNPs), genotyping, copy number variation, epigenetics, gene expression, and mutation and hybridization arrays.

Multiplex PCR typically requires placing together a large number of primers at certain concentrations in the same volume. These primers accumulate to very high quantity, for example up to micrograms, when a few thousand primers are used. A difficulty of multiplex PCR is that these primers can anneal with each other, leading to the generation of enormous amounts of non-specific amplification products. These non-specific amplification products usually make the target fragments undetectable, or simply cancel out the production of the target fragments.

Current techniques for making multiplex PCR workable despite the problem of these large amounts of primers and resulting background 'noise' may include specifically designing primers within very narrow parameter ranges, and/or incorporating exotic markers (e.g., U.S. Pat. Nos. 8,586,310 and 8,673,560, describe modification of primers by replacing thymidines with uredines so that the non-specific products are predominantly formed from non-specific annealing of primers that have multiple uridines interspersed along their length and can be specifically targeted on this basis), the use of oligonucleotides for preventing, or reducing, primer-dimer formation (see, e.g., WO2015063154 A1), and the use of tagged, target-specific primers that are blocked in combination with universal primers and a strategy for specifically activating blocked primers (see, e.g., US20140329245). All of these techniques have substantial drawbacks and limitations.

For example, methods for avoiding or reducing the formation of artifacts, such as primer-dimers, during nucleic acid amplification that center around the primer design process and often utilize dedicated software packages (e.g., DNAsoftwares's Visual OMP, MultiPLX, ABI's Primer Express, etc.) to design primer pairs that are predicted to exhibit minimal interaction between the other primers in the pool during amplification. Through the use of such software, primers can be designed to be as target-specific or amplicon-specific as possible, and often are grouped into subsets to minimize primer-primer interactions, primer-dimer formation and superamplicons. Stringent design parameters, however, limit the number of amplicons that can be co-amplified simultaneously and in some cases may prevent the amplification of some amplicons altogether. Other current methods require the use of multiple PCR primer pools to segregate primers into non-overlapping pools to minimize or prevent primer artifacts during the amplification step. Other methods include the use of multiple primer pools or single plex reactions to enhance the overall yield of amplification product per reaction.

In a multiplex PCR reaction, each primer pair competes in the amplification reaction with additional primer pairs for a finite amount of dNTPs, polymerase and other reagents. Primers may be designed to be longer than in uniplex PCR (24-35 bases), with higher melting temperatures (65° C. or higher) and a GC content of 50-60%, maintaining a similar melting temperature across all primers, and avoiding complementary sequences and runs of three or more Gs or Cs at the 3' end; the specificity of each pair of primers is first validated in uniplex PCR to ensure a single target fragment is amplified; the concentration of primer pairs are titrated, usually from 50 nM to 400 nM to ensure uniformity of the yield; primers are segregated into non-overlapping pools; optimal concentrations of dNTPS, magnesium and the thermostable DNA polymerase are determined, which are usually higher than in uniplex PCR; and salt concentration is also titrated to optimize the amplification specificity. With these parameters optimized, usually 2-5 target fragments are successfully simultaneously amplified. Through further computer-aided design of primers, methods of amplifying ~20 target fragments simultaneously in the same tube have been seen in the market. Due to the difficulty of mitigating or eliminating the non-specific products, only tens of targets are currently amplified in routine diagnostic practices. These methods require careful design of primers and PCR conditions, and fail to be used as standards for general diagnostic applications.

Numerous nested primers or similar strategies have been reported to extend the number of targets to be amplified in multiplex PCR. These methods may or may not always alleviate non-specific products generation. In addition, more primer layers, handling and cycling strategies are required in these methods. Therefore these methods find limited usage.

There is therefore a need for improved methods, compositions, systems, apparatuses and kits that allow for the selective amplification of multiple target nucleic acid molecules within a population of nucleic acid molecules while avoiding, or minimizing, the formation of artifacts (also referred to as non-specific amplification products), including primer dimers. There is also a need for improved methods, compositions, systems, apparatuses and kits that allow for the selective amplification of multiple target nucleic acid molecules from a single nucleic acid sample, such as genomic DNA and/or formalin-fixed paraffin embedded (FFPE) DNA while avoiding, or minimizing, the formation of artifacts. There is also a need in the art for improved methods, compositions, systems and kits that allow for the simultaneous amplification of thousands of target-specific nucleic acid molecules in a single reaction, which can be used in any applicable downstream assay or analysis. The methods, compositions, systems and kits described herein may address the problems and limitations discussed above.

SUMMARY OF THE DISCLOSURE

In general, described herein are methods, compositions, systems and kits for reducing non-specific amplification products from a template-dependent primer extension reaction. These methods, compositions, systems and kits may be useful in any reaction in which a plurality of primers may be used and may generate non-specific hybridization and/or amplification products, including so-called "primer dimers". For example, the methods, compositions, systems and kits described herein may be particularly well suited for use with multiplexed PCR and next generation sequencing.

The methods, compositions, systems and kits described herein arise from the novel and unexpected finding that resolvases, and particularly T4 endonuclease VII and/or T7 endonuclease I may be used to effectively and efficiently cleave non-specific amplification products, leaving the substantial proportion of target-specific amplification products in the same reaction mixture during or after amplification (e.g., multiplex amplification) in which an excess of a plurality of primer pairs (e.g., >6, >10, >100, >1000, >10, 000, etc.) are used. Without being bound by any particular theory of operation, the methods, compositions, systems and kits described herein are unexpectedly effective because they target aberrant sites (e.g., Holliday structures or junctions, branched DNAs, Y-structures, cruciforms, hetereoduplex loops, bulky adducts, single-stranded overhangs, DNA mismatches, or non-perfectly-matched DNAs). Such aberrant sites are a characteristic of the vast majority of non-specific amplification products in multiplex amplification and, surprisingly, by targeting these aberrant sites, a multiplexed amplification may be significantly cleaned while leaving a substantial percentage of target-specific amplification products intact.

For example, a method of reducing non-specific amplification products from a template-dependent primer extension reaction may include: amplifying a plurality of target nucleic acids using a plurality of pairs of target-specific primers wherein said amplifying generates a plurality of target-specific amplification products and a plurality of non-specific amplification products; introducing a resolvase that recognizes an aberrant DNA structure and cleaving said non-specific amplification products with the resolvase to generate a plurality of cleaved non-specific amplification products while maintaining a substantial proportion of said plurality of target-specific amplification products. Any appropriate resolvase may be used. In particular, the resolvase may be one of: T4 endonuclease VII or T7 endonuclease I. In some examples the resolvase is T4 endonuclease VII.

In general, the resolvases described herein may be one of: a Holliday junction resolvase, a T7 endonuclease I, a T4 endonuclease VII, a homolog of T7 endonuclease I (e.g., homologs from other bacteriophages), a homolog of T4 endonuclease VII, a flap endonuclease (FEN), a homolog of FEN (e.g., homologs from bacteria, archaea and eukaryotes), an endonuclease V, a homologs of endonuclease V (e.g., homologs from bacteria, archaea and eukaryotes), an *E. coli* endonuclease V, a *Thermotoga maritima* endonuclease V, a structure-specific endonuclease (e.g., from bacteria, archaea and Eukarya); a mismatch repair enzyme, a nuclease S1, a nuclease P1, a mung bean nuclease, a CEL nuclease, an endonuclease CEL I, transcription factor SP1, and combinations, fusions, or mutations thereof. Mutations may include mutations that retain at least some of the resolvase function.

For example, a method of reducing non-specific amplification products from a template-dependent primer extension reaction may include: amplifying a plurality of target nucleic acids using a plurality of pairs of target-specific primers to form a mixture comprising a plurality of target-specific amplification products and a plurality of non-specific amplification products; introducing a resolvase into the mixture that recognizes an aberrant DNA structure and cleaving the plurality of non-specific amplification products with the resolvase to generate a plurality of cleaved non-specific amplification products while maintaining a substantial proportion of said plurality of target-specific amplification products, wherein the resolvase is one of: T4 endonuclease VII or T7 endonuclease I; and removing the cleaved non-specific amplification products, leaving the substantial proportion of said plurality of target-specific amplification products.

A method of reducing non-specific amplification products from a template-dependent primer extension reaction may include: amplifying a plurality of target nucleic acids using a plurality of pairs of target-specific primers to form a mixture comprising a plurality of target-specific amplification products and a plurality of non-specific amplification products; introducing T4 endonuclease VII into the mixture, wherein the T4 endonuclease VII recognizes an aberrant DNA structure on the non-specific amplification products; cleaving the plurality of non-specific amplification products with the T4 endonuclease VII to generate a plurality of cleaved non-specific amplification products while maintaining more than 50% of said plurality of target-specific amplification products; and removing the cleaved non-specific amplification products, leaving the substantial proportion of said plurality of target-specific amplification products.

In any of these methods, after amplification of the polynucleotides and cleavage with a resolvase, a DNA ligase may be used to seal any nicks incurred on the specific targets (and non-consequently, the non-specific products), and one or more rounds of PCR may be performed to amplify the targets. In such cases, the first plurality of pairs of target-specific primers may contain at least part of the sequence of the second PCR primers.

For example, a method of reducing non-specific amplification products from a template-dependent primer extension reaction may include: amplifying a plurality of target nucleic acids using a plurality of pairs of target-specific primers to form a mixture comprising a plurality of target-specific amplification products and a plurality of non-specific amplification products; introducing a resolvase into the mixture that recognizes an aberrant DNA structure and cleaving the plurality of non-specific amplification products with the resolvase to generate a plurality of cleaved non-specific amplification products while maintaining a substantial proportion of said plurality of target-specific amplification products, wherein the resolvase is one of: T4 endonuclease VII or T7 endonuclease I; removing the cleaved non-specific amplification products, leaving the substantial proportion of said plurality of target-specific amplification products; repairing nicks on the target-specific amplification products with a DNA ligase; and re-amplifying the target-specific amplification products.

In any of these methods, the method may also include removing the cleaved non-specific amplification products, leaving the substantial proportion of said plurality of target-specific amplification products.

Any of the methods described herein may include analyzing the target-specific amplification products. Analyzing may include any appropriate method or technique, including but not limited to sequencing, such as next-generation sequencing reaction.

Amplification may include any appropriate polynucleotide amplification technique, including in particular a multiplex polymerase chain reaction (PCR).

In general, the target nucleic acids may comprise DNA or RNA, for example, genomic DNA or cDNA.

The target-specific primers may comprise any appropriate plurality of pairs, such as 7 pairs or more (e.g., at least 7 pairs) of target-specific primers, such as 10 pairs or more (e.g., at least 10 pairs) of target-specific primers, between 7 pairs and 100,000 pairs, between 7 pairs and 1000 pairs, between 1,000 pairs to 100,000 pairs, over 100.000 pairs of target-specific primers, etc., between 10 pairs and 100,000 pairs, between 10 pairs and 1000 pairs, etc.

In any of the methods described herein, the resolvase recognizes an aberrant polynucleotide (e.g., DNA) structure. In particular, the resolvase recognizes an aberrant polynucleotide structure comprising at least one of Holliday structures or junctions, branched DNAs, Y-structures, cruciforms, heteroduplex loops, bulky adducts, single-stranded overhangs, DNA mismatches, or non-perfectly-matched DNAs.

Any of these methods may include performing end repair on the plurality of target-specific amplification products and a plurality of non-specific amplification products, either before or after introducing and/or treating with the resolvase. For example, any of the methods described herein may include performing end repair on the plurality of target-specific amplification products and a plurality of non-specific amplification products before introducing the resolvase.

Any of these methods may include ligating adapters to the substantial proportion of said plurality of target-specific amplification products following the introduction of the resolvase. The adapters may comprise at least three consecutive phosphorothioates.

As mentioned, any of these methods may include cleaving said non-specific amplification products with an exonuclease. For example, any of these methods may include cleaving said non-specific amplification products with an exonuclease comprising at least one of lambda exonuclease or *E. coli* exonuclease I after performing end-repair and adapter ligation on the plurality of target-specific amplification products and a plurality of non-specific amplification products.

The treatment with the resolvase may be performed at any appropriate conditions (e.g., resolvase concentration, treatment time, temperature, etc.). In general, cleaving said non-specific amplification products with the resolvase may include exposing the non-specific amplification products and the plurality of target-specific amplification products to between about 0.2 Units (U) and 1000 U of one or more resolvase for between about 0.5 minutes and 60 minutes (e.g., 0.5 minutes for 30 minutes, 20 minutes, 15 minutes, etc.) at between 10° C. and 40° C. (e.g., more particularly between 16° C. and 37° C.).

In any of the methods described herein the resolvase treatment may be titrated so that a predetermined substantial proportion of said plurality of target-specific amplification products is maintained in the mixture. The substantial proportion of the plurality of target-specific amplification products may comprise 30% or more (and/or greater than 30%), 40% or more (and/or greater than 40%), 50% or more (and/or greater than 50%), 60% or more (and/or greater than 60%), 70% or more (and/or greater than 70%), 80% or more (and/or greater than 80%), 90% or more (and/or greater than 90%), 95% or more (and/or greater than 95%) of the plurality of target-specific amplification products. Thus, the resolvase reaction may be performed, but stopped to prevent substantial cleavage of the target-specific amplification product. This may be adjusted by adjusting the resolvase treatment conditions as discussed above (e.g., about 0.2 Units (U) and 1000 U of one or more resolvase for between about 0.5 minutes and 60 minutes, e.g., 0.5 minutes for 30 minutes, 20 minutes, 15 minutes, etc., at between 10° C. and 40° C., e.g., more particularly between 16° C. and 37° C.). The appropriate resolvase buffer conditions may be used as described herein.

Also described herein are kits for performing any of the methods described herein. For example, a kit for a template-dependent primer extension reaction that selectively removes non-specific amplification products may include: a polymerase; a plurality of target-specific primer pairs; an amplification buffer; a resolvase buffer; at least one resolvase that recognizes and cuts a polynucleotide having an aberrant DNA structure; and instructions for use of said kit for removing non-specific amplification products from an amplification reaction following amplification using the resolvase. Any of these kits may include at least one nucleic acid adapter, including at least one nucleic acid adapter comprising at least three phosphorothioates.

As mentioned above, the target-specific primers in the kit may comprise at least 7 pairs of target-specific primers (7 or more, 10 or more, at least to, 100 or more, 1000 or more 10,000 or more, between 7 and 100,000, between 7 and 10,000, between 7 and 1000, between 10 and 100,000, between 10 and 10,000, between 10 and 1000, between 100 and 100,000, between 100 and 10,000, between 100 and 1000, between 1000 and 100,000, between 1000 and 10,000, etc.). For example, the kit may include about 1,000 to about 100,000 target-specific primers. In some variations, the kit includes over 100,000 target-specific primers.

The kit may include any appropriate resolvase that recognizes an aberrant polynucleotide (e.g., DNA) structure, such as an aberrant polynucleotide structure comprising at least one of Holliday structures or junctions, branched DNAs, Y-structures, cruciforms, hetereoduplex loops, bulky adducts, single-stranded overhangs, DNA mismatches, or non-perfectly-matched DNAs. For example, the resolvase may be T4 endonuclease VII.

Any of the kits described herein may also include one or more exonuclease for cleaving the non-specific amplification products. For example, a kit may include an exonuclease for cleaving the non-specific amplification products wherein the exonuclease comprises lambda exonuclease or E. coli exonuclease I.

Also described herein are methods of reducing non-specific amplification products from a template-dependent primer extension reaction that include the steps of: amplifying a plurality of target nucleic acids using a plurality of pairs of target-specific primers to form a mixture comprising a plurality of target-specific amplification products and a plurality of non-specific amplification products; introducing the mixture to a protein that recognizes and binds a polynucleotide having an aberrant DNA structure to remove said non-specific amplification products while maintaining a substantial proportion of the plurality of target-specific amplification products, wherein said aberrant DNA structure comprises at least one of Holliday structures or junctions, branched DNAs, Y-structures, cruciforms, hetereoduplex loops, bulky adducts, single-stranded overhangs, DNA mismatches, or non-perfectly-matched DNAs.

In particular, the protein that recognizes and binds a polynucleotide having an aberrant DNA structure may be MutS. In general, the protein that recognizes and binds a polynucleotide having an aberrant DNA structure may be linked to a substrate. As detailed herein, an enzyme that is used to absorb but not cleave the non-specific amplification products can be any MutS from different species, or human endonuclease V. A preferred enzyme is MutS from E. coli, or a mixture of MutS from E. coli and T. aquaticus, and human endonuclease V.

As mentioned above, any of the methods described herein may include analyzing the target-specific amplification products, for example by sequencing (e.g., next-generation sequencing reaction).

In general amplification may include performing a multiplex polymerase chain reaction (PCR). The target nucleic acids may comprise DNA and/or RNA. The target nucleic acids are genomic DNA or cDNA. Any appropriate number of target-specific primers may be used (e.g., greater than 6, 10, 100, 1000, 10,000, 100,000, etc.).

As mentioned, any of the methods described herein may also include performing end repair on the plurality of target-specific amplification products and a plurality of non-specific amplification products before introducing the protein that recognizes and binds a polynucleotide having an aberrant DNA structure. Any of these methods may include ligating adapters to the substantial proportion of said plurality of target-specific amplification products following the introduction of the protein that recognizes and binds a polynucleotide having an aberrant DNA structure. The adapters may include at least three consecutive phosphorothioates.

The step of introducing a protein that recognizes and binds a polynucleotide having an aberrant DNA structure may include incubating the non-specific amplification products and the plurality of target-specific amplification products for any appropriate time and incubation conditions, such as between about 0.5 minutes and 60 minutes (e.g., 0.5 min and 40 min, 0.5 min and 30 min, 0.5 min and 20 min, etc.) at between about 10° C. and 40° C. 9 (e.g. between 15° C. and 37° C., 20° C. and 40° C., etc.).

The methods for reducing non-specific amplification products in an amplification reaction, such as a multiplex PCR described herein can include any appropriate composition of an amplification reaction, which can be any reaction which makes use of a plurality of DNA primers. Multiplex PCR reaction can be any multiplex PCR known in the field. More specifically, the template can be DNA from any source; any thermophilic DNA polymerase can be used, and without limitation, any functional pH, salt concentration, additives, concentration of dNTPs, primers, and any number of primer pairs from 7 to over 100,000 (or more) can be employed. Any functional number of cycles of the amplification reaction from 2 to over 30, depending on the number of primer pairs used can also be employed. In some instances, non-specific amplification products generated from amplification reactions, such as in a multiplex PCR, can be reduced from about 0% to about 50% of the total amount of amplification products following the methods and/or using the kits, described herein and in greater detail below. As detailed herein, an enzyme ("resolvase") that is used to cleave the non-specific amplification products can be any one from the defined aberrant DNA structure-specific enzymes. A preferred, but not limiting, enzyme is T7 endonuclease I or T4 endonuclease VII.

In general, a resolvase is an enzyme or collection of enzymes that recognizes an aberrant DNA structure specifically and cuts at or near the aberrant DNA structure. Thus, a resolvase may be referred to as an aberrant DNA structure-specific enzyme (generically referred to herein as a resolvase) and may cleave the non-specific amplification products at or near the aberrant DNA structures on the polynucleotide. The aberrant DNA structures may include at least one of Holliday structures or junctions, branched DNAs, Y-structures, cruciforms, hetereoduplex loops, bulky adducts, single-stranded overhangs, DNA mismatches, or other non-perfectly-matched DNAs. They may further include structures comprising more than two strands of single-stranded DNA fragments. They may be aggregates of primers or primer-template DNA with no significant base pairing. A preferred aberrant DNA structure-specific enzyme is T7 endonuclease I or T4 endonuclease VII. Other enzymes that may be resolvase (or may be used as part of a cocktail of enzymes acting as resolvases) may include: Holliday junction resolvases, Ser-recombinases, Tyr-recombinases, Cre recombinases, Hin recombinase, Integrases, Recombinase A (RecA), etc. One or more (e.g. combinations) of these may be used.

As detailed herein, after enzymatic cleavage, the cleaved non-specific amplification products can be either removed by purification (by any common purification method with size selection, such as AMPure beads or column filtration) or, in the alternative, not removed. Moreover, and as described herein, nicks in the specific amplification products may be further filled, e.g., using any one of the following enzymes: 9° N™ DNA ligase, Taq DNA ligase, Tth DNA ligase, Tfi DNA ligase, Ampligase®, etc. Afterwards, the specific amplification products can be further amplified by PCR, particularly when nested primers are used in the amplification reaction.

Further, after amplification and before the enzymatic cleavage, the amplification products can be end repaired by methods known to those skilled in the art. Adapters can be added onto both ends of the said end-repaired specific amplification products by ligation. The ligase used is a combination of T4 DNA ligase and one of the following: 9° N™ DNA ligase, Taq DNA ligase, Tth DNA ligase, Tfi DNA ligase, Ampligase®, etc. The adapters can contain at either 3' or 5' end phosphorothioates, or biotin, or other chemical groups or proteins that prevent the adapters from the digestion of exonucleases. After ligation of the adapters, the cleaved non-specific amplification products can be further digested by exonucleases known to those skilled in the art. Following digestion of the cleaved non-specific amplification products with exonucleases, the adapter-ligated specific amplification products can be further amplified by PCR.

Thus, method of generating an amplification reaction having reduced non-specific amplification products are disclosed and may include: providing a nucleic acid sample comprising at least one target nucleic acid; amplifying at least one target nucleic acid using target-specific primers wherein the amplifying generates a plurality of target-specific amplification products and a plurality of non-specific amplification products; and introducing an aberrant DNA structure-specific enzyme for cleaving the non-specific amplification products to generate a plurality of cleaved non-specific amplification products while maintaining a substantial proportion of the plurality of target-specific amplification products.

As mentioned, any of these methods may further involve removing the cleaved non-specific amplification products. The aberrant DNA structure-specific enzyme (resolvase) may cleave the non-specific amplification products at aberrant DNA structures. The aberrant DNA structures may include at least one of Holliday structures or junctions, branched DNAs, Y-structures, cruciforms, hetereoduplex loops, bulky adducts, single-stranded overhangs, DNA mismatches, or other non-perfectly-matched DNAs. They may further include structures comprising more than two strands of single-stranded DNA fragments. They may be aggregates of primers or primer-template DNA with no significant base pairing. A preferred aberrant DNA structure-specific enzyme is T7 endonuclease I or T4 endonuclease VII.

The methods described herein may involve combining the cleaved non-specific amplification products with an exonuclease. The exonuclease may be at least one of lambda exonuclease or E. coli exonuclease I. Further, the method may involve, prior to combining the cleaved non-specific amplification products with the exonuclease, the target-specific amplification products being protected from cleavage by the exonuclease. The protecting may involve ligating adapters to both ends of said target-specific amplification products. The adapters may include at least three consecutive phosphorothioates. Optionally, the at least three consecutive phosphorotioates will include three, four, five, or six consecutive phosphorotioates. Further, the method may involve ligating which is performed by T4 DNA ligase.

Further, the ligating may further involve at least one of 9° N™ DNA ligase, Taq DNA ligase, Tth DNA ligase, Tfi DNA ligase, or Ampligase®.

As mentioned, kits for removing non-specific amplification products from an amplification reaction are described. A kit may include at least one aberrant DNA structure-specific enzyme (resolvase); a buffer; and instructions for use of the kit for removing non-specific amplification products from said amplification reaction. The kit may include at least one nucleic acid adapter. The at least one nucleic acid adapter may include at least three phosphorothioates. Further, the at least three phosphorothioates may include three, four, five, or six phosphorothioates. The at least three phosphorothioates may be consecutive. The kit may further include reagents to perform a multiplex polymerase chain reaction (PCR), wherein the reagents include at least a buffer, dNTPs, a DNA polymerase, and, optionally, at least one pair of target-specific primers. The at least one pair of target-specific primers may include at least 7 pairs of target-specific primers. Further, the kit may include at least one exonuclease. The at least one exonuclease may include lambda exonuclease or E. coli exonuclease I.

A kit for removing non-specific amplification products from an amplification reaction may include at least one DNA mismatch-binding protein; a buffer; and instructions for use of the kit for removing non-specific amplification products from the amplification reaction. The DNA mismatch-binding protein may be, e.g., MutS.

Aberrant DNA structure-specific enzymes for use in reducing non-specific amplification products in an amplification reaction are disclosed herein. The aberrant DNA structure-specific enzyme may cleave the non-specific amplification products in the vicinity of the start of the aberrant DNA structures or in the aberrant DNA structures. The aberrant DNA structures may include at least one of Holliday structures or junctions, branched DNAs, Y-structures, cruciforms, hetereoduplex loops, bulky adducts, single-stranded overhangs, DNA mismatches, or other non-perfectly-matched DNAs. They may further include structures comprising more than two strands of single-stranded DNA fragments. They may be aggregates of primers or primer-template DNA with no significant base pairing. The aberrant DNA structure-specific enzyme may be T7 endonuclease I or T4 endonuclease VI.

For example, described herein are methods of reducing non-specific amplification products from a template-dependent primer extension reaction, comprising: amplifying a plurality of target nucleic acids using a plurality of pairs of target-specific primers wherein said amplifying generates a plurality of target-specific amplification products and a plurality of non-specific amplification products; introducing a resolvase that recognizes an aberrant DNA structure and cleaving said non-specific amplification products with the resolvase to generate a plurality of cleaved non-specific amplification products while maintaining a substantial proportion of said plurality of target-specific amplification products, wherein the resolvase is one of: T4 endonuclease VII or T7 endonuclease I, further degrading the said digested non-specific amplification products and primers by an exonuclease, multiple exonucleases, or a combination of exonucleases and nucleases, (e.g., exonucleaes and nucleases may include one or more of exonuclease I, exonuclease VII, exonuclease T, RecJ, RecJf, S1 nuclease, P1 nuclease, mung bean nuclease); removing the digested non-specific products and primers by purification; re-amplify target DNA fragments by PCR; and analyze the target DNA fragments As mentioned, the template-dependent primer extension reaction may include any method involving a plurality of single-stranded oligonucleotides as primers, including multiplex PCR. The primers, may be single-stranded oligonucleotides; the number of primers may be from 7 pairs to 1,000,000 pairs (e.g. 7 or more pairs, etc.). The length of primers may be from 16-100 nucleotides; the length of amplicons may be from 20 bp-1500 bp.

The types of primers that may be used may include unmodified oligonucleotides, modified oligonucleotides, peptide nucleic acid (PNA); modified primers may contain one or more than one 5-methyl deoxycytidine and/or 2,6-diaminopurine, dideoxyinosine, dideoxyuridine, and biotin labeled oligonucleotides. One and/or both primers can contain barcodes or other sequences that allow for identification; one and/or both primers can contain adapter sequences.

Non-specific amplification products may contain primer-dimers and aberrant structures as described here; digestion of cleaved non-specific primers may be done by contacting amplification product with T4 endonuclease VII, as mentioned herein, or other endonuclease. Further degrading may be performed by contacting the digested non-specific products with one and/or more exonucleases or a combination of exonucleases and nucleases. In any of these methods, the amplified, purified product may be re-amplified, e.g., by PCR.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 8C shows the results before treatment with resolvase, and FIG. 8I) shows the results after treatment, illustrating the removal of non-specific amplification products generated in a multiplex amplification reaction with 207 pairs of primers.

FIG. 9A illustrates the results before treatment with resolvase and FIG. 9B shows the results after treatment and degradation of non-specific amplification products.

FIG. 22 shows a table (also referred to herein as Table 1) illustrating the quality confirmation based on sequencing from a library made using the method as described herein using multiplex amplification and treatment with resolvase to remove non-specific amplification products (in this example, using 207 pairs of primers).

FIG. 23 is a table (referring to herein as Table 2) illustrating the quality confirmation based on sequencing results from a library (generated with 207 pairs of long primers) of a method of using multiplex amplification and treatment with resolvase to remove non-specific amplification products as described herein.

FIG. 24 is a table (referred to herein as Table 3) illustrating the quality confirmation based on sequencing results from a library (generated with 16000 pairs of primers) of a method of using multiplex amplification and treatment with resolvase to remove non-specific amplification products as described herein.

FIG. 26 discloses SEQ ID NOS 9-12, respectively, in order of appearance.

FIG. 28A shows a 7-amplicon library assayed by High Sensitivity DNA kit of BioAnalyzer 2100. FIG. 28B shows the read count per amplicon against GC content of the 7-amplicon library. In FIG. 28C a library made with Paragon Genomics' TP53 whole exon panel was assayed by the High Sensitivity DNA kit of BioAnalyzer 2100. FIG. 28D shows the read count per amplicon against GC content of the TP53 whole exon library. In FIG. 28E, a library made with Paragon Genomics' BRAC1&2 whole exon panel was assayed by the High Sensitivity DNA kit of BioAnalyzer 2100. FIG. 28F shows the read count per amplicon against GC content of the BRAC1&2 whole exon library. In FIG. 28G, a library made with Paragon Genomics' generic cancer panel (GCP) was assayed by High Sensitivity DNA kit of BioAnalyzer 2100. FIG. 28H shows the read count per amplicon against GC content of the GCP library.

FIG. 32 illustrates the allele frequencies detected with GCP libraries made with Horizon Discovery's HD780 reference DNA.

DETAILED DESCRIPTION

Figure 1:
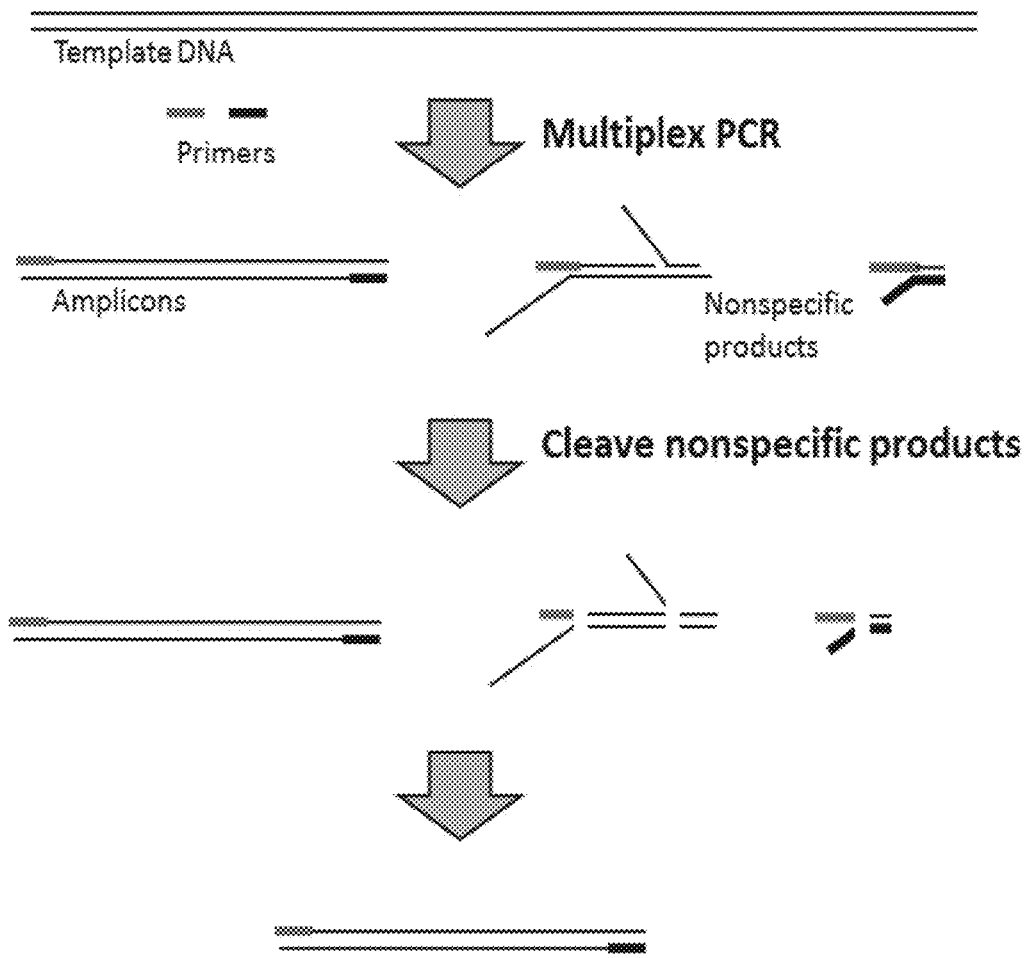
FIG. 1 schematically illustrates a method of the present disclosure to remove non-specific products generated in multiplex PCR by cleaving non-specific amplification products having aberrant polynucleotide structures.

In general, described herein are methods, compositions, systems and kits that may be used to amplify or improve amplification of target-specific amplification products by reducing non-specific amplification products (e.g., primer-dimers) when amplifying multiple different nucleotide regions. These methods, compositions, systems and kits typically include or include the use of one or more resolvases that recognize and bind to and/or cut an aberrant DNA structure.

For example, the methods provided herein can be used for the improvement of multiplex amplification (e.g., PCR) protocols or any other methods which involve a plurality of DNA primers or oligonucleotides. More particularly, the methods provided herein can be used for reducing non-specific amplification products in multiplex PCR protocols or any other methods which involve a plurality of DNA primers or oligonucleotides. The methods disclosed herein provide for optimized protocols for performing multiplex PCR reactions such that non-specific amplification products are removed and target DNA amplicons are preserved. Overall, the methods can relate to improved methods of nucleic acid library preparation.

In one aspect, the methods provide for reducing non-specific amplification products from an amplification reaction. The method can involve providing a nucleic acid sample comprising at least one target nucleic acid. The nucleic acids can be RNA or DNA. The DNA can be genomic DNA or cDNA or any combination thereof. The DNA can be single-stranded or double-stranded. The DNA can be derived from a eukaryotic cell, an archaea cell, a bacterial cell, a mycobacterial cell, a bacteriophage, a DNA virus, or an RNA virus, or converted from RNA. In some cases, the DNA can be derived from a mammal. In some cases, the DNA can be derived from a human. The DNA can be unmodified, or can be modified (e.g., methylated, glycosylated, etc.). The nucleic acids can be used in an amplification reaction. The nucleic acids used in the amplification reaction can comprise at least one target nucleic acid sequence. A target nucleic acid sequence generally refers to a nucleic acid sequence that is targeted and enriched, for example, with target-specific primers, in a mixture of nucleic acids. The amplification reaction can be any method involving hybridizing a plurality of DNA primers or oligonucleotides to their corresponding targets. The amplification can be a polymerase chain reaction (PCR). In one example, the amplification reaction is a multiplex PCR. In other examples, the amplification reactions can be amplification by ligation extension, nested multiplex PCR, whole genome amplification, whole exon amplification, or isothermal amplification reactions with more than one pair of oligonucleotides, etc. Serving as one example, multiplex PCR provides for the simultaneous amplification of a plurality of target nucleic acids in a single vessel (i.e., tube, well, vial, and the like) to generate a plurality of amplicons. Multiplex PCR generally involves the use of a plurality of target-specific primer pairs that can selectively enrich a plurality of target nucleic acids. The plurality of target-specific primer pairs can be from 7 primer pairs (e.g., 10 primer pairs) to over 100,000 primer pairs. In one case, the plurality of target-specific primer pairs comprises at least 7 pairs of target-specific primer pairs. In another case, the plurality of target-specific primer pairs comprises from about 7 to about 100 primer pairs. In another case, the plurality of target-specific primer pairs comprises from about 100 to about 1,000 primer pairs. In yet another case, the plurality of target-specific primer pairs comprises from about 1,000 to about 100,000 primer pairs. In a further case, the plurality of target-specific primer pairs comprises over 100,000 primer pairs.

Primers can comprise unmodified bases and/or phosphodiester bonds, or modified bases and/or phosphodiester bonds, unprotected 5' ends, or protected 5' ends, 5' phosphorylated, or 5' unphosphorylated ends. Primer pairs can be designed such that the amplicon length can be from under 100 to over 1000 base pairs. Multiplex PCR reactions as envisioned in this disclosure can be performed by thermostable DNA polymerases commonly used in PCR reactions. Thermostable DNA polymerases can be wild-type, can have 3'-5', 5'-3', or both 3'-5' and 5'-3' exonuclease activity, or can be a mixture of thermostable polymerases for higher fidelity, or can synthesize long amplicons, or have faster synthesizing rate. An example of a suitable thermostable DNA polymerase can be Taq DNA polymerase. The thermal profile (temperature and time) for the PCR can be optimized, the primer concentration can also be optimized to achieve the best performance. Finally any additives that can promote optimal amplification of amplicons can be used. These additives include, without limitation, dimethyl sulfoxide, betaine, formamide, Triton X-100, Tween 20, Nonidet P-40, 4-methylmorpholine N-oxide, tetramethylammonium chloride, 7-deaza-2'-deoxyguanosine, L-proline, bovine serum albumin, trehalose, and T4 gene 32 protein.

The methods described herein can involve amplifying a target nucleic acid using target-specific primers wherein the amplifying step generates a plurality of target-specific amplification products and a plurality of non-specific amplification products. Multiplex PCR reactions can generate a plurality of amplification products comprising a plurality of target-specific amplification products and a plurality of non-specific amplification products. In some cases, the plurality of target-specific amplification products may be the most abundant amplification products in the amplification reaction (i.e., greater than 50% of the amplification reaction products) and in other cases, the plurality of non-specific amplification products may be the most abundant amplification products in the amplification reaction. In some cases, it may be desirable to remove or reduce the non-specific amplification products to generate an amplification reaction having reduced non-specific amplification products (i.e., such that the target-specific amplification products are the most abundant amplification product in the amplification reaction).

Non-specific amplification products are often an undesirable by-product of a multiplex PCR reaction that can frustrate the ability to analyze target-specific amplification products in an amplification reaction. Formation of non-specific amplification products can be dependent upon the number of primer pairs utilized in the multiplex PCR reaction. The formation of non-specific amplification products in an amplification reaction can be a complex process that can be dependent upon a number of factors including: the number of primer pairs used, the temperature of the reaction, the salt concentration in the reaction, the length of the primers, the GC content of the primers, secondary structure formation, and competition between primer-primer binding and primer-template binding. In the early cycles of multiplex PCR, non-specific amplification products are first formed through partial annealing between primers, or partial annealing between primer-template DNA, or by aggregation of primers and/or primer and template DNA without significant base pairing. In these early stages of multiplex PCR, these non-specific amplification products can contain regions of non-perfectly matched DNA as parts of their structures (i.e. the partially annealed portions contain non-perfectly matched DNA structures, the newly synthesized portions are perfectly matched double-stranded DNA). In the later cycles of multiplex PCR, these non-perfectly matched regions become perfectly matched double-stranded DNA (i.e. the entire structures of non-specific amplification products become perfectly base-paired double-stranded DNA).

Surprisingly, the inventor has determined that within a limited number of PCR cycles (i.e., 8-28 cycles), the non-specific amplification products can be reduced by treating the multiplex PCR products with T4 endonuclease VII under conditions that favor cleaving aberrant DNA structures. T4 endonuclease VII and T7 endonuclease I, as well as others, belong to a group of enzymes that have a wide spectrum of substrates. It has been reported in a series of publications that T4 endonuclease VII and T7 endonuclease I recognize a variety of aberrant DNA structures that deviate from the perfectly matched double-stranded DNA, and cleave one or both strands of DNA within 1-10 bases of the start of the aberrant DNA structure. These aberrant DNA structures include branched DNAs, Y-structures, cruciforms, heteroduplex loops, bulky adducts, single stranded overhangs, mismatches, Holliday structures or junctions, and other kinds of non-perfectly-matched DNAs. They may further include structures comprising more than two strands of single-stranded DNA fragments. They may be aggregates of primers or primer-template DNA with no significant base pairing. Surprisingly, the non-specific amplification products formed in the first 8-28 cycles of multiplex PCR contain a variety of aberrant double-stranded and single-stranded DNA structures that can be cleaved by the enzymes that have similar activities with T4 endonuclease VII. Described herein are methods, compositions, systems and kits whereby non-specific amplification products generated in the first 8-28 cycles of multiplex PCR can be removed through cleavage with T4 endonuclease VII. These findings are of particular use to the methods of this disclosure.

The methods as disclosed herein can further involve contacting the amplification reaction with an enzyme for cleaving the non-specific amplification products thereby generating a plurality of cleaved non-specific amplification products. As used herein, the term "contacting" equates with introducing such enzyme to a pre-existing mixture as described herein. The methods of the present disclosure can use a variety of enzymes that can recognize and cleave aberrant DNA structures. In some cases, the enzymes useful to perform the methods as disclosed herein are aberrant DNA structure-specific enzymes. The term "aberrant DNA structure-specific enzyme" will be used herein to refer to an enzyme that binds to and cleaves aberrant DNA structures. The plural form will be used herein to refer to enzymes that bind to and cleave aberrant DNA structures. Aberrant DNA structure-specific enzymes will generally have, but will not be limited to, at least one activity that makes at least one break or cleavage event on either strand (i.e. sense or antisense) in the vicinity of or within an aberrant double-stranded DNA structure in a stretch of at least two pairs of imperfectly matched (i.e., non-complementary) bases. These aberrant DNA structure-specific enzymes can have a plurality of enzymatic activities that are not limited to the cleavage of aberrant DNA structures. The aberrant DNA structure-specific enzyme can cleave the phosphodiester bond of the DNA backbone resulting in a break or a nick in a single-strand of the double-stranded DNA. The aberrant DNA structure-specific enzymes disclosed herein can recognize a variety of aberrant DNA structures, including, without limitation, Holliday structures or junctions, branched DNAs, Y-structures, cruciforms, heteroduplex loops, bulky adducts, single stranded overhangs, mismatches, and other kinds of non-perfectly-matched DNAs. They may further include structures comprising more than two strands of single-stranded DNA fragments. They may be aggregates of primers or primer-template DNA with no significant base pairing. In some cases, the aberrant DNA structure-specific enzyme can recognize a particular type of aberrant DNA structure. In other cases, the aberrant DNA structure-specific enzyme can recognize more than one type of aberrant DNA structure. Methods as provided herein can combine an aberrant DNA structure-specific enzyme that can recognize and cleave aberrant DNA structures generated in an amplification reaction comprising a plurality of target-specific amplification products and a plurality of non-specific amplification products. In some cases, the aberrant DNA structure-specific enzyme can selectively cleave non-specific amplification products. In some cases, the aberrant DNA structure-specific enzyme can cleave both non-specific amplification products and target-specific amplification products. In some examples, the aberrant DNA structure-specific enzyme can reduce the amount of non-specific amplification products in the amplification reaction without reducing the amount of target-specific amplification products. In other examples, both non-specific amplification products and target-specific amplification products can be reduced. In some cases, the amplification reaction can be substantially free of non-specific amplification products. Substantially free of non-specific amplification products can mean that the amount of non-specific amplification products in the amplification reaction have been reduced by greater than 50%, 60%, 70%, 80%, 85%, 90%, 91%, 92%, 93%, 94%, 95%, 96%, 97%, 98%, 99%, up to 100%.

Examples of aberrant DNA structure-specific enzymes that can be utilized to cleave the aberrant DNA structures in the methods provided herein include, without limitation, bacteriophage Holliday junction resolvase T7 endonuclease I from phage T7, or its homologs from phage T3, YeO3-12; T4 endonuclease VII from phage T4, or its homologs from phage YeO3-12, L5, D29; Rap from phage Lambda, A22 from poxvirus, or their homologs from phage P22, H-19B, 933 W, 21, PS34, VT2-Sa, D3; RuvC-like endonuclease from phage bIL66/67/70, or its homologs from phage sk1, c2, vML3, 712; RusA from r1t, G44P from phage SPP1, or their homologs from phage Tuc, u136, g1e, 82, HK122/97, PVL, TM4, A118; flap endonuclease (FEN), or its homologs from bacteria, archaea and eukaryotes; endonuclease V or its homologs from bacteria, archaea and eukaryotes including *E. coli* endonuclease V, *Thermotoga maritima* endonuclease V; structure-specific endonucleases from bacteria, archaea and eukarya, including RuvC, RecU, Hjc, Hje, Hjr, CCE1, YDC2, XPG class: GEN1/Yen1, UvrC class: Slx1-Slx4, ERCC4 class: Xpf (Xpf-Ercc1), Mus81 (MUS81-EME1/Mms4); mismatch repair enzymes MutHLS from bacteria; single-strand specific nucleases from fungi and plants, these include S1 nuclease from *Aspergillus oryzae*, P1 nucleases from *Penicillium citrinum*, mung bean nuclease, or the CEL nuclease family (CEL I and SP1). Examples of enzymes that can be utilized to bind but not cleave the aberrant DNA structures in the methods provided herein include, without limitation, MutS from bacteria or human endonuclease V. In specific examples, the aberrant DNA structure-specific enzyme can be T7 endonuclease I or T4 endonuclease VII. It should be understood that essentially any aberrant DNA structure-specific enzyme or its mutant that can perform the methods of the disclosure as described herein is envisioned. More particularly, any aberrant DNA structure-specific enzyme or its mutant that can cleave or bind aberrant DNA structures can be used.

In other methods of the disclosure, non-specific amplification products can be removed from the amplification reaction without the cleavage of the aberrant DNA structures. In this case, the amplification reaction comprising a plurality of target-specific amplification products and non-specific amplification products can be contacted with a DNA mismatch-binding protein. Proteins of this type can be enzymes involved in the DNA mismatch repair pathway, a system for recognizing and repairing DNA mismatches during DNA synthesis or recombination. In these examples, the DNA mismatch-binding protein can selectively bind DNA base pair mismatches (i.e., non-complementary base pairing), including a stretch of unpaired bases, in a nucleic acid sample. In these examples, non-specific amplification products can selectively bind to the DNA mismatch-binding protein, whereas target-specific amplification products will not bind to the DNA mismatch-binding protein. DNA mismatch-binding proteins useful in the methods described herein can be any DNA mismatch-binding protein that can recognize and bind to at least one DNA mismatch in a nucleic acid sample. In one particular example, the DNA mismatch-binding protein can be MutS. MutS can be derived from a bacterium, in some cases *E. coli* or *T. aquaticus*. In some cases, the DNA mismatch-binding protein can be immobilized on a solid support. In this example, the non-specific amplification products can be absorbed onto the solid support and removed from the amplification reaction. Although particular examples have been disclosed, essentially any substance that can selectively bind non-specific amplification products can be used.

In some cases, the methods can involve removing the cleaved non-specific amplification products from the amplification reaction. In other cases, the cleaved non-specific amplification products are not removed. The cleaved non-specific products may be further digested into small oligonucleotides and nucleotides by exonucleases. These include double-stranded-DNA-specific exonucleases and single-stranded-DNA-specific exonucleases. In some cases, the exonucleases can be lambda exonuclease, *E. coli.* exonuclease I, or a combination of the two. In this example, it may be desirable to protect the ends of the target-specific amplification products from digestion with the exonuclease. In this case, the exonuclease will digest the non-specific amplification products and not the target-specific amplification products. In one example, protecting the target-specification amplification products from digestion can involve the ligation of adapters to the ends of the target-specific amplification products. These adapters can have a plurality of consecutive phosphorothioates at the 3' end of the sense-strand. Phosphorothioates are variants of normal DNA that are resistant to cleavage by nucleases. In some cases, the adapters may comprise 3, 4, 5, 6, or more than 6 consecutive phosphorothioates at the 3' end of the sense-strand. In one example, the adapters can be adapters used for making libraries for next-generation sequencing, as described in more detail below. Adapters can further comprise barcodes or tags. The adapter-ligated target DNA fragments can be further amplified by PCR. In some cases, the adapters are phosphorylated at the 5' end of the sense strand. In some cases, the 3' end of the anti-sense strand of the adapter can have a thymine (T) overhang. In this example, the T overhang of the adapter can be ligated to an end-repaired, A-tailed target-specific amplification product.

In some cases, the amplification products described herein can be used to prepare libraries for next-generation sequencing. Adapters useful for next-generation sequencing applications can be ligated to the ends of target-specific amplification products, as described above. In some cases, the adapters can have a plurality of consecutive phosphorothioates at the 3' end of the sense-strand. In some cases, the adapters may comprise 3, 4, 5, 6, or more than 6 consecutive phosphorothioates at the 3' end of the sense-strand. The adapters can be sequencing adapters useful on a next-generation sequencing platform (e.g., Illumina TruSeq adapters). For example, the methods of the invention are useful for next-generation sequencing by the methods commercialized by Illumina, as described in U.S. Pat. No. 5,750,341 (Macevicz); U.S. Pat. No. 6,306,597 (Macevicz); and U.S. Pat. No. 5,969,119 (Macevicz).

Kits

The present disclosure further provides for kits useful to practice the methods disclosed herein. In one aspect, the disclosure provides a kit for performing a multiplex PCR reaction and for reducing non-specific amplification products. In this example, the kit can comprise reagents suitable for use in a multiplex PCR reaction, for example, without limitation, a buffer, dNTPs, and a DNA polymerase (e.g., Taq DNA polymerase). A plurality of primer pairs for use in the multiplex PCR reaction can be sold separately. In some cases, the primer pairs are custom-made. In some cases, the primer pairs are selected by the customer. In some cases, the primer pairs are target-specific primer pairs. In other cases, the primer pairs can be random primer pairs. Primer pairs can comprise from 10 to over 100,000 primer pairs. The kit of this example can further comprise an aberrant DNA structure-specific enzyme and a buffer suitable for reducing non-specific amplification products (e.g., T4 endonuclease VII). The kit of this example can further comprise a DNA polymerase (e.g., Taq DNA polymerase) and a pair of PCR primers to perform a second round of PCR.

In another case, the disclosure provides for a kit for preparing an adapter-ligated library for next-generation sequencing. In this example, the kit can comprise any of the reagents disclosed above for performing a multiplex PCR reaction and for reducing non-specific amplification products as well as additional reagents for library preparation. Additional reagents for library preparation can comprise, without limitation, enzymes and buffers suitable for end repairing (e.g., Klenow polymerase and/or T4 DNA polymerase), enzymes and buffers suitable for phosphorylating the 5' ends of the amplification products (e.g., T4 polynucleotide kinase), enzymes and buffers suitable for A-tailing (e.g., Taq DNA polymerase), adapters, DNA ligases and buffers suitable for performing a ligation reaction, an exonuclease (e.g., lambda exonuclease, exonuclease I), and PCR primers for amplifying adapter-ligated nucleic acids. Adapters can be any adapters or combinations thereof as disclosed herein, including adapters that comprise a plurality of phosphorothioates and/or adapters suitable for next-generation sequencing. DNA ligases can comprise T4 DNA ligase and at least one additional ligase selected from the group consisting of 9° N™ DNA ligase, Taq DNA ligase, Tth DNA ligase, Tfi DNA ligase, and Ampligase®. PCR primers that are used for amplifying adapter-ligated nucleic acids can comprise a sequence that anneals to at least a portion of the adapter sequence.

In another case, the disclosure provides for kits for performing a multiplex PCR reaction and an alternative method for reducing non-specific amplification products. In this example, the kit can comprise reagents suitable for use in a multiplex PCR reaction, for example, without limitation, a buffer, dNTPs, and a DNA polymerase (e.g., Taq DNA polymerase). A plurality of primer pairs for use in the multiplex PCR reaction can be sold separately. In some cases, the primer pairs are custom-made. In some cases, the primer pairs are selected by the customer. In some cases, the primer pairs are target-specific primer pairs. In other cases, the primer pairs can be random primer pairs. Primer pairs can comprise from 10 to over 100,000 primer pairs. The kit can further comprise a DNA-mismatch binding protein, for example, MutS. In some cases, a solid support with MutS bound to the surface can be provided in the kit. In other cases, MutS and the solid support can be provided separately with reagents suitable for binding MutS to the solid support. The kit can further comprise any suitable wash buffers, elution buffers, and the like suitable for performing the methods of the present disclosure.

Particular reference will now be made to specific aspects and figures of the disclosure. Such aspects are provided by way of example only. Numerous variations, changes, and substitutions will now occur to those skilled in the art without departing from the disclosure.

In FIG. 1, multiplex PCR is conducted with template DNA, primers, dNTPs and a thermostable DNA polymerase. The number of pairs of primers can be any number from under 10 (e.g., 7) to over 100,000 in a single reaction in a single tube or well. The PCR products include target DNA fragments, i.e. the amplicons, and various non-specific products containing aberrant DNA structures. The products are contacted with T4 endonuclease VII, which makes double-stranded breaks in the vicinity of aberrant DNA structures, while the target DNA fragments remain intact. The target DNA fragments are obtained, with or without further purification to remove the cleaved non-specific products, and used in various downstream applications. E. coli. exonuclease I may be used together with T4 endonuclease VII after multiplex PCR to degrade single-stranded DNA into small oligonucleotides and nucleotides. The target DNA fragment may be labeled with fluorescence or radioisotopes by nick translation and analyzed in microarray, hybridization, or other techniques for detection and diagnosis. Further, the nicks in the target DNA fragments can be filled with any one of the following enzymes: 9° N™ DNA ligase, Taq DNA ligase, Tth DNA ligase, Tfi DNA ligase, Ampligase®, etc. After filling the nicks, the DNA fragments can be further amplified by PCR, provided that nested primers are used in the multiplex PCR.

In FIG. 1 the schematic diagram of a procedure to remove non-specific amplification products generated in multiplex PCR shows that after multiplex PCR, the non-specific amplification products may be cut with a resolvase (in this example, T4 endonuclease VII) and optionally removed by purification. The target amplicons may either be used in the subsequent step directly, or subjected to a further round of PCR to either increase the yield or add additional sequences, such as adapters, and used as libraries.

Figure 2:
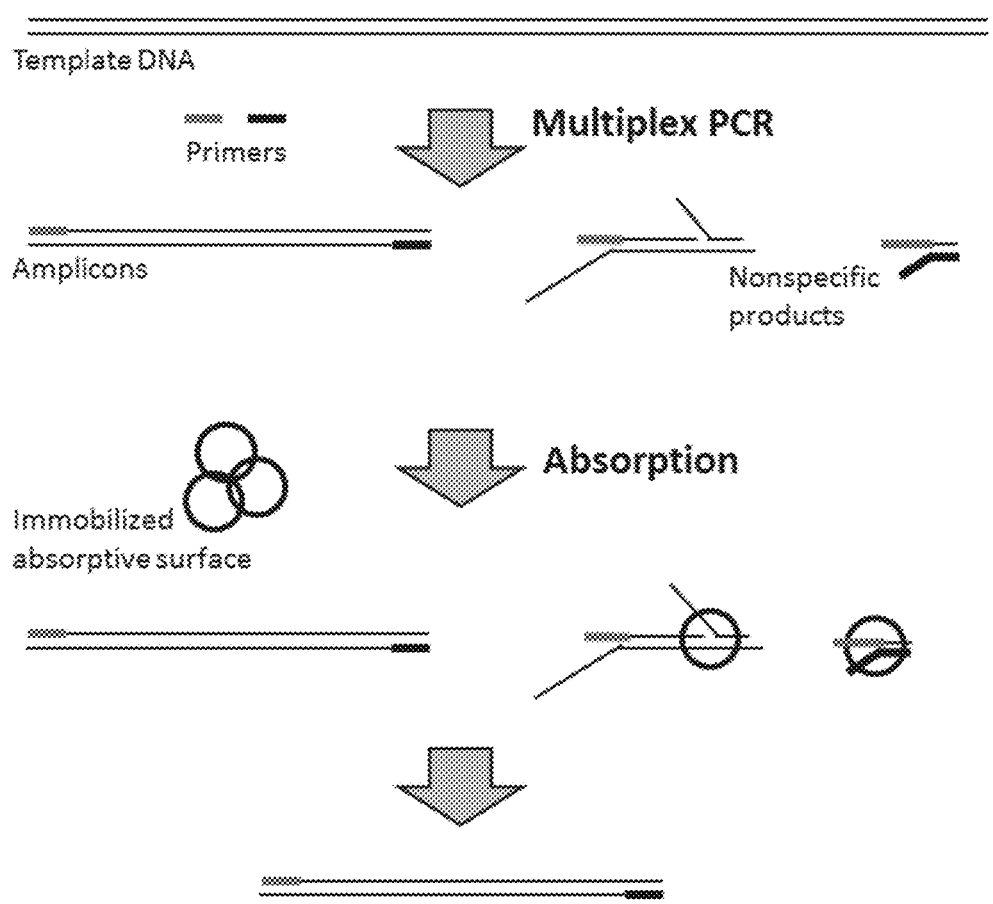
FIG. 2 shows another example of a method of the present disclosure to remove non-specific products generated in multiplex amplification by absorption of non-specific amplification products having aberrant polynucleotide structures.

Alternatively or additionally, the protein (e.g., resolvase) that binds to the aberrations in the polynucleotide may be used to bind to, and remove, rather than just cut, the non-specific binding amplification products. For example, a resolvase or the aberration-binding portion of the resolvase may be tethered to a solid phase substrate. FIG. 2 is a schematic diagram of a procedure to remove non-specific amplification products generated in multiplex PCR. After multiplex PCR, the non-specific amplification products are absorbed onto immobilized MutS or a combination of immobilized MutS from different organisms, while the target DNA fragments are in the solution and separated from the non-specific products. The immobilized MutS may be contained in a column or cartridge and from *E. coli.* or *Thermus aquaticus*. The MutS includes one or more binding sites for binding to aberrations in a polynucleotide.

In FIG. 2, a multiplex PCR is conducted with template DNA, primers, dNTPs and a thermophilic DNA polymerase. The number of pairs of primers can be any number from 7 to over 100,000 in a single reaction in a single tube or well. The PCR products include target DNA fragments, i.e. the amplicons, and various non-specific products containing aberrant DNA structures. These PCR products are contacted with immobilized MutS or a combination of immobilized MutS from different organisms. The non-specific products are absorbed onto the immobilized proteins, while the target DNA fragments are in the solution and separated from the non-specific products. As mentioned, the immobilized MutS may be from *E. coli.* or *Thermus aquaticus*.

Figure 3:
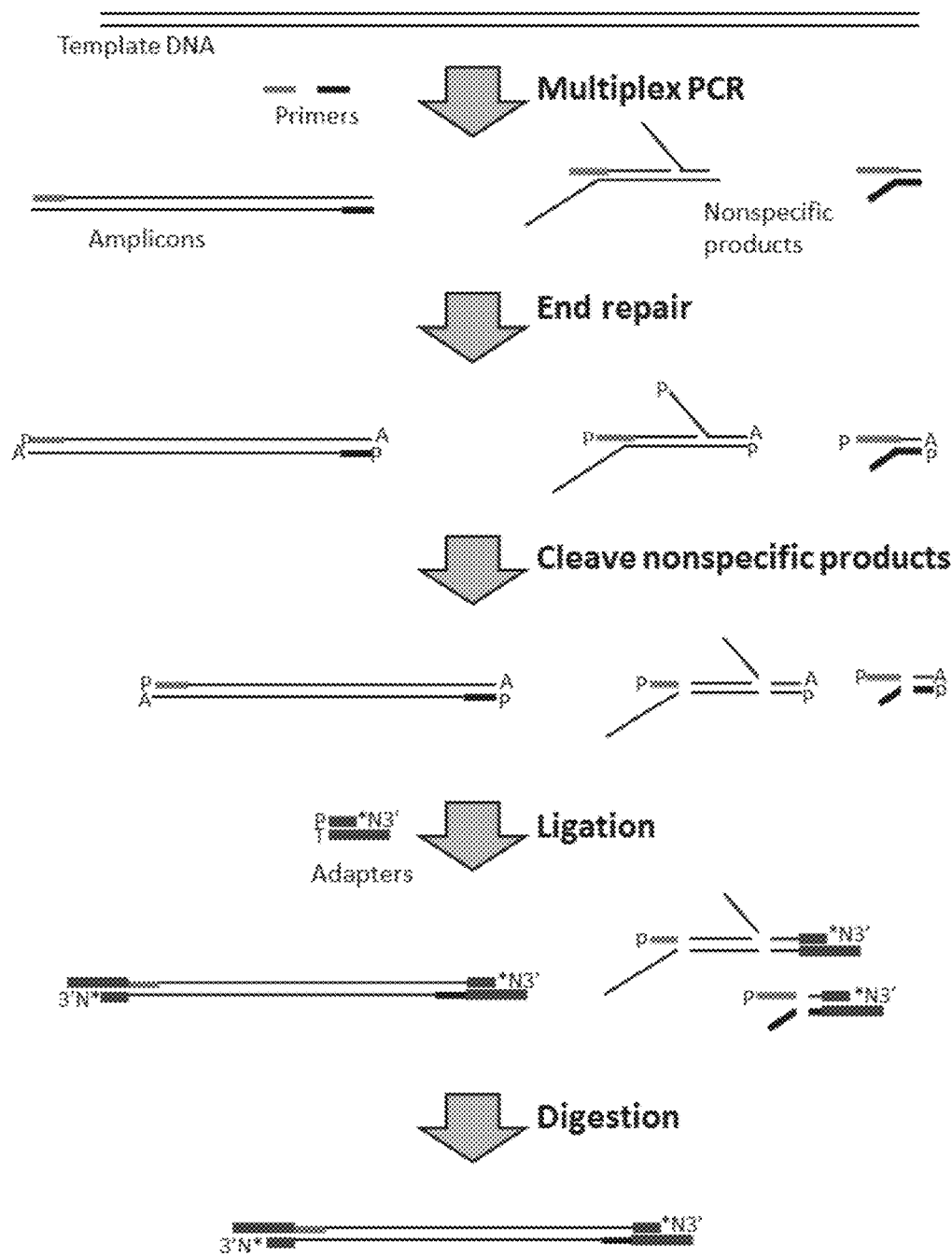
FIG. 3 illustrates another example of a method of the present disclosure to obtain target polynucleotide amplification products from a multiplex amplification reaction.
Figure 21B:
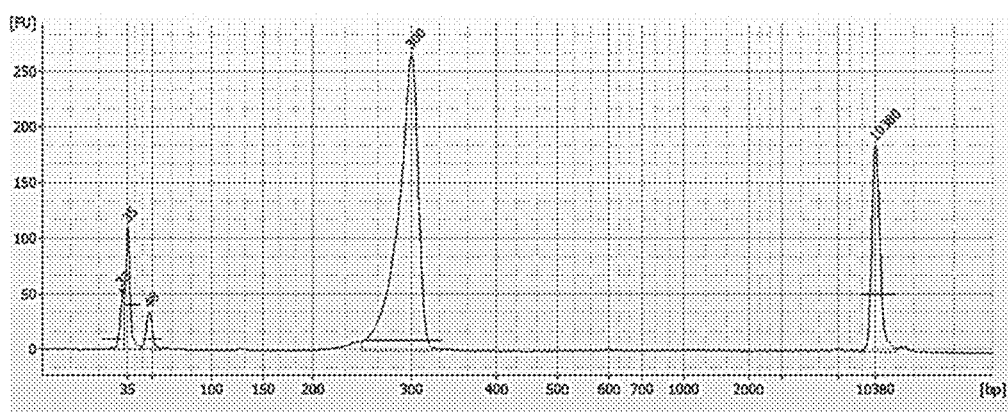
FIG. 21B illustrates the results of a method such as the one shown in FIG. 21A for making a library using multiplex amplification and treatment with resolvase to remove non-specific amplification products as described herein using 16000 pairs of long primers.
Figure 21A:
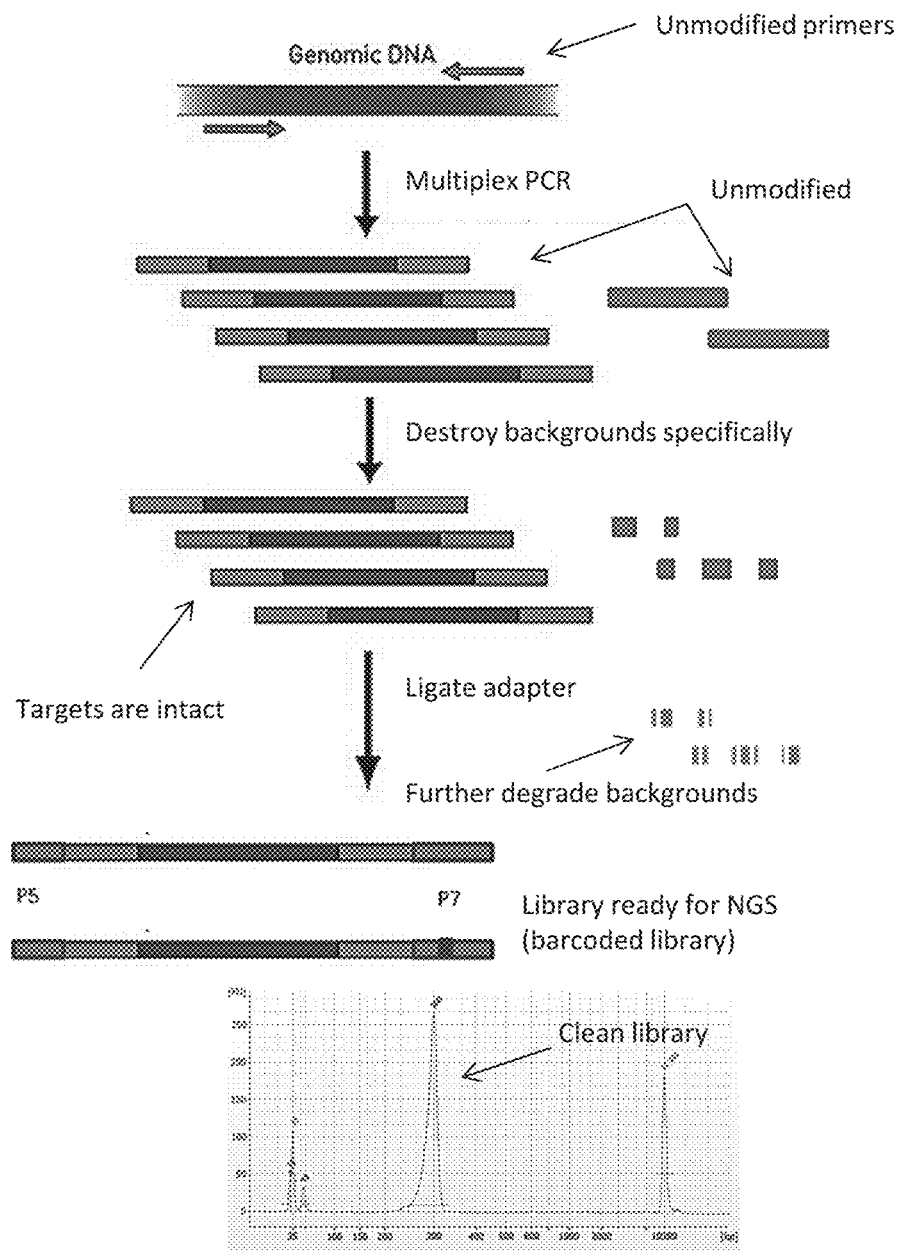
FIG. 21A schematically illustrates a method of making a library (e.g., for sequencing).

Any of the methods described herein may be used to generate a library; the library may be used for sequencing, for example. This is illustrated in FIGS. 3 and 21A. FIG. 3 is a schematic diagram of a procedure to remove non-specific amplification products generated in multiplex PCR and a library from the target amplicons. The procedure involves end repair of the ends of DNA fragments, cleavage of the no-specific products, adapter ligation, removal of unligated adapters and further amplification of the library.

In FIG. 3, a multiplex PCR is conducted with template DNA, unphosphorylated primers, dNTPs and a thermostable DNA polymerase. The number of pairs of primers can be any number from 7 to over 100,000 in a single reaction in a single tube or well. The products include target DNA fragments, i.e. the amplicons, and various non-specific products containing aberrant DNA structures. After PCR, the products are end-repaired by T4 DNA polymerase to make blunt-ends, then by T4 Polynucleotide kinase to phosphorylate 5'-ends, then by Taq polymerase to add an A to 3' ends in a buffer containing dATP. The products are then contacted with T4 endonuclease VII, which makes double-stranded breaks at or near aberrant DNA structures, while the target DNA fragments remain intact. Then the DNA mixture is ligated with adapters. The adapters contain three to six consecutive phosphorothioates at the 3' end of the sense-strand (indicated by *N3' in FIG. 3). When the DNA mixture is digested by *E. coli* exonuclease I and lambda exonuclease, the target DNA fragments are protected on both sides by the adapters, while all other DNA fragments are degraded into small oligonucleotides and nucleotides. The target DNA fragments can be used in various downstream applications with, or without, further purification to remove the debris of the non-specific products.

In more detail, the adapters are phosphorylated at the 5' end of the sense-strand. The 3' end of the antisense-strand contains an extra T, which allows T-A ligation with end-repaired PCR products.

In further detail, the ligation reaction includes T4 DNA ligase, and one of the following DNA ligases: 9° N™ DNA ligase, Taq DNA ligase, Tth DNA ligase, Tfi DNA ligase, Ampligase®, etc.

In further detail, after adapter-ligation and removal of non-specific products, the target DNA fragments may be further amplified by PCR.

Figure 4:
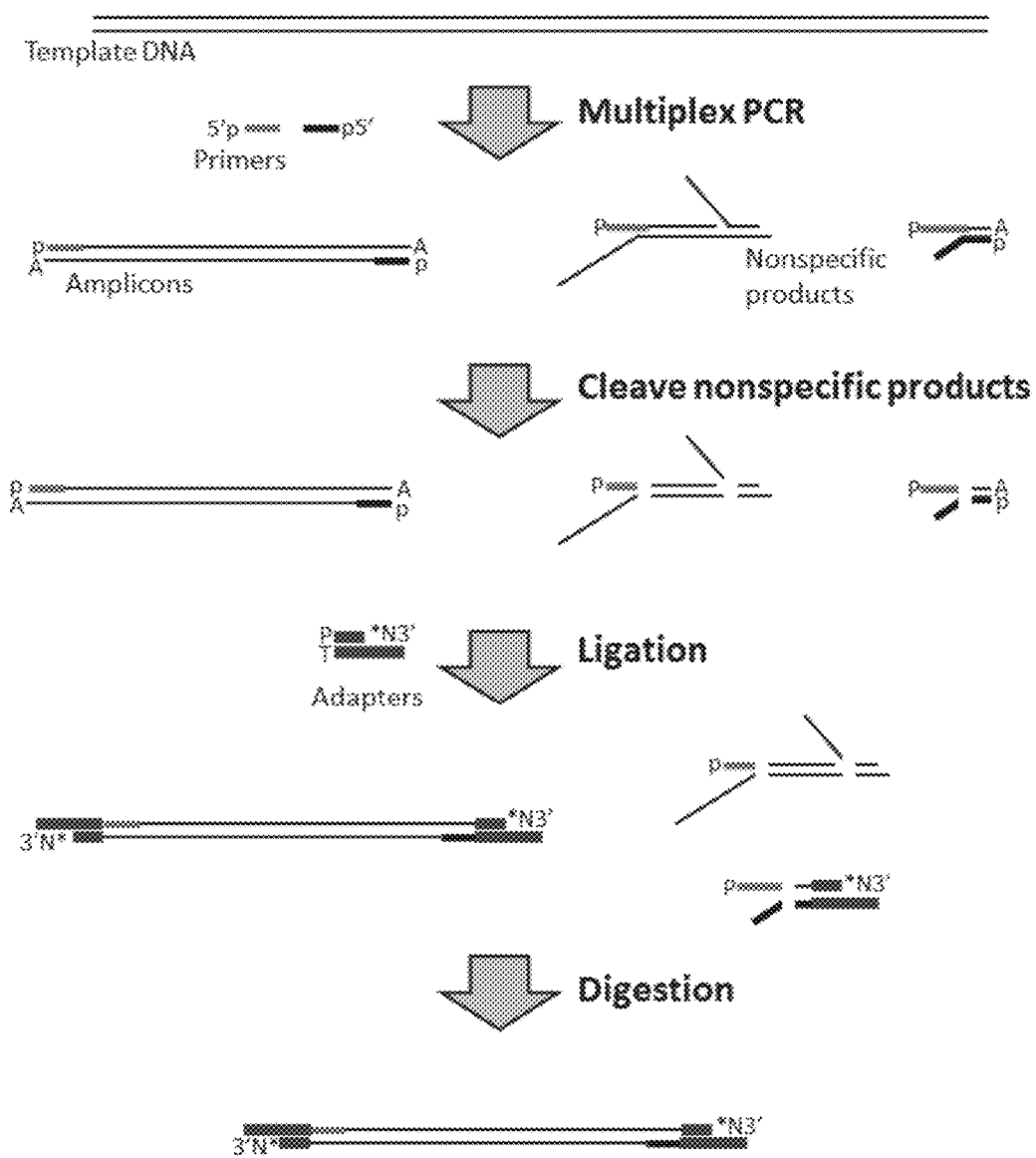
FIG. 4 shows another potential method to obtain target DNA fragments from a multiplex amplification reaction as described herein.

FIG. 4 is a schematic diagram of a prophetic procedure to remove non-specific amplification products generated in multiplex PCR and a library from the target amplicons. In this procedure, phosphorylated primers are used. The procedure involves end repair of the ends of DNA fragments, cleavage of the no-specific products, adapter ligation, removal of unligated adapters and further amplification of the library. In FIG. 4, phosphorylated primers are used in multiplex PCR. The PCR is conducted with template DNA, phosphorylated primers, dNTPs and a thermostable DNA polymerase. The number of pairs of primers can be any number from 7 to over 100,000 in a single reaction in a single tube or well. The products include target DNA fragments, i.e. the amplicons, and various non-specific products containing aberrant structures. The products are contacted with T4 endonuclease VII, which makes double-stranded breaks in the vicinity of aberrant DNA structures, while the target DNA fragments remain intact. Then the DNA mixture is ligated with adapters. The adapters contain three to six consecutive phosphorothioates at the 3' end of the sense-strand (indicated by *N3' in FIG. 4). When the DNA mixture is digested by *E. coli* exonuclease I and lambda exonuclease, the target DNA fragments are protected on both sides by the adapters, while all other DNA fragments are degraded into small oligonucleotides and nucleotides. The target DNA fragments can be used in various downstream applications with, or without, further purification to remove the debris of the non-specific products. In more detail, the adapters may be phosphorylated at the 5' end of the sense-strand. The 3' end of the antisense-strand contains an extra T, which allows T-A ligation with PCR products. In further detail, the ligation reaction may include T4 DNA ligase, and one of the following DNA ligases: 9° N™ DNA ligase, Taq DNA ligase, Tth DNA ligase, Tfi DNA ligase, Ampligase®, etc. After adapter-ligation and removal of non-specific products, the target DNA fragments may be further amplified by PCR.

Figure 5:
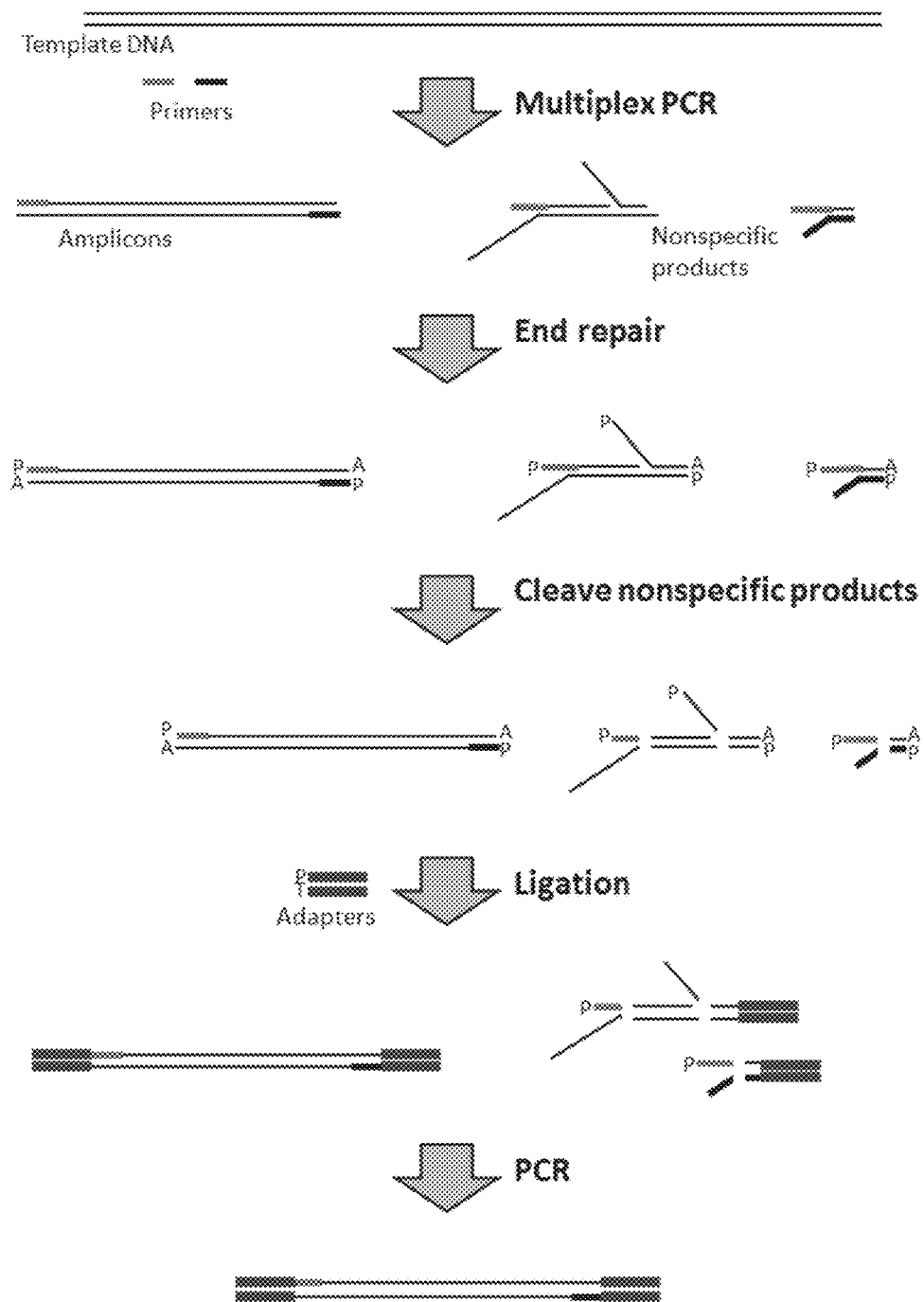
FIG. 5 illustrates an alternative method of the present disclosure to obtain target amplification products from multiplex amplification reaction.

FIG. 5 shows a schematic diagram of another variation of a procedure to remove non-specific amplification products generated in multiplex PCR and a library from the target amplicons. In this procedure, the unligated adapters are not removed by digestion. The procedure involves end repair of the ends of DNA fragments, cleavage of the no-specific products, adapter ligation and further amplification of the library. In FIG. 5, a multiplex PCR is conducted with template DNA, unphosphorylated primers, dNTPs and a thermostable DNA polymerase. The number of pairs of primers can be any number from 7 to over 100,000 in a single reaction in a single tube or well. The products include target DNA fragments, i.e. the amplicons, and various non-specific products containing aberrant structures. The products are end-repaired by T4 DNA polymerase to make blunt-ends, then by T4 Polynucleotide kinase to phosphorylate 5'-ends, then by Taq polymerase to add an A to 3' ends in a buffer containing dATP. The products are then contacted with T4 endonuclease VII, which makes double-stranded breaks in the vicinity of aberrant DNA structures, while the target DNA fragments remain intact. Then the DNA mixture is ligated with adapters. The ligated target DNA fragments are further amplified by PCR.

The adapters may be phosphorylated at the 5' end of the sense-strand. The 3' end of the antisense-strand contains an extra T, which allows T-A ligation with end-repaired PCR products. The adapters do not contain phosphorothioates. The ligation reaction may include T4 DNA ligase, and one of the following DNA ligases: 9° N™ DNA ligase, Taq DNA ligase, Tth DNA ligase, Tfi DNA ligase, Ampligase®, etc.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Example 1 is shown in FIG. 1, discussed briefly above, and shows a schematic diagram of multiplex PCR with template DNA, primers, dNTPs and a thermostable DNA polymerase.

Example 2

Example 2 is shown in FIG. 2 discussed above, and is a method of multiplex PCR with template DNA, primers, dNTPs and a thermophilic DNA polymerase.

Example 3

Example, 3, shown in FIG. 3 discussed briefly above, is a method of multiplex PCR with template DNA, unphosphorylated primers, dNTPs and a thermostable DNA polymerase.

Example 4

Example 4, shown in FIG. 4 discussed briefly above, is a method of multiplex PCR with phosphorylated primers used in multiplex PCR.

Example 5

Example 5, shown in FIG. 5 and discussed briefly above, is a schematic diagram of multiplex PCR with template DNA, unphosphorylated primers, dNTPs and a thermostable DNA polymerase.

Example 6

Optimization of Reaction Conditions

Figure 6A:
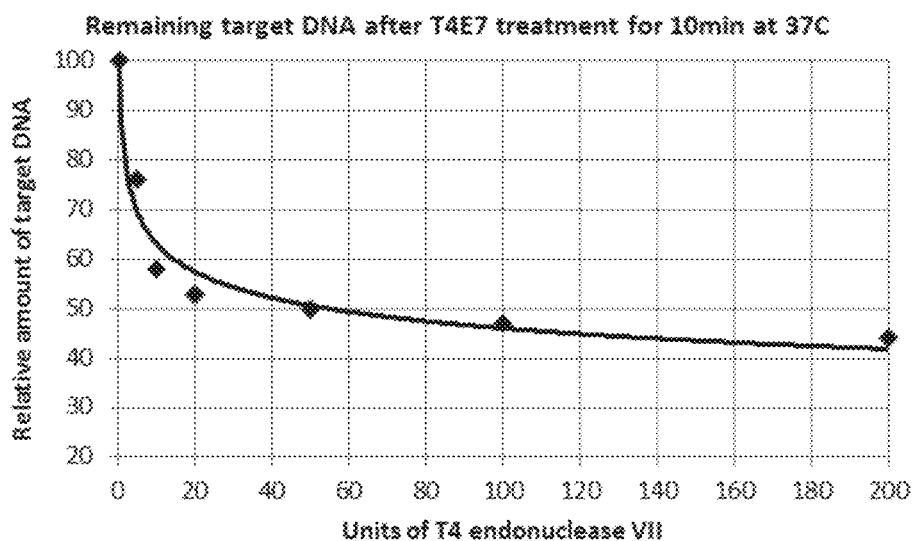
FIG. 6A is a graph showing the results of one example of titration of a resolvase (in this example T4 endonuclease VII) at various treatment parameters (e.g., units of resolvase for 10 min at 37° C.).
Figure 6B:
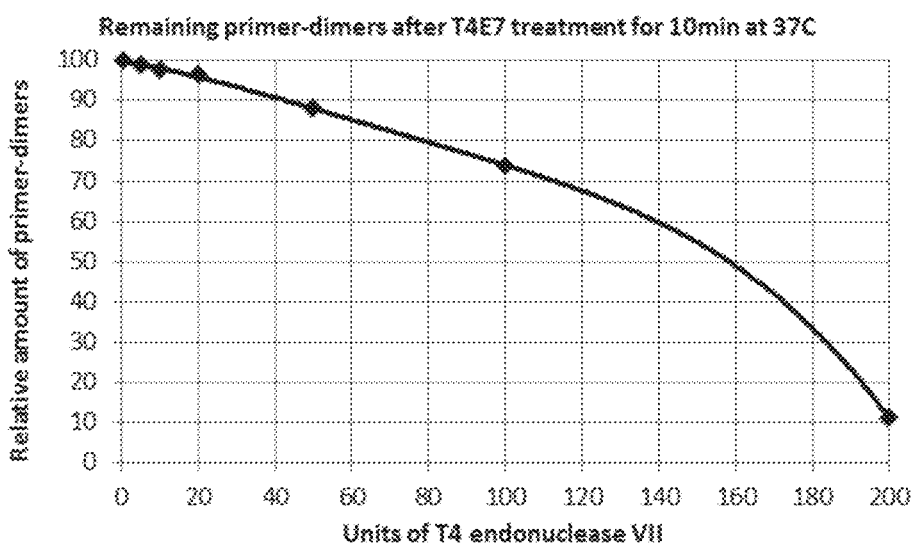
FIG. 6B is a graph showing the remaining amount of non-specific amplification products in a titration curve similar to that shown in FIG. 6A (where non-specific amplification products are referred to as "primer-dimers").
Figure 7A:
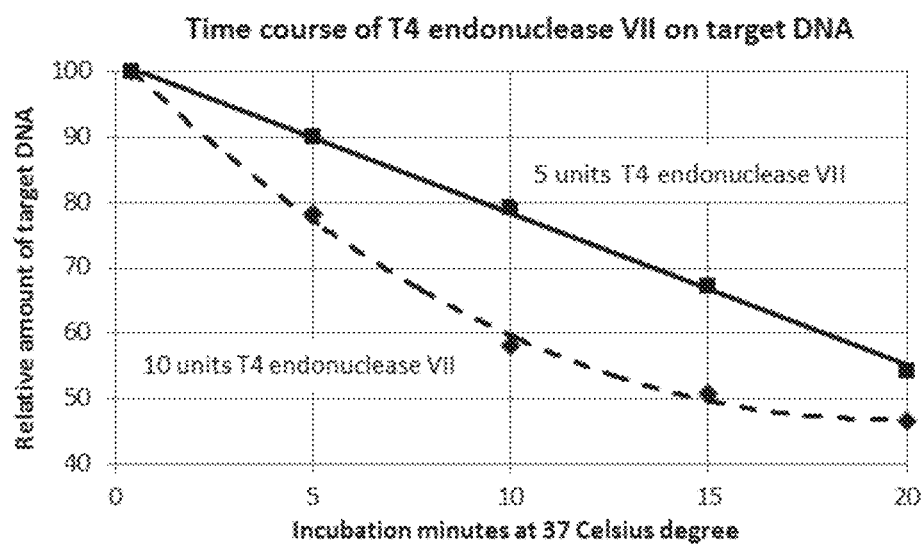
FIGS. 7A and 7B are graphs illustrating time courses of a resolvase (in this example, T4 endonuclease VII) at different treatment conditions (1 U, 5 U, 10 U, at 37° C.) which may be used to find the optimal condition to remove non-specific amplification products from a multiplexed amplification reaction mixture.
Figure 7B:
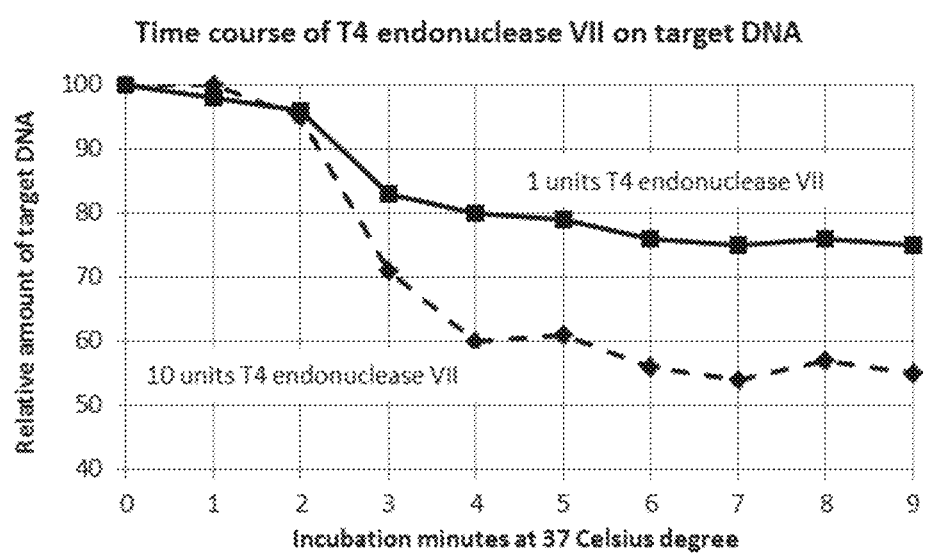

In any of the methods described herein, the resolvase conditions (concentration, buffer, incubation/treatment time and/or temperature) may be determined. General parameters for the use of resolvase to reduce non-specific amplification products from a template-dependent primer extension reaction while maintaining a substantial proportion of said plurality of target-specific amplification products are provided herein. For example, in general cleaving non-specific amplification products with the resolvase while maintaining a substantial proportion of target-specific amplification products may include exposing the non-specific amplification products and the plurality of target-specific amplification products to between about 0.2 U and 1000 U of resolvase, for between 0.5 minutes and 60 minutes, at between 16° C. and 37° C. FIGS. 6A-7B illustrate the determining of such ranges. FIGS. 6A and 6B illustrate titration of T4 endonuclease VII to find ranges of concentration that may be used to remove the non-specific amplification products in a multiplex PCR involving 207 pairs of primers. The effect of T4 endonuclease VII was assayed by either the quantity of remaining target DNA or the quantity of remaining primer-dimers. As described in greater detail below, a range of between about 0.5 and 20 (e.g., approximately 10 units) of T4 endonuclease VII was found sufficient. FIGS. 7A-7B show examples of time courses of T4 endonuclease VII to find the optimal durations to remove the non-specific amplification products in a multiplex PCR involving 207 pairs of primers. The effect of T4 endonuclease VII was assayed by either the quantity of remaining target DNA. Between about 0.5 minutes and 20 minutes (e.g., 5 minutes) of incubation was found to be sufficient.

While there are many enzymes that may cut DNA in the vicinity of aberrant DNA structures with various activity, T7 endonuclease I, T4 endonuclease VII and endonuclease V from *E. coli* and *T. maritima* are commercially available. Both T7 endonuclease I and T4 endonuclease VII are reported to have strong activities on various aberrant DNA structures. T7 endonuclease I produces 5' protruding ends of up to 6 nucleotides long while T4 endonuclease VII generating 3' protruding ends of the same length. These two endonucleases also have strong activity on single stranded DNA. They are functionally exchangeable. Endonuclease V is regarded as a DNA repair enzyme that recognizes deoxyinosine, a deamination product of deoxyadenosine in DNA, and often called deoxyinosine 3' endonuclease. Endonuclease V has weak activities on various aberrant DNA structures. All of these enzymes make random nicks on double-stranded DNA. Upon prolonged incubation with large amount of enzyme, double-stranded DNA will be gradually cut into small pieces of DNA fragments. For these reasons, T4 endonuclease VII was used in the following experiments, however other resolvases may be used and the methods, kits and compositions described herein are not limited to T4 endonuclease VII.

To find the optimal concentration of T4 endonuclease VII, we performed multiplex PCR and then used T4 endonuclease VII to treat the amplification products. The small DNA fragments were removed through one round of purification with magnetic beads. The resulting DNA was assayed with a high sensitivity chip of BioAnalyzer.

The primer panel of Ion AmpliSeq™ hotspot cancer panel v2 (Life Technologies, catalog number 4475346) was used in multiplex PCR. This primer panel covers approximately 2,800 COSMIC mutations from 50 oncogenes and tumor suppressor genes. It has 207 primer pairs in one pool. The multiplex PCR reactions were done in 104 The following components were added to each of a 0.2 ml thin wall PCR tube (Thomas Scientific, Snapstrip II natural 0.2 ml PCR strip tube, catalog number 1228F73): 5 µl of the 2-fold concentrated primer pool, 1 µl 10×PCR buffer (1×PCR buffer: 50 mM TrisHCl, pH8.3, 50 mM KCl, 5 mM $MgCl_2$, 0.2 mM dNTP each), 2 µl Omni KlenTaq DNA polymerase (4.2 units/µl) (Enzymatics, P7500-LC-F), 1 µl of 10 ng/µl of human DNA (Coriell Institute, NA12878), and 1 µl distilled water.

The 0.2 ml thin wall PCR tubes were capped with the attached caps, vortexed brief for 3 seconds and spun in a mini centrifuge (Pipette.com, MyFuge 12 place mini centrifuge, catalog number C1012) for 3 seconds. No mineral oil was required to cover the PCR reaction mixture. The tubes were placed in a thermos cycler (GeneAmp® PCR system 9700 96-well gold plated, Life Technologies, catalog number 4314878).

The PCR was initially held at 98° C. for 2 minutes, followed by 17 cycles of denaturing at 98° C. for 15 seconds and annealing and synthesizing at 60° C. for 4 min. After cycling, the reactions were held at 10° C. until proceeding to the next step.

After PCR, the following components were added directly to the above reactions: 10 μl 2× Digestion buffer (50 mM Tris-HCl, pH 8.0, 15 mM $MgCl_2$, 20 mM beta mercaptoethanol), 1 μl T4 endonuclease VII (Affymetrix, part number 78300 50KU), 18 ul distilled water. Reactions were incubated at 37° C. for 10 min.

After the incubation, reaction was stopped with 1 ul 0.5M EDTA. The DNA was purified once with 1.6×MagSi-NG-Sprep beads. The paramagnetic beads were from Amsbio LLC (Amsbio LLC, MagSi-NGSprep, catalog number MD61021). The MagSi-NGSprep beads were suspended thoroughly in the container by vortexing, then 64 μl of MagSi-NGSprep beads, representing 1.6-fold of the volume of the amplified and combined amplicons, was added into the tube containing the amplified amplicons. The tube was mixed by vortexing for 5 seconds and incubated at room temperature for 5 minutes. Then the tube was spun in a mini centrifuge for 3 seconds, and placed on a magnetic rack to capture the beads for 2 minutes. The magnet inside magnetic rack was from KJ Magnetics (KJ Magnetics, catalog number D4X0DIA-N52). Once the solution cleared, the supernatant was carefully pipetted out and discarded without disturbing the bead pellet. Without removing the tube from the magnetic rack, 1500 freshly made 70% ethanol was added into the tube. The tube was then rotated 180 degree on the magnet rack, allowing the bead pellets to detach from one side of the inner wall of each tube, and pellet on the opposite side. Once the solution cleared, the supernatant was carefully pipetted out and discarded without disturbing the bead pellet. The beads were washed with 70% ethanol in this way for a total of 2 times. After pipetting out the 70% ethanol in the final wash, the tube was spun in a mini centrifuge for 3 seconds. Any remaining ethanol droplets inside the tube were pipetted out without disturbing the bead pellets. The bead pellets were air-dried for 3 minutes at room temperature on the magnet rack with tube cap open. Finally, the tube was removed from the magnetic rack and 40 μl distilled water was added into the tube. The tube was vortexed vigorously for 5 seconds to resuspend the beads into distilled water, spun in a mini centrifuge for 3 seconds, and placed in the magnetic rack for 2 minutes. After the solution cleared, the supernatant containing the eluted DNA fragments were transferred into a fresh tube. The DNA fragments were purified with 1.6×MagSi-NGSprep beads by this method in a total of two times. After the final purification, the DNA fragments were eluted in 5 μl distilled water, and assayed in the following step.

The size, concentration and purity of the DNA fragments were assayed in a 2100 BioAnalyzer instrument (Agilent Technologies, catalog number G2938B). 1 μl of the purified DNA fragments obtained in the previous step was assayed with a high sensitivity DNA analysis kit (Agilent Technologies, catalog number 5067-4626), according to the methods provided by the supplier. As mentioned above, FIG. 6A shows the remaining target DNA treated by 0-200 units of T4 endonuclease VII (also referred to as T4E7) in 10 min at 37° C. The remaining target DNA refers to the PCR products with the expected sizes. We saw double-stranded DNA is degraded with higher concentrations of T4 endonuclease VII. This may also indicate that the non-specific products with similar sizes were removed by the enzyme, leaving the target DNA behind.

FIG. 6B shows the remaining Primer-dimer by 0-200 units of T4E7 T4 endonulcease VII in 10 min at 37 C. The amount of non-specific amplification products was reduced. In addition, we saw the sizes of non-specific amplification products were shifted smaller by assaying with BioAnalyzer, indicating they were cut by T4 endonuclease VII at least once. These will facilitate the removal of these fragments by further approaches such as selective digestion and/or a further round of polymerase chain reaction.

Since the non-specific amplification products can be removed after being cut once, the above results indicate that limited activity of T4 endonuclease VII is sufficient. This can preserve the target DNA while removing nonspecific amplification products.

Multiplex PCR was done as described above. After PCR, the following components were added directly to the above reactions: 10 μl 2× Digestion buffer (50 mM Tris-HCl, pH 8.0, 15 mM $MgCl_2$, 20 mM beta mercaptoethanol), 1 μl T4 endonuclease VII (Affymetrix, part number 78300 50KU), 18 ul distilled water. The reactions were incubated at 37° C. for various time periods. After incubation, the reactions were stopped and DNA was purified and assayed in BioAnalyzer, as described in above.

In the first experiment, the effect of T4 endonuclease VII was assayed up to 20 minutes in 5 minute intervals (FIG. 7A). We saw gradual reduction of target DNA with low concentration (5 units) of T4 endonuclease VII, and sharp reduction of target DNA at 10 units of T4 endonuclease VII. In the second experiment, the effect of T4 endonuclease VII was assayed up to 9 minutes in 1 minute intervals (FIG. 7B). This titration found 10 units of T4 endonuclease VII in 5 min at 37° C. is sufficient to remove the non-specific amplification products.

Figure 8A:
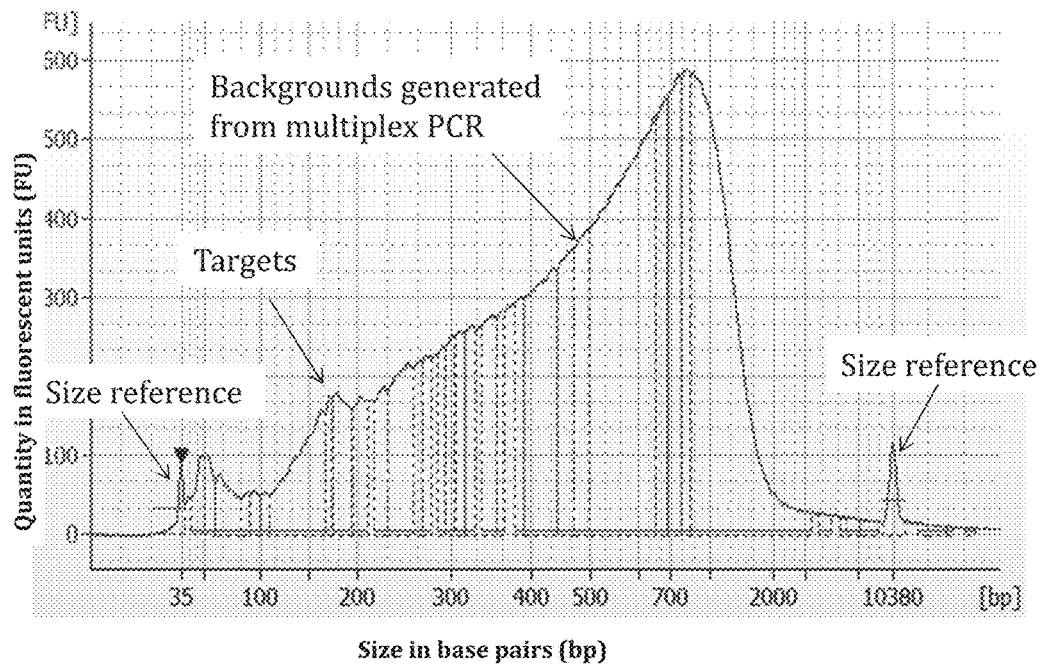
FIG. 8A illustrates one example a multiplex amplification reaction showing a typical background resulting from non-specific amplification products. In this example, the non-specific amplification products overwhelm the desired specific amplification products ("targets").

FIG. 8A illustrates an exemplary multiplex amplification reaction showing a typical background resulting from non-specific amplification products. The target-specific amplification products in this example are virtually swamped out by the non-specific amplification products ("background generated from multiplex PCR") between the size markers, based on the graph showing the relative florescent intensity (quantity in florescence units, FU) for size in base pairs (bp).

Example 7

Figure 8B:
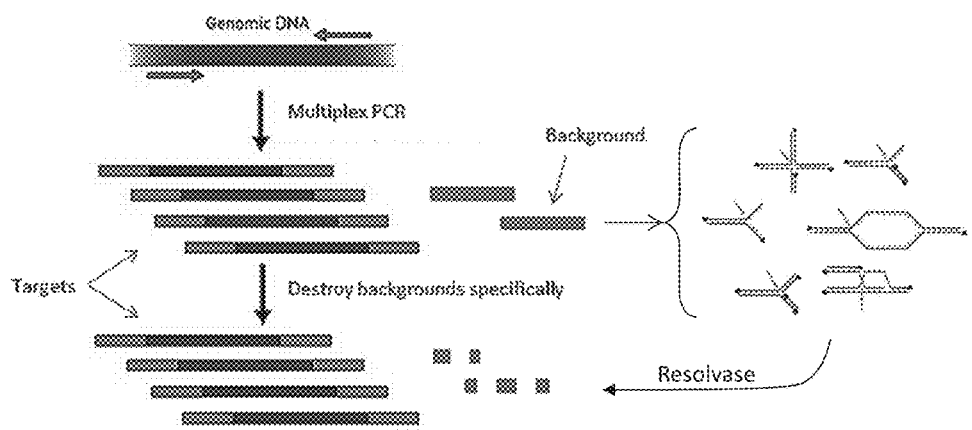
FIG. 8B schematically illustrates the method of reducing non-specific amplification products from a template-dependent primer extension reaction by treating with a Resolvase (e.g., T4 endonuclease VII) to selectively remove the non-specific amplification products by cutting aberrant sites in the non-specific amplification products.

FIG. 8B, similar to the methods exemplified in FIGS. 1 and 3-5, illustrate the use of a resolvase (such as T4 endonuclease VII) to reduce the non-specific amplification product and reveal the target-specific amplification products in a multiplex amplification procedure. In FIG. 8B, the resolvase targets the background, non-specific amplification products which are hypothesized to have one or more aberrant polynucleotide structures, as shown (e.g., Holliday structures or junctions, branched DNAs, Y-structures, cruciforms, hetereoduplex loops, bulky adducts, single-stranded overhangs, DNA mismatches, or non-perfectly-matched DNAs).

Figure 8C:
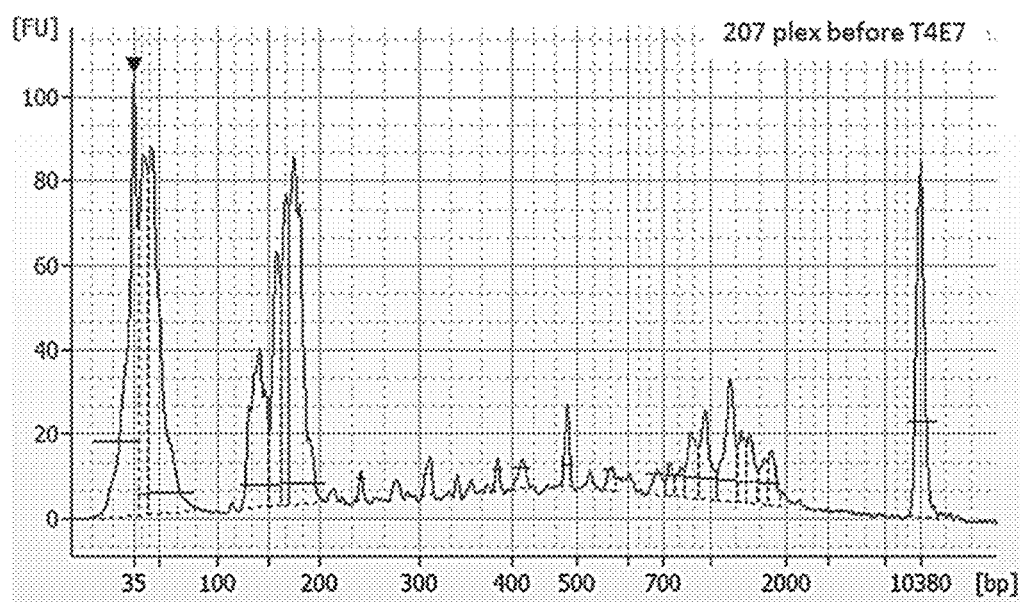
FIGS. 8C and 8D show an example illustrating the effectiveness of the method of reducing non-specific amplification products by treating with a resolvase to selectively remove the non-specific amplification products.
Figure 8D:
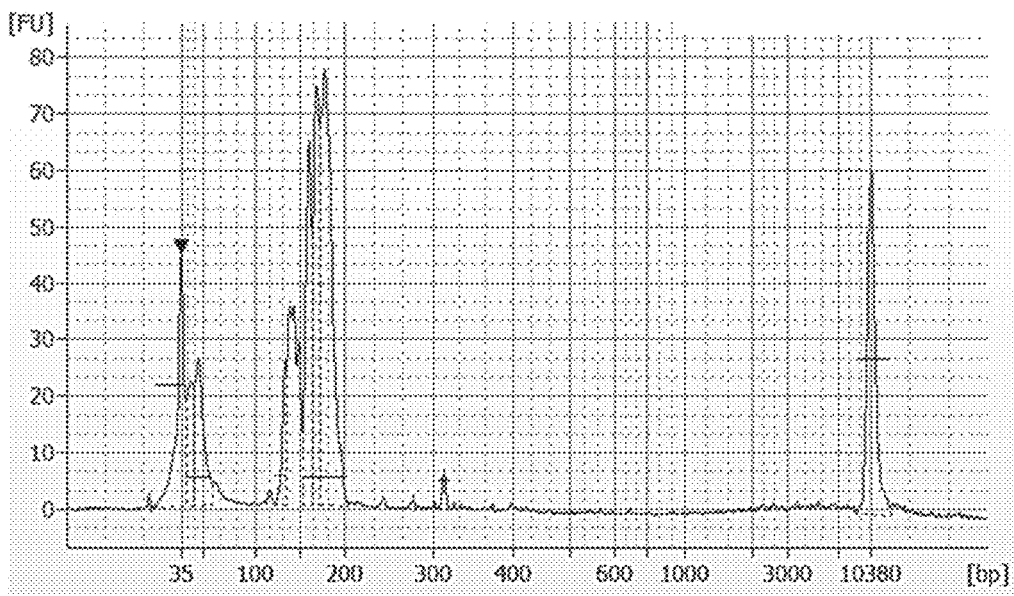

FIGS. 8C and 8D illustrate a working example of this method. The primer panel of Ion AmpliSeg™ hotspot cancer panel v2 (Life Technologies, catalog number 4475346) was used in multiplex PCR. This primer panel covers approximately 2,800 COSMIC mutations from 50 oncogenes and tumor suppressor genes. It has 207 primer pairs in one pool. The multiplex PCR reaction was done in 104 The following components were added to each of a 0.2 ml thin wall PCR tube (Thosmas Scientific, Snapstrip II natural 0.2 ml PCR strip tube, catalog number 1228F73): 5 μl of the 2-fold concentrated primer pool, 1 μl 10×PCR buffer (1×PCR buffer: 50 mM TrisHCl, pH8.3, 50 mM KCl, 5 mM $MgCl_2$, 0.2 mM dNTP each), 2 μl Omni KlenTaq DNA polymerase (4.2 units/µl) (Enzymatics, P7500-LC-F), 1 µl of 10 ng/µl of human DNA (Coriell Institute, NA12878), and 1 µl distilled water.

The 0.2 ml thin wall PCR tubes were capped with the attached caps, vortexed brief for 3 seconds and spun in a mini centrifuge (Pipette.com, MyFuge 12 place mini centrifuge, catalog number C1012) for 3 seconds. No mineral oil was required to cover the PCR reaction mixture. The tubes were placed in a thermos cycler (GeneAmp® PCR system 9700 96-well gold plated, Life Technologies, catalog number 4314878).

The PCR was initially held at 98° C. for 2 minutes, followed by 15 cycles of denaturing at 98° C. for 15 seconds and annealing and synthesizing at 60° C. for 4 min. After cycling, the reactions were held at 10° C. until proceeding to the next step.

After PCR, the following components were added directly to the above reactions: 0 µl 2× Digestion buffer (50 mM Tris-HCl, pH 8.0, 15 mM MgCl$_2$, 20 mM beta mercaptoethanol), 1 µl T4 endonuclease VII (Affymetrix, part number 78300 50KU), 18 ul distilled water. Reactions were incubated at 37° C. for 10 min.

After the reaction, the DNA was purified once with 1.6×MagSi-NGSprep beads. The paramagnetic beads were from Amsbio LLC (Amsbio LLC, MagSi-NGSprep, catalog number MD61021). The MagSi-NGSprep beads were suspended thoroughly in the container by vortexing, then 64 µl of MagSi-NGSprep beads, representing 1.6-fold of the volume of the amplified and combined amplicons, was added into the tube containing the amplified amplicons. The tube was mixed by vortexing for 5 seconds and incubated at room temperature for 5 minutes. Then the tube was spun in a mini centrifuge for 3 seconds, and placed on a magnetic rack to capture the beads for 2 minutes. The magnet inside magnetic rack was from KJ Magnetics (KJ Magnetics, catalog number D4X0DIA-N52). Once the solution cleared, the supernatant was carefully pipetted out and discarded without disturbing the bead pellet. Without removing the tube from the magnetic rack, 150 µl freshly made 70% ethanol was added into the tube. The tube was then rotated 180 degree on the magnet rack, allowing the bead pellets to detach from one side of the inner wall of each tube, and pellet on the opposite side. Once the solution cleared, the supernatant was carefully pipetted out and discarded without disturbing the bead pellet. The beads were washed with 70% ethanol in this way for a total of 2 times. After pipetting out the 70% ethanol in the final wash, the tube was spun in a mini centrifuge for 3 seconds. Any remaining ethanol droplets inside the tube were pipetted out without disturbing the bead pellets. The bead pellets were air-dried for 3 minutes at room temperature on the magnet rack with tube cap open. Finally, the tube was removed from the magnetic rack and 40 µl distilled water was added into the tube. The tube was vortexed vigorously for 5 seconds to resuspend the beads into distilled water, spun in a mini centrifuge for 3 seconds, and placed in the magnetic rack for 2 minutes. After the solution cleared, the supernatant containing the eluted DNA fragments were transferred into a fresh tube. The DNA fragments were purified with 1.6×MagSi-NGSprep beads by this method in a total of two times. After the final purification, the DNA fragments were eluted in 5 µl distilled water, and assayed in the following step.

The size, concentration and purity of the DNA fragments were assayed in a 2100 BioAnalyzer instrument (Agilent Technologies, catalog number G2938B). 1 µl of the purified DNA fragments obtained in the previous step was assayed with a high sensitivity DNA analysis kit (Agilent Technologies, catalog number 5067-4626), according to the methods provided by the supplier. The results are presented in FIGS. 8C and 8D. FIG. 8C shows the presence of target amplicons and non-specific amplification products before digestion by T4 endonuclease VII. The non-specific amplification products are from 200 bp to over 2000 bp. The peaks from 100 bp to 200 bp were target DNA fragments. FIG. 8D shoes the effect after digestion with T4 endonuclease VII. The non-specific amplification products from 200 bp to over 2000 bp were removed by T4 endonuclease digestion and the subsequent purification.

Example 8

Figure 9A:
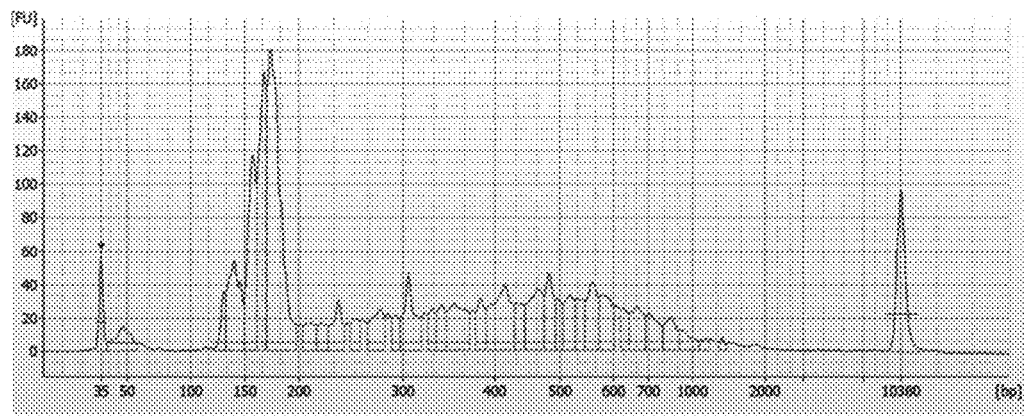
FIGS. 9A and 9B show another example of removal of non-specific amplification products generated in multiplex amplification reaction with 207 pairs of long primers.
Figure 9B:
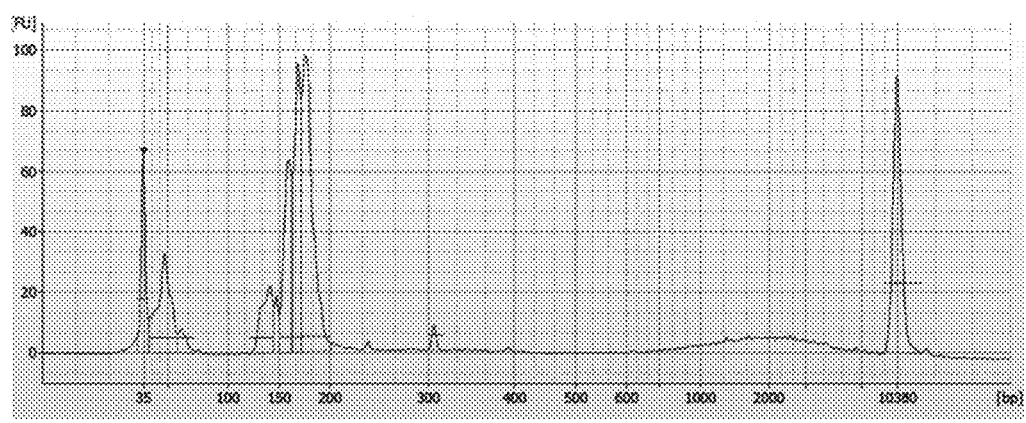
Figures 10A, 10B, 10C, 10D, 10E, 10F:
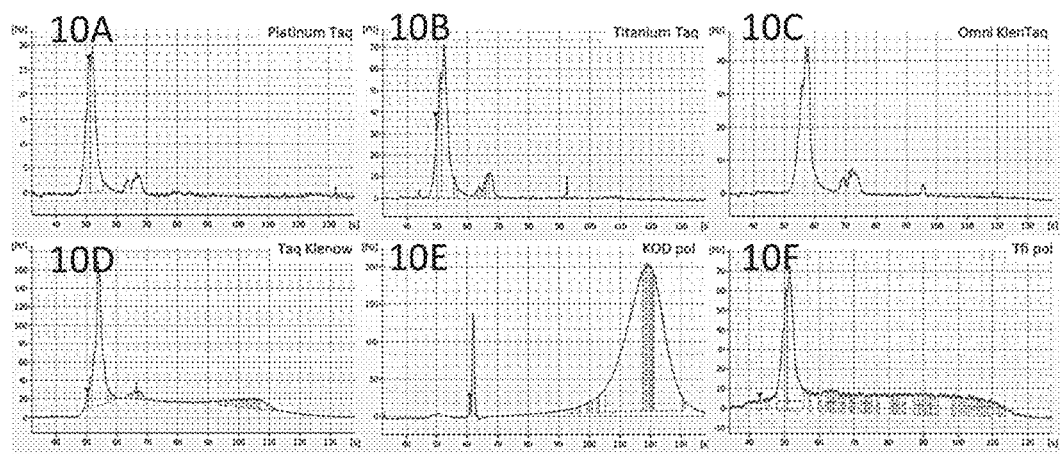
FIGS. 10A-10F illustrate the use of various DNA polymerases with the methods described herein for removing non-specific amplification products from multiplex amplification reaction (in this example, using 207 pairs of primers).

A similar reduction in non-specific amplification products may be seen in a multiplex PCR with 207 pairs of long primers, as shown in FIGS. 9A-9B. In this example, the primer panel was identical to that of Ion AmpliSeq™ hotspot cancer panel v2 (Life Technologies, catalog number 4475346), except that 5'CCTACACGACGCTCTTC-CGATCT3' (SEQ ID NO: 1) was added to the 5' end of each forward primer, and 5'TTCAGACGTGTGCTCTTC-CGATCT3' (SEQ ID NO: 2) was added to 5' end of each reverse primer. These "long" primers allow easy addition of adapters onto amplicons by an additional round of PCR.

The methods of doing multiplex PCR and the subsequent treatments and assays were identical to those in EXAMPLE 7, above. The results are presented in FIGS. 9A-9B. FIG. 9A shows the result of multiplex PCR with long primers before digestion with T4 endonuclease VII. FIG. 9B shows the removal of non-specific amplification products through digestion with T4 endonuclease VII.

Example 9

Polymerase in Multiplex PCR

In general, any appropriate polymerase may be used to perform the amplification (multiplex amplification) described herein. The methods, compositions and kits described herein are compatible with a variety of enzymes. FIGS. 10A-10F illustrate the use of various polymerase enzymes in multiplex PCR. In each example, multiplex PCR was done as described in EXAMPLE 6 above except that 5 units of Platinum taq (FIG. 10A), Titanium taq (FIG. 10B), Omni Klen taq (FIG. 10C), Taq Klenow (FIG. 10D), KOD DNA polymerase (FIG. 10E) and Tfi DNA polymerase (FIG. 10F) were used in each multiplex PCR reaction. After PCR, the following components were added directly to the above reactions: 10 µl 2× Digestion buffer (50 mM Tris-HCl, pH 8.0, 15 mM MgCl$_2$, 20 mM beta mercaptoethanol), 1 µl T4 endonuclease VII (Affymetrix, part number 78300 50KU), 18 ul distilled water. Reactions were incubated at 37° C. for 5 minutes. After incubation, the reactions were stopped with 0.5 M EDTA. The DNA was purified and assayed in BioAnalyzer, as described in EXAMPLE 6. The results show that Platinum taq, Titanium taq and Omni Klen taq produced comparable yields of target amplicons, while Taq Klenow, KOD DNA polymerase and Tfi DNA polymerase produced extraordinarily high amounts non-specific amplification products. In this example, the Platinum taq, Titanium taq and Omni Klen taq may be preferable for multiplex PCR.

Example 10

Figure 11:
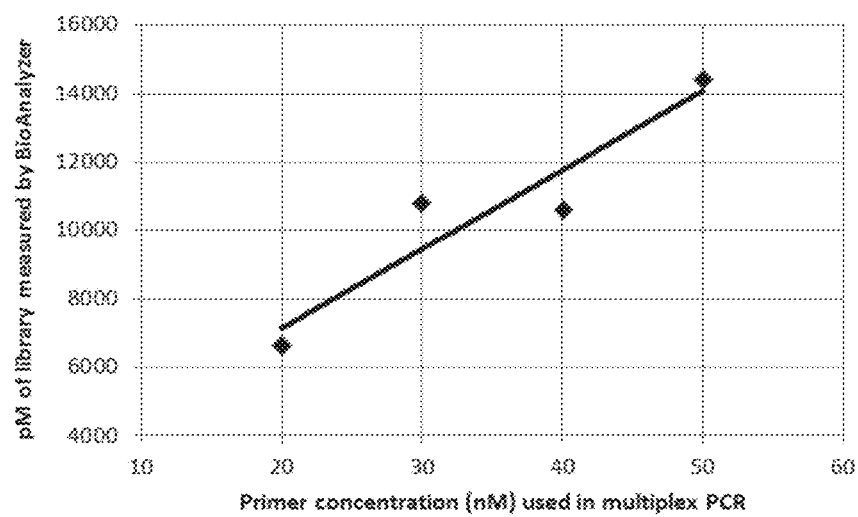
FIG. 11 is a graph illustrating the effect of increasing the overall concentration of primer pairs on the overall yield of target amplicon showing that higher overall concentration resulted in higher yields while still being effectively treated by the methods for removing the non-specific amplification products as described herein. In this example, 207 pairs of primers were used.

The primer concentration in multiplex PCR may be titrated. In this example, Multiplex PCR was done as described in EXAMPLE 6 except that 20, 30, 40, 50 nM of 207 pairs of primers were used in each multiplex PCR reaction. After PCR, the following components were added directly to the above reactions: 10 µl 2× Digestion buffer (50 mM Tris-HCl, pH 8.0, 15 mM $MgCl_2$, 20 mM beta mercaptoethanol), 1 µl T4 endonuclease VII (Affymetrix, part number 78300 50KU), 18 ul distilled water. Reactions were incubated at 37° C. for 5 minutes. After incubation, the reactions were stopped with 0.5 M EDTA. The DNA was purified and assayed in BioAnalyzer, as described in EXAMPLE 6. The results are presented in FIG. 11. This experiment showed that high concentration of primers leads to higher yield of the target amplicons.

Example 11

Figure 12:
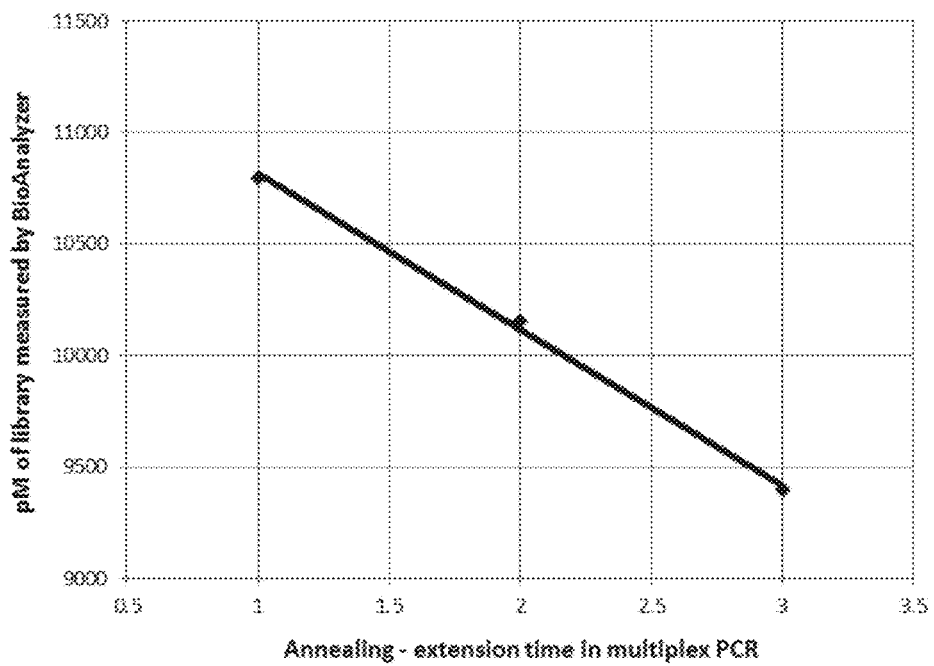
FIG. 12 is a graph illustrating the effect of annealing and extension duration for multiplex amplification (again using 207 pairs of primers) with the methods for removing the non-specific amplification products as described herein.

The annealing and extension time of multiplex PCR may also be adjusted to optimize the effects described herein, as shown in FIG. 12. In this example, Multiplex PCR was done as described in EXAMPLE 6 except that 1, 2, 3 minutes of annealing and extension time were used in each multiplex PCR reaction. After PCR, the following components were added directly to the above reactions: 10 µ2× Digestion buffer (50 mM Tris-HCl, pH 8.0, 15 mM $MgCl_2$, 20 mM beta mercaptoethanol), 1 µl T4 endonuclease VII (Affymetrix, part number 78300 50KU), 18 ul distilled water. Reactions were incubated at 37° C. for 5 minutes. After incubation, the reactions were stopped with 0.5 M EDTA. The DNA was purified and assayed in BioAnalyzer, as described in EXAMPLE 6. The results are presented in FIG. 12. This experiment showed that 1 minute of annealing and extension leads to higher yield of the target amplicons.

Example 12

Figure 13:
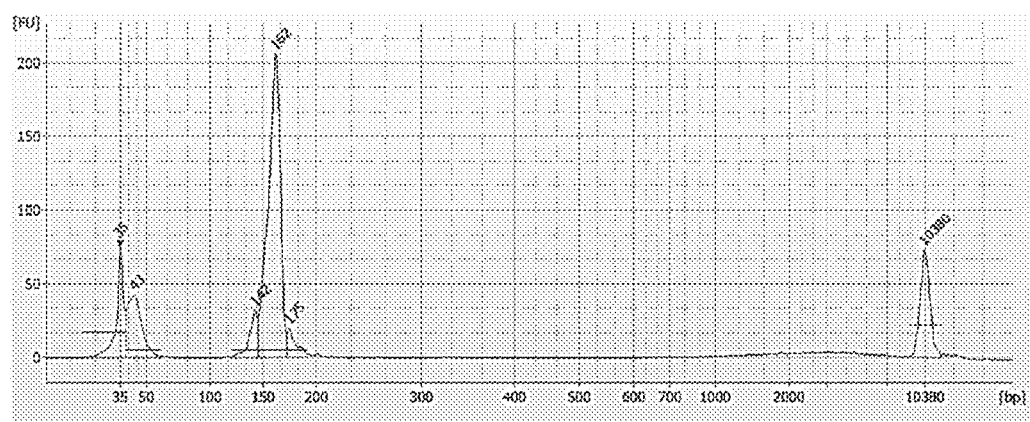
FIG. 13 illustrates an example of the method for removing the non-specific amplification products as described herein in a multiplex amplification reaction (PCR) involving 2915 pairs of primers.

As mentioned above, a large number of primer pairs may be used in the methods described herein and still result in substantial reduction of non-specific amplification products. For example, FIG. 13 illustrates the removal of non-specific amplification products in a multiplex PCR involving 2915 pairs of primers.

The primer panel was Qiagen GeneRead DNAseq human breast cancer panel (Qiagen, catalog number NGHS-001X-12). This panel covers 44 genes of 268621 target bases, with 2915 pairs of primers, and divided in 4 pools, with each pool containing approximately 730 primer pairs. This panel has reported coverage of 98.2% at 20× median sequencing depth, 96.8% specificity. 91% uniformity. There is no uracil nucleotide or any other modification of bases in each primer of this panel. This primer panel is in 2-fold concentrated. Therefore, 4 PCR reactions were performed with each of the 4 pools of primers, and 50% of the total PCR volume in each reaction was each of the 4 pools.

Each of the multiplex PCR reactions was done in 10 µl. The following components were added to each of a 0.2 ml thin wall PCR tube (Thomas Scientific, Snapstrip II natural 0.2 ml PCR strip tube, catalog number 1228F73): 5 µl of the 2-fold concentrated primer pool, 1 µl 10×PCR buffer (1×PCR buffer: 50 mM TrisHCl, pH8.3, 50 mM KCl, 5 mM $MgCl_2$, 0.8 mM dNTP each), 2 µl Omni KlenTaq DNA polymerase (4.2 units/µl) (Enzymatics, P7500-LC-F), 1 µl of 10 ng/µl of human DNA (Coriell Institute, NA12878), and 1 µl distilled water. There were 4 multiplex PCR reactions for the Qiagen GeneRead DNAseq human breast cancer panel.

The 0.2 ml thin wall PCR tubes were capped with the attached caps, vortexed brief for 3 seconds and spun in a mini centrifuge (Pipette.com, MyFuge 12 place mini centrifuge, catalog number C1012) for 3 seconds. No mineral oil was required to cover the PCR reaction mixture. The tubes were placed in a thermos cycler (GeneAmp® PCR system 9700 96-well gold plated, Life Technologies, catalog number 4314878). The following two temperature profiles were performed for each of the primer panel.

For Qiagen GeneRead DNAseq human breast cancer panel, the PCR was initially held at 98° C. for 2 minutes, followed by 15 cycles of denaturing at 98° C. for 15 seconds and annealing and synthesizing at 60° C. for 4 minutes. After cycling, the reactions were held at 10° C. until proceeding to the next step.

After incubation, the reaction mixture proceeded directly to this step without changing buffer. The following components were added directly to each of the above reactions: 40 µl 2× Digestion buffer (50 mM Tris-HCl, pH 8.0, 15 mM $MgCl_2$, 20 mM beta mercaptoethanol), 4 µl T4 endonuclease VII (Affymetrix, part number 78300 50KU), 18 ul distilled water. Reactions were incubated at 37° C. for 5 minutes.

After the incubation, the reactions were stopped with 0.5M EDTA. The DNA was purified once with 1.6×MagSi-NGSprep beads. The MagSi-NGSprep beads were suspended thoroughly in the container by vortexing, 128 µl of MagSi-NGSprep beads was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 150 µl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 5 µl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, and assayed in the following step.

The size, concentration and purity of the DNA fragments were assayed in a 2100 BioAnalyzer instrument (Agilent Technologies, catalog number G2938B). 1 µl of the purified DNA fragments obtained in the previous step was assayed with a high sensitivity DNA analysis kit (Agilent Technologies, catalog number 5067-4626), according to the methods provided by the supplier. The results are presented in FIG. 13.

Example 13

Figure 14:
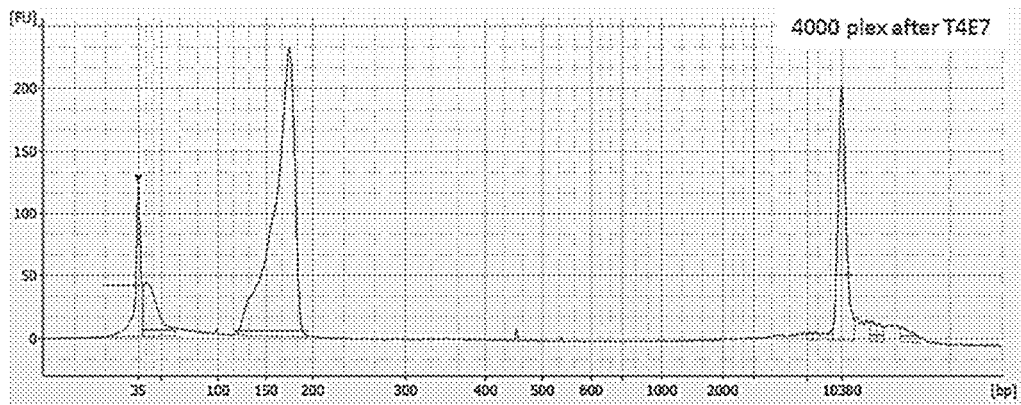
FIG. 14 is another example of the method for removing the non-specific amplification products as described herein in a multiplex amplification reaction (e.g., PCR) involving 16000 pairs of primers.

FIG. 14 illustrates an example of removing no-specific amplification products in a multiplex PCR involving 16000 pairs of primers. In this example, the primer panel was Ion AmpliSeq™ comprehensive cancer panel (Life Technologies, catalog number 4477685). This primer panel covers all-exons of 409 key tumor suppressor genes and oncogenes that are frequently mutated and cited in scientific publications. This has 16000 primer pairs in 4 pools; each pool has approximately 4,000 primer pairs. The lengths of the amplicons range from 125-175 base pairs, the target region covers approximately 1.73 million bases. When libraries was made with this panel and Life Technologies' Ion AmpliSeq™ Library Kit 2.0, and sequenced in Life Technologies' Ion PGM™ system, this panel has reported coverage of 94% at >20% median sequencing depth, with on target bases (bases mapped to target regions, out of total mapped bases per run) of 97%. In multiplex PCR, each of the 4 primer pools requires 10 ng of human genomic DNA as template, total of 40 ng to cover the entire panel. There is at least one uracil nucleotide in each primer of this primer panel. This primer panel is in 2-fold concentrated. Therefore, 4 PCR reactions were performed with each of the 4 pools of primers.

Each of the multiplex PCR reactions was done in 10 µl. The following components were added to each of a 0.2 ml thin wall PCR tube (Thomas Scientific, Snapstrip II natural 0.2 ml PCR strip tube, catalog number 1228F73): 5 µl of the 2-fold concentrated primer pool, 1 µl 10×PCR buffer (1×PCR buffer: 50 mM TrisHCl, pH8.3, 50 mM KCl, 5 mM $MgCl_2$, 0.8 mM dNTP each), 20 Omni KlenTaq DNA polymerase (4.2 units/µl) (Enzymatics, P7500-LC-F), 1 µl of 10 ng/µl of human DNA (Coriell Institute, NA12878), and 10 distilled water. There were 4 multiplex PCR reactions for the Ion AmpliSeq™ comprehensive cancer panel and 4 multiplex PCR reactions for the Qiagen GeneRead DNAseq human breast cancer panel.

The 0.2 ml thin wall PCR tubes were capped with the attached caps, vortexed brief for 3 seconds and spun in a mini centrifuge (Pipette.com, MyFuge 12 place mini centrifuge, catalog number C1012) for 3 seconds. No mineral oil was required to cover the PCR reaction mixture. The tubes were placed in a thermos cycler (GeneAmp® PCR system 9700 96-well gold plated, Life Technologies, catalog number 4314878). The following two temperature profiles were performed for each of the primer panel.

The PCR was initially held at 98° C. for 2 minutes, followed by 13 cycles of denaturing at 98° C. for 15 seconds and annealing and synthesizing at 60° C. for 8 minutes. After cycling, the reactions were held at 10° C. until proceeding to the next step.

After incubation, the reaction mixture proceeded directly to this step without changing buffer. The following components were added directly to each of the above reactions: 20 µl 2× Digestion buffer (50 mM Tris-HCl, pH 8.0, 15 mM $MgCl_2$, 20 mM beta mercaptoethanol), 20 T4 endonuclease VII (Affymetrix, part number 78300 50KU), 18 ul distilled water. Reactions were incubated at 37° C. for 5 minutes.

After the reaction, the DNA was purified once with 1.6×MagSi-NGSprep beads. The MagSi-NGSprep beads were suspended thoroughly in the container by vortexing, 1280 of MagSi-NGSprep beads was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 1500 freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 10 µl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, and assayed in the following step.

The size, concentration and purity of the DNA fragments were assayed in a 2100 BioAnalyzer instrument (Agilent Technologies, catalog number G2938B). 1 µl of the purified DNA fragments obtained in the previous step was assayed with a high sensitivity DNA analysis kit (Agilent Technologies, catalog number 5067-4626), according to the methods provided by the supplier. The results are presented in FIG. 14.

Example 14

Figure 15:
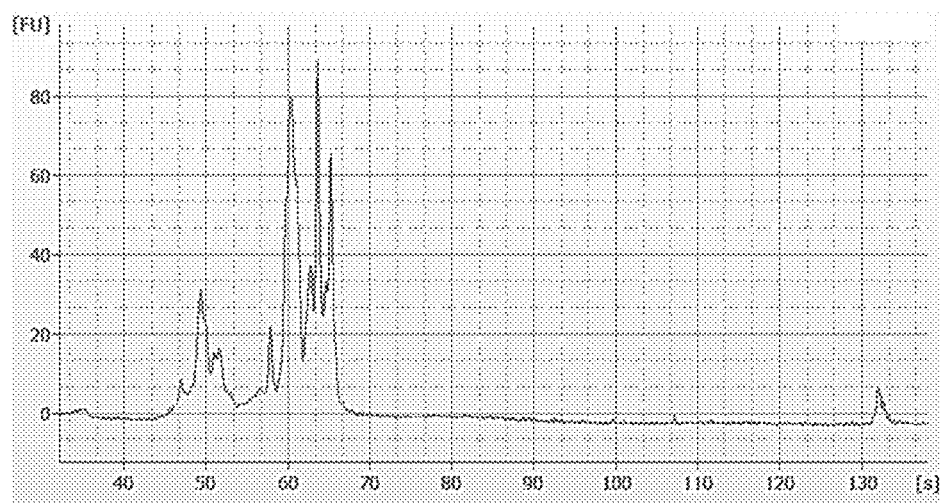
FIG. 15 illustrates an example of a multiplex amplification reaction with 207 pairs of primers using formalin-fixed paraffin embedded (FFPE) DNA from human breast cancer.

The methods described herein may be used even with very small and/or damaged DNA template, including in particular for removal of non-specific amplification products in a multiplex PCR with FFPE DNA as template. In this example, multiplex PCR was done as described in EXAMPLE 6 except that 10 ng FFPE DNA was used in each multiplex PCR reaction. After PCR, the following components were added directly to the above reactions: 10 µl 2× Digestion buffer (50 mM Tris-HCl, pH 8.0, 15 mM $MgCl_2$, 20 mM beta mercaptoethanol), 1 µl T4 endonuclease VII (Affymetrix, part number 78300 50KU), 18 ul distilled water. Reactions were incubated at 37° C. for 5 minutes. After incubation, the reactions were stopped with 0.5 M EDTA. The DNA was purified and assayed in BioAnalyzer, as described in EXAMPLE 6. The results are presented in FIG. 15. This experiment showed that non-specific amplification products were effectively removed from a multiplex PCR involving 207 pairs of primers and 10 ng of FFPA DNA.

Example 15

Multiplex PCR involving phosphorylated primers using the methods described herein was attempted. The primer panel of Ion AmpliSeq™ hotspot cancer panel v2 (Life Technologies, catalog number 4475346) was phosphorylated at 5' end by T4 polynucleotide kinase. The primers were then used in a multiplex PCR reaction at 50 nM in 10 µl. Multiplex PCR and the DNA purification thereafter were done as described in EXAMPLE 8. The purified DNA was eluted from magnetic beads in 20 µl distilled water.

The DNA fragments were blunt-ended in total 40 ul by adding to the previous purified DNA solution, 4 µl 10× Blunt end Buffer (1× blunt buffer: 50 mM Tris-HCl (pH 7.6), 10 mM $MgCl_2$, 10 mM beta mercaptoethanol, 1 mM ATP, 0.4 mM dNTP each), 12 units of T4 DNA polymerase (Molecular Cloning laboratories, catalog number T4DP-100), 40 units of polynucleotide kinase (Molecular Cloning laboratories, catalog number T4PK-100). The reaction mixture in each tube was first spun briefly for 3 second in a mini centrifuge to collect all droplets to the bottom of the tube, vortexed for 3 seconds, and then spun for 3 seconds again to ensure uniformity of the reaction. The tubes were incubated at room temperature for 10 min.

After the reaction, the DNA was purified once with 1.6×MagSi-NGSprep beads as described in EXAMPLE 8. The DNA was eluted from magnetic beads in 20 ul distilled water.

The following components were added to the purified DNA solution: 4 μl 10× A-tailing buffer (1× A-tailing buffer: 50 mM TrisHCl, pH8.3, 50 mM KCl, 1.5 mM $MgCl_2$), 0.5 μl of 100 mM ATP, 1 μl of Omni KlenTaq DNA polymerase (4.2 units/μl), and distilled water to 40 μl. The reaction mixture in each tube was first spun briefly for 3 second in a mini centrifuge to collect all droplets to the bottom of the tube, vortexed for 3 seconds, and then spun for 3 seconds again to ensure uniformity of the reaction. The tubes were incubated at 72° C. for 10 minutes.

After incubation, the reaction mixture proceeded directly to this step without changing buffer. The following components were added directly to each of the above reactions: 20 μl 2× Digestion buffer (50 mM Tris-HCl, pH 8.0, 15 mM $MgCl_2$, 20 mM beta mercaptoethanol), 2 μl T4 endonuclease VII (Affymetrix, part number 78300 50KU), 18 ul distilled water. Reactions were incubated at 37° C. for 5 min.

After the reaction, the DNA was purified once with 1.6×MagSi-NGSprep beads as described in EXAMPLE 8 and eluted in 10 μl distilled water.

For adapter ligation, two oligo nucleotides were synthesized by Integrated DNA Technologies. One oligo has the same nucleotide sequence with Illumina TruSeq universal adapter (5'AATGATACGGCGACCACCGAGATCTA-CACTCTTTCCCTACACGACGCTCTTCCGA TC*T3' (SEQ ID NO: 3)), the other has the same sequence with TruSeq adapter index 1 (5'PGATCGGAAGAGCA-CACGTCTGAACTCCAGTCACATCACGATCTCGTAT-GCCGTC TTCT*G*C*T*T*G3' (SEQ ID NO: 4)), wherein * represents the phosphorothioate bond additionally added into the sequences. To make the double-stranded adapter, the above oligos were mixed together at 10 μM each in 1×T4 DNA ligase buffer (50 mM TrisHCl, pH7.5, 10 mM $MgCl_2$, 1 mM ATP, 10 mM DTT) in a total of 100 μl in a 0.2 ml thin wall PCR tube. The tube was placed in a thermos cycler (GeneAmp® PCR system 9700 96-well gold plated) and heated at 95° C. for 2 min, 75° C. for 1 min, 55° C. for 1 min, and held at 25° C. until proceeding into the next step.

The following components were added to the above DNA solution: 4 μl T4 DNA ligase buffer, 2 μl 10M adapter, 1 μl T4 DNA ligase (New England BioLabs Inc., catalog number M0202S), 1 μl 9° N™ DNA ligase (New England BioLabs Inc., catalog number M0238S), and distilled water to 40 μl. Incubate at 16° C., 15 min, then 45° C., 15 min.

The following components were added directly into the above reaction: 1 ul of lambda exonuclease (New England BioLabs Inc., catalog number M0262S), 1 ul of E. coli Exonuclease I (New England BioLabs Inc., catalog number M0293S). The reactions were incubated at 37° C. for 5 min.

After the reaction, the DNA was purified once with 1.6×MagSi-NGSprep beads as described in EXAMPLE 8 and eluted in 20 μl distilled.

The DNA fragments obtained from the above step were further amplified by PCR for 5 cycles. The following components were added to the above DNA solution: 5 μl of 10×PCR buffer, 2.5 μl of 10 μM primer mix, 2 μl of Omni KlenTaq polymerase (4.2 units/μl), and distilled water to 50 μl. The PCR was carried out in a thermos cycler (GeneAmp® PCR system 9700 96-well gold plated) by denaturing at 98° C. for 2 min, then 5 cycles of 98° C., 15 sec, 58° C., 1 min, and then hold at 10° C. until proceeding into next step.

Primers used for PCR were: 5'AATGATACGGCGAC-CACCGA3' (SEQ ID NO: 5) and 5'CAAGCAGAAGACG-GCATACGAGAT3' (SEQ ID NO: 6). These oligos were synthesized by Integrated DNA Technologies.

Finally, the DNA was purified once with 1.6×MagSi-NGSprep beads as described in EXAMPLE 8 and eluted from magnetic beads in 20 μl TE buffer.

Figure 16:
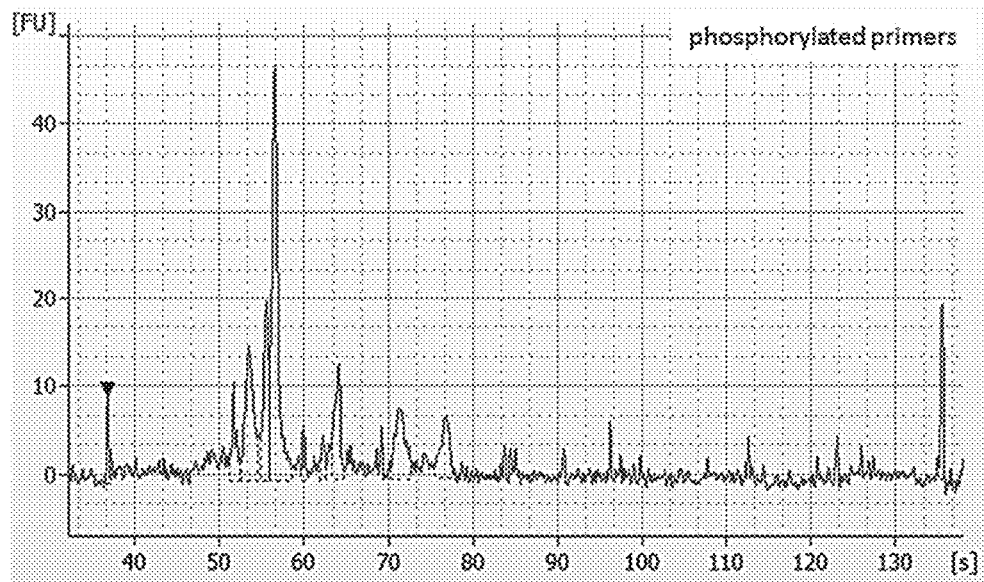
FIG. 16 illustrates the results of a failed experimental example of multiplex amplification using 207 pairs of phosphorylated primers as described below.

The size, concentration and purity of the libraries were assayed in a 2100 BioAnalyzer instrument (Agilent Technologies, catalog number G2938B). 1 μl of each library obtained in the previous step was assayed with a high sensitivity DNA analysis kit (Agilent Technologies, catalog number 5067-4626), according to the methods provided by the supplier. The results are presented in FIG. 16. In this example, no significant amount of target amplicons was produced after ligation and a second round of PCR.

Example 16

Making a library without removing unligated adapters was successfully performed using the methods described herein. Multiplex PCR and the DNA purification thereafter were done as described in EXAMPLE 8. The purified DNA was eluted from magnetic beads in 20 μl distilled water.

The DNA fragments were blunt-ended in total 40 ul by adding to the previous purified DNA solution, 4 μl 10× Blunt end Buffer (1× blunt buffer: 50 mM Tris-HCl (pH 7.6), 10 mM $MgCl_2$, 10 mM beta mercaptoethanol, 1 mM ATP, 0.4 mM dNTP each), 12 units of T4 DNA polymerase (Molecular Cloning laboratories, catalog number T4DP-100), 40 units of polynucleotide kinase (Molecular Cloning laboratories, catalog number T4PK-100). The reaction mixture in each tube was first spun briefly for 3 second in a mini centrifuge to collect all droplets to the bottom of the tube, vortexed for 3 seconds, and then spun for 3 seconds again to ensure uniformity of the reaction. The tubes were incubated at room temperature for 10 minutes.

After the reaction, the DNA was purified once with 1.6×MagSi-NGSprep beads as described in EXAMPLE 8. The DNA was eluted from magnetic beads in 20 ul distilled water.

The following components were added to the purified DNA solution: 4 μl 10× A-tailing buffer (1× A-tailing buffer: 50 mM TrisHCl, pH8.3, 50 mM KCl, 1.5 mM $MgCl_2$), 0.5 μl of 100 mM ATP, 1 μl of Omni KlenTaq DNA polymerase (4.2 units/μl), and distilled water to 40 μl. The reaction mixture in each tube was first spun briefly for 3 second in a mini centrifuge to collect all droplets to the bottom of the tube, vortexed for 3 seconds, and then spun for 3 seconds again to ensure uniformity of the reaction. The tubes were incubated at 72° C. for 10 minutes.

After incubation, the reaction mixture proceeded directly to this step without changing buffer. The following components were added directly to each of the above reactions: 20 μl 2× Digestion buffer (50 mM Tris-HCl, pH 8.0, 15 mM $MgCl_2$, 20 mM beta mercaptoethanol), 2 μl T4 endonuclease VII (Affymetrix, part number 78300 50KU), 18 ul distilled water. Reactions were incubated at 37° C. for 5 min.

After the reaction, the DNA was purified once with 1.6×MagSi-NGSprep beads as described in EXAMPLE 8 and eluted in 10 μl distilled water.

For adapter ligation, two oligo nucleotides were synthesized by Integrated DNA Technologies. One oligo has the same nucleotide sequence with Illumina TruSeq universal adapter (5'AATGATACGGCGACCACCGAGATCTA-CACTCTTTCCCTACACGACGCTCTTCCGA TC*T3' (SEQ ID NO: 3)), the other has the same sequence with TruSeq adapter index 1 (5'PGATCGGAAGAGCA-CACGTCTGAACTCCAGTCACATCACGATCTCGTAT-GCCGTC TTCT*G*C*T*T*G3' (SEQ ID NO: 4)), wherein * represents the phosphorothioate bond additionally added into the sequences. To make the double-stranded adapter, the above oligos were mixed together at 10 μM each in 1×T4 DNA ligase buffer (50 mM TrisHCl, pH7.5, 10 mM MgCl$_2$, 1 mM ATP, 10 mM DTT) in a total of 100 μl in a 0.2 ml thin wall PCR tube. The tube was placed in a thermos cycler (GeneAmp® PCR system 9700 96-well gold plated) and heated at 95° C. for 2 min, 75° C. for 1 min, 55° C. for 1 min, and held at 25° C. until proceeding into the next step.

The following components were added to the above DNA solution: 4 μl T4 DNA ligase buffer, 2 μl 10 μM adapter, 1 μl T4 DNA ligase (New England BioLabs Inc., catalog number M0202S), 1 μl 9° N™ DNA ligase (New England BioLabs Inc., catalog number M0238S), and distilled water to 40 μl. Incubate at 16° C., 15 minutes, then 45° C., 15 minutes.

After the reaction, the DNA was purified once with 1.6×MagSi-NGSprep beads as described in EXAMPLE 8 and eluted in 20 μl distilled.

The DNA fragments obtained from the above step were further amplified by PCR for 5 cycles. The following components were added to the above DNA solution: 5 μl of 10×PCR buffer, 2.5 μl of 10 μM primer mix, 2 μl of Omni KlenTaq polymerase (4.2 units/μl), and distilled water to 50 μl. The PCR was carried out in a thermos cycler (GeneAmp® PCR system 9700 96-well gold plated) by denaturing at 98° C. for 2 minutes, then 5 cycles of 98° C., 15 sec, 58° C., 1 minutes, and then hold at 10° C. until proceeding into next step.

Primers used for PCR were: 5'AATGATACGGCGAC-CACCGA3' (SEQ ID NO: 5) and 5'CAAGCAGAAGACG-GCATACGAGAT3' (SEQ ID NO: 6). These oligos were synthesized by Integrated DNA Technologies.

Finally, the DNA was purified once with 1.6×MagSi-NGSprep beads as described in EXAMPLE 8 and eluted from magnetic beads in 20 μl TE buffer.

Figure 17:
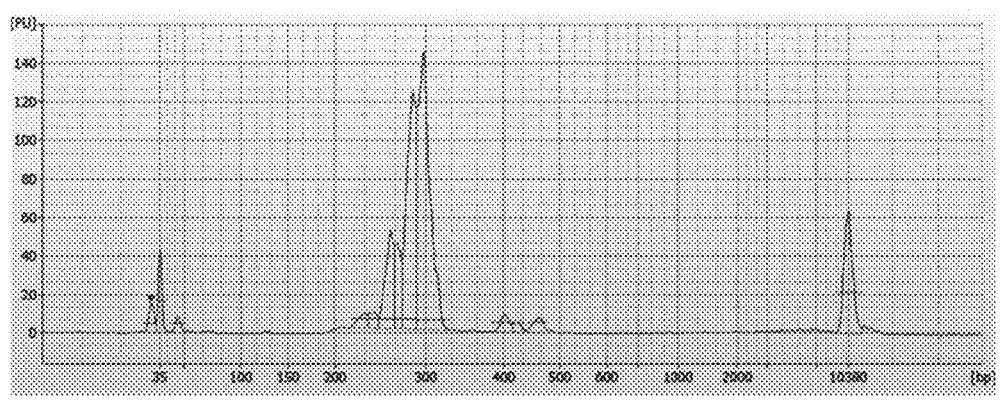
FIG. 17 shows an example of the results of making a library (e.g., for sequencing) using multiplex amplification and treatment with resolvase to remove non-specific amplification products as described herein (in this example, using 207 pairs of primers).

The size, concentration and purity of the libraries were assayed in a 2100 BioAnalyzer instrument (Agilent Technologies, catalog number G2938B). 1 μl of each library obtained in the previous step was assayed with a high sensitivity DNA analysis kit (Agilent Technologies, catalog number 5067-4626), according to the methods provided by the supplier. The results are presented in FIG. 17. Some non-specific products were present in the final library.

Example 17

Figure 18:
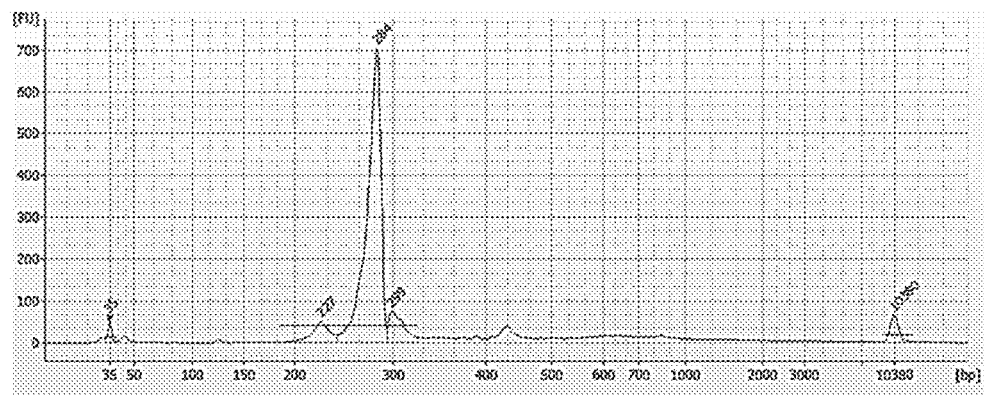
FIG. 18 illustrates another example of a method of making a library (e.g., for sequencing) using multiplex amplification and treatment with resolvase to remove non-specific amplification products as described herein (in this example, using 2915 pairs of primers).

The methods described herein may be used to make a library. For example, FIG. 18 illustrates the results of the use of resolvase to remove non-specific amplification products in the production of a library involving 2915 pairs of primers.

In this example, the primer panel Qiagen GeneRead DNAseq human breast cancer panel (Qiagen, catalog number NGHS-001X-12), as described in EXAMPLE 8, was used test the workflow to make a library. Multiplex PCR and the DNA purification thereafter were done as described in EXAMPLE 8. The purified DNA was eluted from magnetic beads in 20 μl distilled water.

The DNA fragments were blunt-ended in total 40 ul by adding to the previous purified DNA solution, 4 μl 10× Blunt end Buffer (1× blunt buffer: 50 mM Tris-HCl (pH 7.6), 10 mM MgCl$_2$, 10 mM beta mercaptoethanol, 1 mM ATP, 0.4 mM dNTP each), 12 units of T4 DNA polymerase (Molecular Cloning laboratories, catalog number T4DP-100), 40 units of polynucleotide kinase (Molecular Cloning laboratories, catalog number T4PK-100). The reaction mixture in each tube was first spun briefly for 3 second in a mini centrifuge to collect all droplets to the bottom of the tube, vortexed for 3 seconds, and then spun for 3 seconds again to ensure uniformity of the reaction. The tubes were incubated at room temperature for 10 min.

After the reaction, the DNA was purified once with 1.6×MagSi-NGSprep beads as described in EXAMPLE 8. The DNA was eluted from magnetic beads in 20 ul distilled water.

The following components were added to the purified DNA solution: 4 μl 10× A-tailing buffer (1× A-tailing buffer: 50 mM TrisHCl, pH8.3, 50 mM KCl, 1.5 mM MgCl$_2$), 0.5 μl of 100 mM ATP, 1 μl of Omni KlenTaq DNA polymerase (4.2 units/μl), and distilled water to 40 μl. The reaction mixture in each tube was first spun briefly for 3 second in a mini centrifuge to collect all droplets to the bottom of the tube, vortexed for 3 seconds, and then spun for 3 seconds again to ensure uniformity of the reaction. The tubes were incubated at 72° C. for 10 minutes.

After incubation, the reaction mixture proceeded directly to this step without changing buffer. The following components were added directly to each of the above reactions: 20 μl 2× Digestion buffer (50 mM Tris-HCl, pH 8.0, 15 mM MgCl$_2$, 20 mM beta mercaptoethanol), 2 μl T4 endonuclease VII (Affymetrix, part number 78300 50KU), 18 ul distilled water. Reactions were incubated at 37° C. for 5 minutes.

After the reaction, the DNA was purified once with 1.6×MagSi-NGSprep beads as described in EXAMPLE 8 and eluted in 10 μl distilled water.

For adapter ligation, two oligo nucleotides were synthesized by Integrated DNA Technologies. One oligo has the same nucleotide sequence with Illumina TruSeq universal adapter (5'AATGATACGGCGACCACCGAGATCTA-CACTCTTTCCCTACACGACGCTCTTCCGA TC*T3' (SEQ ID NO: 3)), the other has the same sequence with TruSeq adapter index 1 (5'PGATCGGAAGAGCA-CACGTCTGAACTCCAGTCACATCACGATCTCGTAT-GCCGTC TTCT*G*C*T*T*G3' (SEQ ID NO: 4)), wherein * represents the phosphorothioate bond additionally added into the sequences. To make the double-stranded adapter, the above oligos were mixed together at 10 μM each in 1×T4 DNA ligase buffer (50 mM TrisHCl, pH7.5, 10 mM MgCl$_2$, 1 mM ATP, 10 mM DTT) in a total of 100 μl in a 0.2 ml thin wall PCR tube. The tube was placed in a thermos cycler (GeneAmp® PCR system 9700 96-well gold plated) and heated at 95° C. for 2 minutes, 75° C. for 1 minute, 55° C. for 1 minute, and held at 25° C. until proceeding into the next step.

The following components were added to the above DNA solution: 4 μl T4 DNA ligase buffer, 2 μl 10 μM adapter, 1 μl T4 DNA ligase (New England BioLabs Inc., catalog number M0202S), 1 μl 9° N™ DNA ligase (New England BioLabs Inc., catalog number M0238S), and distilled water to 40 μl. Incubate at 16° C., 15 minutes, then 45° C., 15 minute.

The following components were added directly into the above reaction: 1 ul of lambda exonuclease (New England BioLabs Inc., catalog number M0262S), 1 ul of E. coli Exonuclease I (New England BioLabs Inc., catalog number M0293S). The reactions were incubated at 37° C. for 5 min.

After the reaction, the DNA was purified once with 1.6×MagSi-NGSprep beads as described in EXAMPLE 8 and eluted in 20 µl distilled.

The DNA fragments obtained from the above step were further amplified by PCR for 5 cycles. The following components were added to the above DNA solution: 5 µl of 10×PCR buffer, 2.5 µl of 10 µM primer mix, 2 µl of Omni KlenTaq polymerase (4.2 units/µl), and distilled water to 50 µl. The PCR was carried out in a thermos cycler (GeneAmp® PCR system 9700 96-well gold plated) by denaturing at 98° C. for 2 min, then 5 cycles of 98° C., 15 sec, 58° C., 1 minute, and then hold at 10° C. until proceeding into next step.

Primers used for PCR were: 5'AATGATACGGCGACCACCGA3' (SEQ ID NO: 5) and 5'CAAGCAGAAGACGGCATACGAGAT3' (SEQ ID NO. 6). These oligos were synthesized by Integrated DNA Technologies.

Finally, the DNA was purified once with 1.6×MagSi-NGSprep beads as described in EXAMPLE 8 and eluted from magnetic beads in 20 µl TE buffer.

The size, concentration and purity of the libraries were assayed in a 2100 BioAnalyzer instrument (Agilent Technologies, catalog number G2938B). 1 µl of each library obtained in the previous step was assayed with a high sensitivity DNA analysis kit (Agilent Technologies, catalog number 5067-4626), according to the methods provided by the supplier. The results are presented in FIG. 18. In this example, the target amplification products are shown by the peaks between 200-300 bp; very little background remains following the resolvase treatment discussed above.

Example 18

Figure 19:
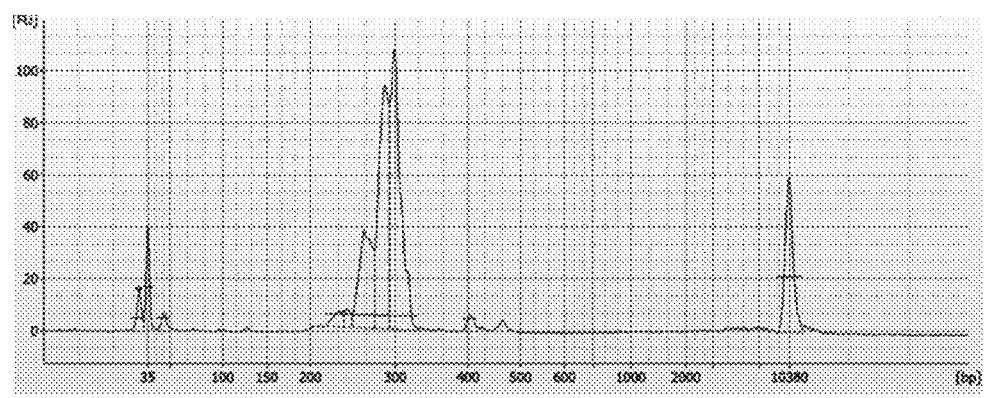
FIG. 19 illustrates another example of a method of method of making a library (e.g., for sequencing) using multiplex amplification and treatment with resolvase to remove non-specific amplification products as described herein (in this example, using 207 pairs of primers).

FIG. 19 illustrates another example of a library made with 207 pairs of primers, for sequencing. In this example, the primer panel of Ion AmpliSeq™ hotspot cancer panel v2 (Life Technologies, catalog number 4475346) was used in multiplex PCR. This primer panel covers approximately 2,800 COSMIC mutations from 50 oncogenes and tumor suppressor genes. It has 207 primer pairs in one pool. The multiplex PCR reaction was done in 10 µl. The following components were added to each of a 0.2 ml thin wall PCR tube (Thomas Scientific, Snapstrip II natural 0.2 ml PCR strip tube, catalog number 1228F73): 5 µl of the 2-fold concentrated primer pool, 1 µl 10×PCR buffer (1×PCR buffer: 50 mM TrisHCl, pH8.3, 50 mM KCl, 5 mM MgCl$_2$, 0.8 mM dNTP each), 2 µl Omni KlenTaq DNA polymerase (4.2 units/µl) (Enzymatics, P7500-LC-F), 1 µl of 10 ng/µl of human DNA (Coriell Institute, NA12878), and 1 µl distilled water.

The 0.2 ml thin wall PCR tubes were capped with the attached caps, vortexed brief for 3 seconds and spun in a mini centrifuge (Pipette.com, MyFuge 12 place mini centrifuge, catalog number C1012) for 3 seconds. No mineral oil was required to cover the PCR reaction mixture. The tubes were placed in a thermos cycler (GeneAmp® PCR system 9700 96-well gold plated, Life Technologies, catalog number 4314878).

The PCR was initially held at 98° C. for 2 minutes, followed by 17 cycles of denaturing at 98° C. for 15 seconds and annealing and synthesizing at 60° C. for 4 minutes. After cycling, the reactions were held at 10° C. until proceeding to the next step.

After PCR, paramagnetic beads were used to absorb DNA, which was then washed with 70% ethanol to remove proteins, dNTPs, salts, and part of PCR primers. The paramagnetic beads were from Amsbio LLC (Amsbio LLC, MagSi-NGSprep, catalog number MD61021). The MagSi-NGSprep beads were suspended thoroughly in the container by vortexing, then 64 µl of MagSi-NGSprep beads, representing 1.6-fold of the volume of the amplified and combined amplicons, was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. The magnet inside magnetic rack was from KJ Magnetics (KJ Magnetics, catalog number D4X0DIA-N52). Once the solution cleared, the supernatant was carefully pipetted out and discarded without disturbing the bead pellet. Without removing the tubes from the magnetic rack, 150 µl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 20 µl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

The DNA fragments were blunt-ended in total 40 ul by adding to the previous purified DNA solution, 4 µl 10× Blunt end Buffer (1× blunt buffer: 50 mM Tris-HCl (pH 7.6), 10 mM MgCl$_2$, 10 mM beta mercaptoethanol, 1 mM ATP, 0.4 mM dNTP each), 12 units of T4 DNA polymerase (Molecular Cloning laboratories, catalog number T4DP-100), 40 units of polynucleotide kinase (Molecular Cloning laboratories, catalog number T4PK-100). The reaction mixture in each tube was first spun briefly for 3 second in a mini centrifuge to collect all droplets to the bottom of the tube, vortexed for 3 seconds, and then spun for 3 seconds again to ensure uniformity of the reaction. The tubes were incubated at room temperature for 10 minutes.

After the reaction, the DNA was purified once with 1.6×MagSi-NGSprep beads. The MagSi-NGSprep beads were suspended thoroughly in the container by vortexing, 64 µl of MagSi-NGSprep beads was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 150 µl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 20 μl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

The following components were added to the purified DNA solution: 4 μl 10× A-tailing buffer (1× A-tailing buffer: 50 mM TrisHCl, pH8.3, 50 mM KCl, 1.5 mM MgCl$_2$), 0.5 μl of 100 mM ATP, 1 μl of Omni KlenTaq DNA polymerase (4.2 units/μl), and distilled water to 40 μl. The reaction mixture in each tube was first spun briefly for 3 second in a mini centrifuge to collect all droplets to the bottom of the tube, vortexed for 3 seconds, and then spun for 3 seconds again to ensure uniformity of the reaction. The tubes were incubated at 72° C. for 10 minutes.

After incubation, the reaction mixture proceeded directly to this step without changing buffer. The following components were added directly to each of the above reactions: 20 μl 2× Digestion buffer (50 mM Tris-HCl, pH 8.0, 15 mM MgCl$_2$, 20 mM beta mercaptoethanol), 2 μl T4 endonuclease VII (Affymetrix, part number 78300 50KU), 18 ul distilled water. Reactions were incubated at 37° C. for 5 minutes.

After the reaction, the DNA was purified once with 1.6×MagSi-NGSprep beads. The MagSi-NGSprep beads were suspended thoroughly in the container by vortexing, 128 μl of MagSi-NGSprep beads was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 150 μl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 10 μl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

For ligation with adapters, two oligo nucleotides were synthesized by Integrated DNA Technologies. One oligo has the same nucleotide sequence with Illumina TruSeq universal adapter (5'AATGATACGGCGACCACCGAGATCTA-CACTCTTTCCCTACACGACGCTCTTCCGA TC*T3' (SEQ ID NO: 3)), the other has the same sequence with TruSeq adapter index 1 (5'PGATCGGAAGAGCA-CACGTCTGAACTCCAGTCACATCACGATCTCGTAT-GCCGTC TTCT*G*C*T*T*G3' (SEQ ID NO: 4)), wherein * represents the phosphorothioate bond additionally added into the sequences. To make the double-stranded adapter, the above oligos were mixed together at 10 μM each in 1×T4 DNA ligase buffer (50 mM TrisHCl, pH7.5, 10 mM MgCl$_2$, 1 mM ATP, 10 mM DTT) in a total of 100 μl in a 0.2 ml thin wall PCR tube. The tube was placed in a thermos cycler (GeneAmp® PCR system 9700 96-well gold plated) and heated at 95° C. for 2 minutes, 75° C. for 1 minute, 55° C. for 1 minute, and held at 25° C. until proceeding into the next step.

The following components were added to the above DNA solution: 4 μl T4 DNA ligase buffer, 2 μl 10 μM adapter, 1 μl T4 DNA ligase (New England BioLabs Inc., catalog number M0202S), 1 μl 9° N™ DNA ligase (New England BioLabs Inc., catalog number M0238S), and distilled water to 40 μl. Incubate at 16° C., 15 minutes, then 45° C., 15 minutes.

The following components were added directly into the above reaction: 1 ul of lambda exonuclease (New England BioLabs Inc., catalog number M0262S), 1 ul of E. coli Exonuclease I (New England BioLabs Inc., catalog number M0293S). The reactions were incubated at 37° C. for 5 minutes.

After the reaction, the DNA was purified once with 1.6×MagSi-NGSprep beads. The MagSi-NGSprep beads were suspended thoroughly in the container by vortexing, 64 μl of MagSi-NGSprep beads was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 150 μl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 20 μl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

The DNA fragments obtained from the above step were further amplified by PCR for 5 cycles. The following components were added to the above DNA solution: 5 μl of 10×PCR buffer, 2.5 μl of 10 μM primer mix, 2 μl of Omni KlenTaq polymerase (4.2 units/μl), and distilled water to 50 μl. The PCR was carried out in a thermos cycler (GeneAmp® PCR system 9700 96-well gold plated) by denaturing at 98° C. for 2 minutes, then 5 cycles of 98° C., 15 seconds, 58° C., 1 minute, and then hold at 10° C. until proceeding into next step.

Primers used for PCR were: 5'AATGATACGGCGAC-CACCGA3' (SEQ ID NO: 5) and 5'CAAGCAGAAGACG- GCATACGAGAT3' (SEQ ID NO: 6). These oligos were synthesized by Integrated DNA Technologies.

After the reaction, the DNA was purified once with 1.6×MagSi-NGSprep beads. The MagSi-NGSprep beads were suspended thoroughly in the container by vortexing, 64 µl of MagSi-NGSprep beads was added into each tube. These were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 150 µl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 20 µl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

The size, concentration and purity of the libraries were assayed in a 2100 BioAnalyzer instrument (Agilent Technologies, catalog number G2938B). 1 µl of each library obtained in the previous step was assayed with a high sensitivity DNA analysis kit (Agilent Technologies, catalog number 5067-4626), according to the methods provided by the supplier. The results are presented in FIG. 19. This library was sequenced and analyzed by SeqMatic LLC (Fremont, Calif. 94539), the results were presented in FIG. 22 (Table 1). This library had a major peak of 300 base pairs (e.g., between 200 and 400 bp). Table 1 shows that the quality confirmation of the sequencing results of the library with 207 pairs of primers. Highlight of the specifications are PCT_PF_UQ_READS_ALIGNED 99.46%, PCT_AMPLIFIED_BASES 95.63%, Percent amplicon at >=20% of mean 98.55%. The coverage (PCT_TARGET_BASES_2X-PCT_TARGET_BASES_100X) showed an excellent (99.97-100%) coverage in this example, while the uniformity (percent amplicon at >=20% of mean of 98.55%) was extremely high.

Example 19

Figure 20:
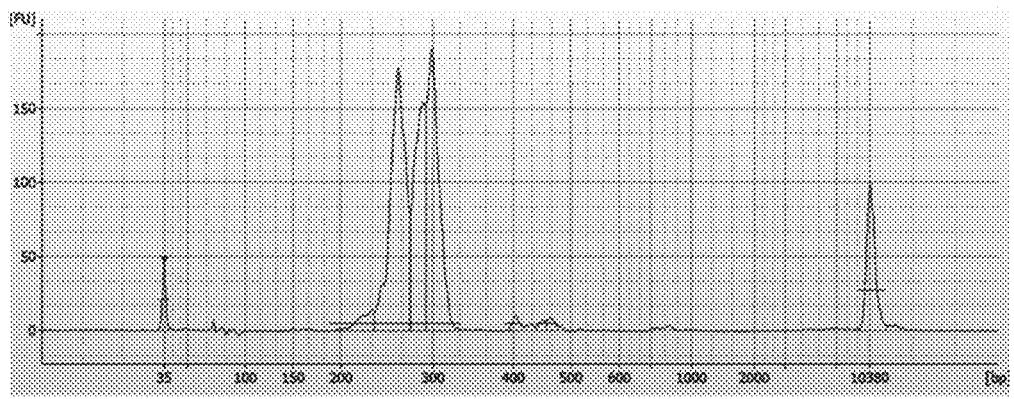
FIG. 20 illustrates another example of a method of method of making a library (e.g., for sequencing) using multiplex amplification and treatment with resolvase to remove non-specific amplification products as described herein (in this example, using 207 pairs of long primers).

FIG. 20 shows another example of a library made as described herein, with 207 pairs of long primers for sequencing. An analysis of this library is shown in the table (Table 2) in FIG. 23. In this example, the primer panel was identical to that of Ion AmpliSeq™ hotspot cancer panel v2 (Life Technologies, catalog number 4475346), except that 5'CCTACACGACGCTCTTCCGATCT3' (SEQ ID NO: 1) was added to the 5' end of each forward primer, and 5'TTCAGACGTGTGCTCTTCCGATCT3' (SEQ ID NO: 2) was added to 5' end of each reverse primer. These "long" primers allow easy addition of adapters onto amplicons by an additional round of PCR. The multiplex PCR reaction was done in 10 µl. The following components were added to each of a 0.2 ml thin wall PCR tube (Thosmas Scientific, Snapstrip II natural 0.2 ml PCR strip tube, catalog number 1228F73): 5 µl of the 2-fold concentrated primer pool, 1 µl 10×PCR buffer (1×PCR buffer: 50 mM TrisHCl, pH8.3, 50 mM KCl, 5 mM MgCl$_2$, 0.8 mM dNTP each), 2 µl Omni KlenTaq DNA polymerase (4.2 units/µl) (Enzymatics, P7500-LC-F), 1 µl of 10 ng/µl of human DNA (Coriell Institute, NA12878), and 1 µl distilled water.

The 0.2 ml thin wall PCR tubes were capped with the attached caps, vortexed brief for 3 seconds and spun in a mini centrifuge (Pipette.com, MyFuge 12 place mini centrifuge, catalog number C1012) for 3 seconds. No mineral oil was required to cover the PCR reaction mixture. The tubes were placed in a thermos cycler (GeneAmp® PCR system 9700 96-well gold plated, Life Technologies, catalog number 4314878).

The PCR was initially held at 98° C. for 2 minutes, followed by 17 cycles of denaturing at 98° C. for 15 seconds and annealing and synthesizing at 60° C. for 4 min. After cycling, the reactions were held at 10° C. until proceeding to the next step.

After PCR, paramagnetic beads were used to absorb DNA, which was then washed with 70% ethanol to remove proteins, dNTPs, salts, and part of PCR primers. The paramagnetic beads were from Amsbio LLC (Amsbio LLC, MagSi-NGSprep, catalog number MD61021). The MagSi-NGSprep beads were suspended thoroughly in the container by vortexing, then 64 µl of MagSi-NGSprep beads, representing 1.6-fold of the volume of the amplified and combined amplicons, was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. The magnet inside magnetic rack was from KJ Magnetics (KJ Magnetics, catalog number D4X0DIA-N52). Once the solution cleared, the supernatant was carefully pipetted out and discarded without disturbing the bead pellet. Without removing the tubes from the magnetic rack, 150 µl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 20 µl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

The following components were added directly to each of the above reactions: 20 µl 2× Digestion buffer (50 mM Tris-HCl, pH 8.0, 15 mM MgCl$_2$, 20 mM beta mercaptoethanol), 2 µl T4 endonuclease VII (Affymetrix, part number 78300 50KU), 18 ul distilled water. Reactions were incubated at 37° C. for 5 minutes.

After the reaction, the DNA was purified once with 1.6×MagSi-NGSprep beads. The MagSi-NGSprep beads were suspended thoroughly in the container by vortexing, 128 µl of MagSi-NGSprep beads was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 150 µl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 10 µl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

The DNA fragments obtained from the above step were further amplified by PCR for 5 cycles. The following components were added to the above DNA solution: 5 µl of 10×PCR buffer, 2.5 µl of 10 µM primer mix, 2 µl of Omni KlenTaq polymerase (4.2 units/µl), and distilled water to 50 µl. The PCR was carried out in a thermos cycler (GeneAmp® PCR system 9700 96-well gold plated) by denaturing at 98° C. for 2 min, then 5 cycles of 98° C., 15 sec, 58° C., 1 minute, and then hold at 10° C. until proceeding into next step.

Primers used for PCR were: 5' AATGATACGGCGAC-CACCGAGATCTACACTCTTTCCCTACAC-GACGCTCTTCCGATC T3' (SEQ ID NO: 7) and 5' GATCGGAAGAGCACACGTCTGAACTCCAGTCA-CATCACGATCTCGTATGCCGTCTTC TGCTTG3' (SEQ ID NO: 8). These oligos were synthesized by Integrated DNA Technologies.

The size, concentration and purity of the libraries were assayed in a 2100 BioAnalyzer instrument (Agilent Technologies, catalog number G2938B). 1 µl of each library obtained in the previous step was assayed with a high sensitivity DNA analysis kit (Agilent Technologies, catalog number 5067-4626), according to the methods provided by the supplier. The results are presented in FIG. 20. This library was sequenced and analyzed by SeqMatic LLC (Fremont, Calif. 94539), the results were presented in Table 2 of FIG. 23. This library had a major peak of 300 base pairs (e.g., between 200-400). The quality confirmation of the sequencing results of the library with 207 pairs of long primers shown in FIG. 23 shows highlight of the specifications including PCT_PF_UQ_READS_ALIGNED 99.62%, PCT_AMPLIFIED_BASES 98.94%, and a high uniformity (e.g., percent amplicon at >=20% of mean 97.52%).

Example 20

FIG. 21A shows the results of another example of a library made as described herein including treating with resolvase to reduce non-specific amplification products, in which the library was made with 16000 pairs of primers for sequencing. Table 3 (FIG. 24) describes an analysis of this library.

The primer panel was Ion AmpliSeq™ comprehensive cancer panel (Life Technologies, catalog number 4477685). This primer panel covers all-exons of 409 key tumor suppressor genes and oncogenes that are frequently mutated and cited in scientific publications. This has 16000 primer pairs in 4 pools; each pool has approximately 4,000 primer pairs. The lengths of the amplicons range from 125-175 base pairs, the target region covers approximately 1.73 million bases. When libraries was made with this panel and Life Technologies' Ion AmpliSeq™ Library Kit 2.0, and sequenced in Life Technologies' Ion PGM™ system, this panel has reported coverage of 94% at >20% median sequencing depth, with on target bases (bases mapped to target regions, out of total mapped bases per run) of 97%. In multiplex PCR, each of the 4 primer pools requires 10 ng of human genomic DNA as template, total of 40 ng to cover the entire panel. There is at least one uracil nucleotide in each primer of this primer panel. This primer panel is in 2-fold concentrated. Therefore, 4 PCR reactions were performed with each of the 4 pools of primer.

The multiplex PCR reaction was done in 10 µl. The following components were added to each of a 0.2 ml thin wall PCR tube (Thosmas Scientific, Snapstrip II natural 0.2 ml PCR strip tube, catalog number 1228F73): 5 µl of the 2-fold concentrated primer pool, 1 µl 10×PCR buffer (1×PCR buffer: 50 mM TrisHCl, pH8.3, 50 mM KCl, 5 mM MgCl$_2$, 0.8 mM dNTP each), 2 µl Omni KlenTaq DNA polymerase (4.2 units/µl) (Enzymatics, P7500-LC-F), 1 µl of 10 ng/µl of human DNA (Coriell Institute, NA12878), and 1 µl distilled water. There were 4 multiplex PCR reactions for the Ion AmpliSeq™ comprehensive cancer panel.

The 0.2 ml thin wall PCR tubes were capped with the attached caps, vortexed brief for 3 seconds and spun in a mini centrifuge (Pipette.com, MyFuge 12 place mini centrifuge, catalog number C1012) for 3 seconds. No mineral oil was required to cover the PCR reaction mixture. The tubes were placed in a thermos cycler (GeneAmp® PCR system 9700 96-well gold plated, Life Technologies, catalog number 4314878). The following two temperature profiles were performed for each of the primer panel.

The PCR was initially held at 98° C. for 2 minutes, followed by 13 cycles of denaturing at 98° C. for 15 seconds and annealing and synthesizing at 60° C. for 8 min. After cycling, the reactions were held at 10° C. until proceeding to the next step.

After PCR, the 4 reactions representing the full primer panel of either Ion AmpliSeq™ Comprehensive Cancer Panel were combined, resulting in 1 tubes of 40 µl amplified amplicon library. Paramagnetic beads were used to absorb DNA, which was then washed with 70% ethanol to remove proteins, dNTPs, salts, and part of PCR primers. The paramagnetic beads were from Amsbio LLC (Amsbio LLC, MagSi-NGSprep, catalog number MD61021). The MagSi-NGSprep beads were suspended thoroughly in the container by vortexing, then 64 µl of MagSi-NGSprep beads, representing 1.6-fold of the volume of the amplified and combined amplicons, was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. The magnet inside magnetic rack was from KJ Magnetics (KJ Magnetics, catalog number D4X0DIA-N52). Once the solution cleared, the supernatant was carefully pipetted out and discarded without disturbing the bead pellet. Without removing the tubes from the magnetic rack, 150 μl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 20 μl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

The DNA fragments were blunt-ended in total 40 ul by adding to the previous purified DNA solution, 4 μl 10× Blunt end Buffer (1× blunt buffer: 50 mM Tris-HCl (pH 7.6), 10 mM MgCl$_2$, 10 mM beta mercaptoethanol, 1 mM ATP, 0.4 mM dNTP each), 12 units of T4 DNA polymerase (Molecular Cloning laboratories, catalog number T4DP-100), 40 units of polynucleotide kinase (Molecular Cloning laboratories, catalog number T4PK-100). The reaction mixture in each tube was first spun briefly for 3 second in a mini centrifuge to collect all droplets to the bottom of the tube, vortexed for 3 seconds, and then spun for 3 seconds again to ensure uniformity of the reaction. The tubes were incubated at room temperature for 10 min.

After the reaction, the DNA was purified once with 1.6×MagSi-NGSprep beads. The MagSi-NGSprep beads were suspended thoroughly in the container by vortexing, 64 μl of MagSi-NGSprep beads was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 150 μl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 20 μl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

The following components were added to the purified DNA solution: 4 μl 10× A-tailing buffer (1× A-tailing buffer: 50 mM TrisHCl, pH8.3, 50 mM KCl, 1.5 mM MgCl$_2$), 0.5 μl of 100 mM ATP, 1 μl of Omni KlenTaq DNA polymerase (4.2 units/μl), and distilled water to 40 μl. The reaction mixture in each tube was first spun briefly for 3 second in a mini centrifuge to collect all droplets to the bottom of the tube, vortexed for 3 seconds, and then spun for 3 seconds again to ensure uniformity of the reaction. The tubes were incubated at 72° C. for 10 minutes.

After incubation, the reaction mixture proceeded directly to this step without changing buffer. The following components were added directly to each of the above reactions: 20 μl 2× Digestion buffer (50 mM Tris-HCl, pH 8.0, 15 mM MgCl$_2$, 20 mM beta mercaptoethanol), 2 μl T4 endonuclease VII (Affymetrix, part number 78300 50KU), 18 ul distilled water. Reactions were incubated at 37° C. for 5 minutes.

After the reaction, the DNA was purified once with 1.6×MagSi-NGSprep beads. The MagSi-NGSprep beads were suspended thoroughly in the container by vortexing, 128l of MagSi-NGSprep beads was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 150 μl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 10 μl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

For ligation with adapters, two oligo nucleotides were synthesized by Integrated DNA Technologies. One oligo has the same nucleotide sequence with Illumina TruSeq universal adapter (5'AATGATACGGCGACCACCGAGATCTA-CACTCTTTCCCTACACGACGCTCTTCCGA TC*T3' (SEQ IF NO: 3)), the other has the same sequence with TruSeq adapter index 1 (5'PGATCGGAAGAGCA-CACGTCTGAACTCCAGTCACATCACGATCTCGTAT-GCCGTC TTCT*G*C*T*T*G3' (SEQ ID NO: 4)), wherein * represents the phosphorothioate bond additionally added into the sequences. To make the double-stranded adapter, the above oligos were mixed together at 10 μM each in 1×T4 DNA ligase buffer (50 mM TrisHCl, pH7.5, 10 mM MgCl$_2$, 1 mM ATP, 10 mM DTT) in a total of 100 μl in a 0.2 ml thin wall PCR tube. The tube was placed in a thermos cycler (GeneAmp® PCR system 9700 96-well gold plated) and heated at 95° C. for 2 minutes, 75° C. for 1 minute, 55° C. for 1 minute, and held at 25° C. until proceeding into the next step.

The following components were added to the above DNA solution: 4 μl T4 DNA ligase buffer, 2 μl 10 μM adapter, 1 μl T4 DNA ligase (New England BioLabs Inc., catalog number M0202S), 1 μl 9° N™ DNA ligase (New England BioLabs Inc., catalog number M0238S), and distilled water to 40 μl. Incubate at 16° C., 15 minutes, then 45° C., 15 minutes.

The following components were added directly into the above reaction: 1 ul of lambda exonuclease (New England BioLabs Inc., catalog number M0262S), 1 ul of E. coli Exonuclease I (New England BioLabs Inc., catalog number M0293S). The reactions were incubated at 37° C. for 5 min After the reaction, the DNA was purified once with 1.6×MagSi-NGSprep beads. The MagSi-NGSprep beads were suspended thoroughly in the container by vortexing, 64 μl of MagSi-NGSprep beads was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 150 μl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 20 μl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

The DNA fragments obtained from the above step were further amplified by PCR for 5 cycles. The following components were added to the above DNA solution: 5 μl of 10×PCR buffer, 2.5 μl of 10 μM primer mix, 2 μl of Omni KlenTaq polymerase (4.2 units/μl), and distilled water to 50 μl. The PCR was carried out in a thermos cycler (GeneAmp® PCR system 9700 96-well gold plated) by denaturing at 98° C. for 2 min, then 5 cycles of 98° C., 15 seconds, 58° C., 1 minute, and then hold at 10° C. until proceeding into next step.

Primers used for PCR were: 5'AATGATACGGCGACCACCGA3' (SEQ ID NO: 5) and 5'CAAGCAGAAGACGGCATACGAGAT3' (SEQ ID NO: 6). These oligos were synthesized by Integrated DNA Technologies.

After the reaction, the DNA was purified once with 1.6×MagSi-NGSprep beads. The MagSi-NGSprep beads were suspended thoroughly in the container by vortexing, 64 μl of MagSi-NGSprep beads was added into each tube. These tubes were mixed by vortexing for 5 seconds and incubated at room temperature for 5 minutes. Then the tubes were spun in a mini centrifuge for 3 seconds, and placed on a magnetic rack to capture the beads for 2 minutes. Once the solution cleared, the supernatant was carefully pipetted out and discarded without disturbing the bead pellet. Without removing the tubes from the magnetic rack, 150 μl freshly made 70% ethanol was added into each tube. The tubes were then rotated 180 degree on the magnet rack, allowing the bead pellets to detach from one side of the inner wall of each tube, and pellet on the opposite side. Once the solution cleared, the supernatants were carefully pipetted out and discarded without disturbing the bead pellet. The beads were washed with 70% ethanol in this way for a total of 2 times. After pipetting out the 70% ethanol in the final wash, the tubes were spun in a mini centrifuge for 3 seconds. Any remaining ethanol droplets inside the tubes were pipetted out without disturbing the bead pellets. The bead pellets were air-dried for 3 minutes at room temperature on the magnet rack with tube caps open. Finally, the tubes were removed from the magnetic rack and 20 μl distilled water was added into each tube. The tubes were vortexed vigorously for 5 seconds to resuspend the beads into distilled water, spun in a mini centrifuge for 3 seconds, and placed in the magnetic rack for 2 minutes. After the solution cleared, the supernatants containing the eluted DNA fragments were transferred into fresh tubes, respectively.

The size, concentration and purity of the libraries were assayed in a 2100 BioAnalyzer instrument (Agilent Technologies, catalog number G2938B). 1 μl of each library obtained in the previous step was assayed with a high sensitivity DNA analysis kit (Agilent Technologies, catalog number 5067-4626), according to the methods provided by the supplier. The results are presented in FIG. 21B. This library was sequenced and analyzed by SeqMatic LLC (Fremont, Calif. 94539), the results were presented in Table 3 (FIG. 24). As outlined in FIG. 21A, the library (which may be used for next generation sequencing) was made with 16000 pairs of primers and human genomic DNA (NA12878) by the methods described in Example 3, and the final library shown in FIG. 21B. This library is the single peak of 300 base pairs (between 200-400 bp). As shown in Table 3 (FIG. 24), quality confirmation of the sequencing results of this library made with 16000 pairs of primers results in both high coverage and uniformity (e.g., PCT_PF_UQ_READS_ALIGNED 98.18%, PCT_AMPLIFIED_BASES 99.39%, Percent amplicon at >=20% of mean 95.20%).

Example 21

Any of the apparatuses and methods described herein may be incorporate into an exemplary kit for reducing non-specific amplification products formed between primers and between primers and template in a template-dependent primer extension reaction. For example, a targeted library kit may be provided. An example of a targeted library kit may include 5×mPCR Mix (e.g., 250 mM TrisHCl, pH8.3, 250 mM KCl, 25 mM $MgCl_2$, 1 mM dNTP each, 5 units/μl units of Taq DNA polymerase)

10× Digestion Buffer (e.g., 500 mM Tris-HCl, pH 8.0, 150 mM $MgCl_2$, 200 mM beta mercaptoethanol)

Digestion Reagent (e.g, 1000 units/μl of T4 endonuclease VII in 50 mM Tris-HCl, pH 8.0, 15 mM $MgCl_2$, 10 mM beta mercaptoethanol)

Stop Buffer (e.g, 0.5M EDTA)

5×2nd PCR Mix (e.g, 250 mM TrisHCl, pH8.3, 250 mM KCl, 25 mM $MgCl_2$, 1 mM dNTP each, 0.5 units/μl of Taq DNA polymerase)

TE Buffer (e.g., 0.1 mM Tris, 0.1 mM EDTA, pH 8.0)

A primer panel may also be included.

Additional materials that may be used with any of these kits may include: Indexed 2nd PCR primers (e.g., New England BioLab, NEBNext® Multiplex Oligos for Illumina®, Dual-Indexed Primers Set 1, #E7600S; Single-Indexed Primers #E7335, #E7500, #E7710, #E7730); a thermal cycler; a 96-well plate or thin-wall PCR strip tubes with attached caps, adhesive film for sealing 96-well plate (or equivalent); an Agencourt AMPure® XP (Beckman Coulter, A63880, or A63881) or other similar Magnetic Beads (hereafter all referred as Magnetic Beads) for DNA purification; a DynaMag™-96 Side (Thermo Fisher Scientific, 12331D) or other similar magnet for 96-well plate or 8/12-well strip tubes; Absolute ethanol; Nuclease-free water; Pipettors and low-retention filtered pipette tips; a mini-centrifuge, 96-well plate centrifuge; and optionally a Qubit® 3.0 Fluorometer and dsDNA HS (high sensitivity) Assay Kit (or equivalent) and an Agilent® 2100 BioAnalyzer® Instrument and Agilent® High Sensitivity DNA Kit (or equivalent). A sequencing instrument (e.g., Illumina® HiSeq Series, NextSeq Series, MiSeq, MiniSeq, etc.) may be used.

These kits and panels described herein may be used together to amplify target regions of DNA using multiplex PCR. The amplification products from multiplex PCR (including amplicons and nonspecific products) may be purified and treated with the Digestion Reagent to degrade the primers and nonspecific PCR products. The amplicons may be further purified and re-amplified with primers containing indexes to form a DNA library. When multiple libraries are made and each library may be attached with a unique index, these libraries may be combined (pooled) in a variety of ways before being sequenced on (e.g.) Illumina instruments. Combining libraries maximizes the usage of flow-cell while minimizing cost and labor.

Before sequencing, the final library (either a single library or a pool of libraries each with a unique index) may be quantified by qPCR, or by a method compatible with Illumina sequencing instruments.

Any of these kits panels may be ideally suited for constructing targeted libraries from genomic DNA, DNA from FFPE tissue sections, cell-free DNA (cfDNA), and cDNA derived from RNA by reverse transcription. These targeted libraries are intended for use in Next-Generation Sequencing in detecting nucleotide sequence information related to various cancers, inherited diseases, infections, etc.

Figure 25:
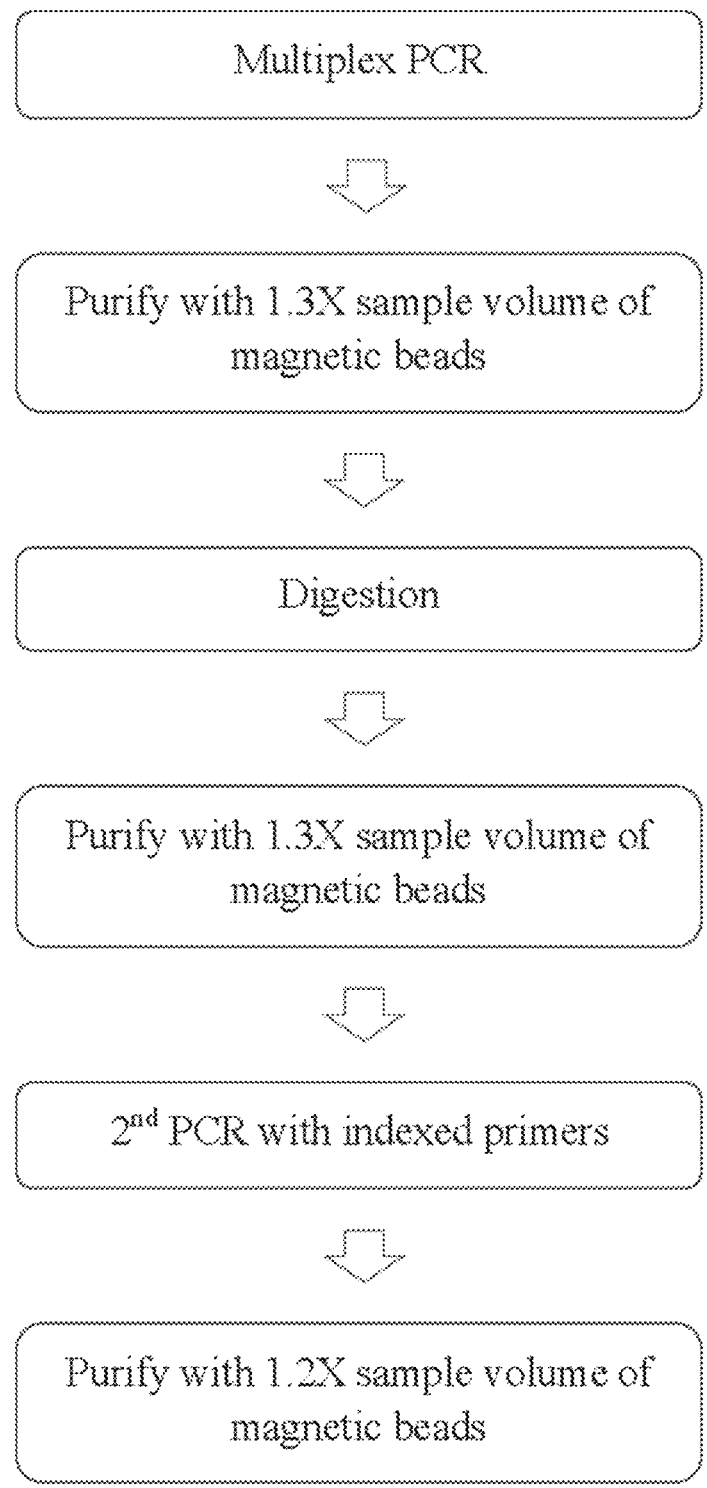
FIG. 25 is an example of a process flow diagram that may be used with a method or apparatus (e.g., kit) as described herein.

FIG. 25 shows one example of a work flow for use with any of the kits described herein. Below is an example of one method of using a kit as described herein.

Detailed Protocol

Section One, Input DNA Requirements.

Approximately 0.1-40 ng of human genomic DNA (30-12000 cells) from normal or FFPE tissue, or circulating cell-free DNA (cfDNA) can be used for each multiplex PCR reaction. 10 ng of human genomic DNA (3000 cells) is recommended for detection of somatic variants with 1% frequency. When DNA quality is low or unknown (such as DNA from FFPE tissues), higher DNA input usually produces better library quality and lower Limit of Detection. For germline genotyping assays, as low as 0.1 ng of high-quality genomic DNA may be used. We recommend the Qubit™ dsDNA HS Assay Kit (Thermo Fisher, Cat. No. Q32851 or Q32854) for measuring DNA concentration. UV spectrophotometry methods (e.g. using a NanoDrop™) are not recommended. The maximum volume of template DNA per reaction is 6 µl (for use with 5× concentrated primer pools) or 3 µl (for use with 2× concentrated primer pools).

Any of the panels described herein may be supplied as either 2× or 5× concentrated primer pools. Some panels are supplied as multiple primer pools. For these panels, an individual multiplex PCR reaction is required for each primer pool. It is a good practice to pre-warm thermal cycles, pre-warm a water bath or heat block to 37° C., and plan assigning indexes or index combinations to specific samples before starting the following steps.

Section Two, Amplify DNA Targets.

Step 1. Using thin-wall PCR strip tubes (or 96-well PCR plate for multiple samples), add the components in the following order on ice or a cold block. Note: It may be necessary to prepare a master mix excluding DNA samples for multiple reactions. In this case, add DNA samples individually at last to minimize cross-contamination.

| For 5X Primer Pool: | |
| --- | --- |
| Nuclease-free water | 6 – X µl |
| 5X mPCR Mix | 2 µl |
| 5X Primer Pool | 2 µl |
| DNA Sample | X µl |
| Total: | 10 µl |

| For 2X Primer Pool: | |
| --- | --- |
| Nuclease-free water | 3 – X µl |
| 5X mPCR Mix | 2 µl |
| 5X Primer Pool | 5 µl |
| DNA Sample | X µl |
| Total: | 10 µl |

5×mPCR mix and primer pools are viscous. Pipet slowly and rinse tips when handling these reagents. Mix the master mix by vortexing vigorously for 5 seconds, followed by brief spin.

Step 2. Close the cap of the strip tubes or seal the 96-well plate with adhesive film, spin briefly to bring down the liquid, mix by vortexing vigorously for 5 seconds, and spin down to collect droplets.

Section Three, Thermal Cycling Conditions.

Load the tubes or plate in the thermal cycler, and run the following PCR program to amplify target DNA regions.

| Step | ° C. | Time |
| --- | --- | --- |
| Pre-heat | 95 | 10 min |
| 10 Cycles | 98 | 15 sec |
|  | 60 | 5/8/16 min* |
| Hold | 10 | ∞ |

*5 min for 7-2000, 8 min for 2001-5000, 16 min for 5001-24000 pairs of primers per reaction.

Section Four, Purify the Amplicons.

Bring Magnetic Beads to room temperature and vortex thoroughly to disperse the beads before use. Pipette slowly. Use freshly prepared 70% ethanol.

Step 1. Spin the tubes or 96-well plate for 2 seconds. Open the tubes or carefully remove the adhesive film from the 96-well plate. For panels consisting of one primer pool, add 10 µl TE buffer to each sample. For panels consisting of multiple primer pools, combine the 10 µl multiplex PCR reactions for each sample. The total volume of each sample is approximately:

| Number of primer pools | Total volume of combined sample |
|---|---|
| 1 | (Add 10 μl of TE buffer) 20 μl |
| 2 | 20 μl |
| 3 | 30 μl |
| 4 | 40 μl |

Step 2. Vortex Magnetic Beads suspension vigorously for 5 seconds. Add 1.3× sample volume of Magnetic Beads suspension to each sample. For example, for 20 μl sample volume, add 26 μl of Magnetic Beads suspension to each sample. Close the caps or seal the 96 well plate with adhesive film, vortex vigorously for 5 seconds to thoroughly mix the mixture.

Step 3. Incubate the mixture for 5 minutes at room temperature.

Step 4. Spin the tubes or 96-well plate for 2 seconds. Place the tubes or plate on a magnetic rack and incubate for 2 minutes or until solution clears. The beads will be drawn onto one side of the wall. While keeping the tubes or 96-well plate on the magnet, carefully pipette to remove and discard the supernatant without touching the beads.

Step 5. Add 180 μl of freshly prepared 70% ethanol to each tube/well. Take out the tubes or plate from the magnet, place the clear side of the tubes against the magnet to move the beads from one side of the tube to the other side (no need to vortex), then pipette to remove and discard the supernatant without disturbing the beads.

Step 6. Repeat step 4.

Step 7. After the second wash, carefully pipette to remove as much as possible the residual droplets left behind in the tubes (it may require brief spin for 2 seconds to bring down all droplets and magnet the tubes again). Keeping the plate in the magnet, air-dry the beads at room temperature for 5 minutes. Do not overdry. Note: Residual ethanol inhibits the following reaction. If necessary, briefly spin the tubes or plate. While placing the tubes or plate on magnet, remove residual droplet prior to air-drying the beads.

Step 8. Add 10 μl TE buffer to each tube. Briefly spin and vortex to resuspend the beads. The DNA will be immediately released from the beads (no need to remove the beads). Brief spin. Go to the next step.

Section Five, Digest Nonspecific Products.

Set a water bath to 37° C., or pre warm a thermal cycler to 37° C. before the following step.

Step 1. Open the tubes or carefully remove the 96-well plate seal, add the following reagents to each amplified sample (the beads in the mixture do not affect the reaction).

| Add to the Bead Suspension: | |
|---|---|
| Nuclease-free Water | 6 μl |
| 10 X Digestion Buffer | 2 μl |
| Digestion Reagent | 2 μl |
| Total: | 10 μl |

Step 2. Close the tubes or seal the plate with adhesive film, vortex thoroughly, and spin down to collect droplets.

Step 3. Incubate at 37° C. for 10 minutes (Do NOT incubate longer than 10 minutes).

Step 4. Immediately add 2 μl Stop Buffer to each tube, mix by brief spin and vortexing. Spin to bring the liquid to the bottom. The volume of each sample is approximately 22 μl.

Section Six, Purify the Amplicons.

Step 1. Vortex to resuspend the Magnetic Beads suspension. Add 29 μl (1.3× sample volume) of Magnetic Beads to each multiplex PCR reaction. The methods described in Section Four Step 2 to 7 is used again in this step. The only difference is that 29 μl of Magnetic Beads is used. Please refer to Section 9.4 Step 2 to 7 to purify the amplicons.

Step 2. After purification, Add 10 μl TE buffer to each tube. Briefly spin, vortex and spin (no need to remove the beads). Go to the next step.

Section Seven, Amplify and Add Index

Step 1. Thaw NEB Universal Primer and Index Primers, vortex briefly for 2 seconds, spin briefly for 2 seconds to collect the droplets. Add the following reagents to the above beads-DNA suspension:

| Add to the Bead Suspension: | |
|---|---|
| Nuclease-free Water | 18 μl |
| 5X $2^{nd}$ PCR Mix | 8 μl |
| Total: | 26 μl |

Note:
It may be necessary to prepare a master mix of above for multiple reactions.

Then add index primers carefully to the above beads-DNA suspension. Be cautious to minimize cross-contamination of index primers:

| Add to Each Specific Sample: | |
|---|---|
| NEB Universal or i5 Index Primer (10 μM) | 2 μl |
| i7 Index Primer (10 μM) | 2 μl |

Note:
New England BioLab's NEBNext ® Multiplex Oligos include 48 single-indexed primers (#E7335, #E7500, #E7710, #E7730) and Dual-Index Primers (#E7600S) for 96 index combinations.
It is necessary to plan beforehand to assign a specific index or index combination to each specific sample.

Step 2. Close the strip tubes or seal the plate with adhesive film, vortex thoroughly, and spin down to collect droplets.

Step 3. Load the tubes or plate in the thermal cycler, and run the following PCR program.

| Step | ° C. | Time |
|---|---|---|
| Pre-heat | 95 | 10 min |
| Cycle number in chart below | 98 | 15 sec |
| | 60 | 75 sec |
| Hold | 10 | ∞ |

| Number of Total Amplicons | 10 ng of high quality gDNA | 10 ng of low quality DNA (cfDNA or FFPE DNA) |
|---|---|---|
| 7-100 | 13 | 14 |
| 101-200 | 11 | 12 |
| 201-500 | 10 | 11 |
| 501-1000 | 9 | 10 |
| 1001-2000 | 8 | 9 |
| 2001-5000 | 7 | 8 |
| 5001-12000 | 6 | 7 |
| 12001-24000 | 5 | 6 |

Note:
The optimal PCR cycler number may need fine-tuning for each specific primer panel. Generally, add 3 cycles for 1 ng of DNA, 6 cycles for 0.1 ng of DNA; reduce 1 cycle for 20 ng of DNA, 2 cycles for 40 ng of DNA.
Stop point: PCR products may be stored at 10° C. overnight. For longer periods, store at −20° C.

Section Eight, Purify the Amplicons:

Step 1. Vortex to resuspend the Magnetic Beads suspension. Add 48 µl (1.2× sample volume) of Magnetic Beads to each multiplex PCR reaction. The same methods described in Section Four, steps 2 to 7 is used again in this step. The only difference is that 48 µl of Magnetic Beads is used. Please refer to Section 9.4 Step 2 to 7 to purify the amplicons.

Step 2. Add 10 µl TE buffer to each tube. Briefly spin and vortex to resuspend the beads to elute DNA from beads. Spin briefly to bring the liquid to the bottom. The library is finished. The library can be stored with beads at −20° C. (remember to magnet the beads behind when taking library out for QC and sequencing).

Step 3. (Optional) Measure the concentration of the library by Qubit® 3.0 Fluorometer and dsDNA HS (high sensitivity) Assay Kit. Check library quality and concentration with Agilent® 2100 BioAnalyzer® Instrument and Agilent® High Sensitivity DNA Kit.

Figure 26:
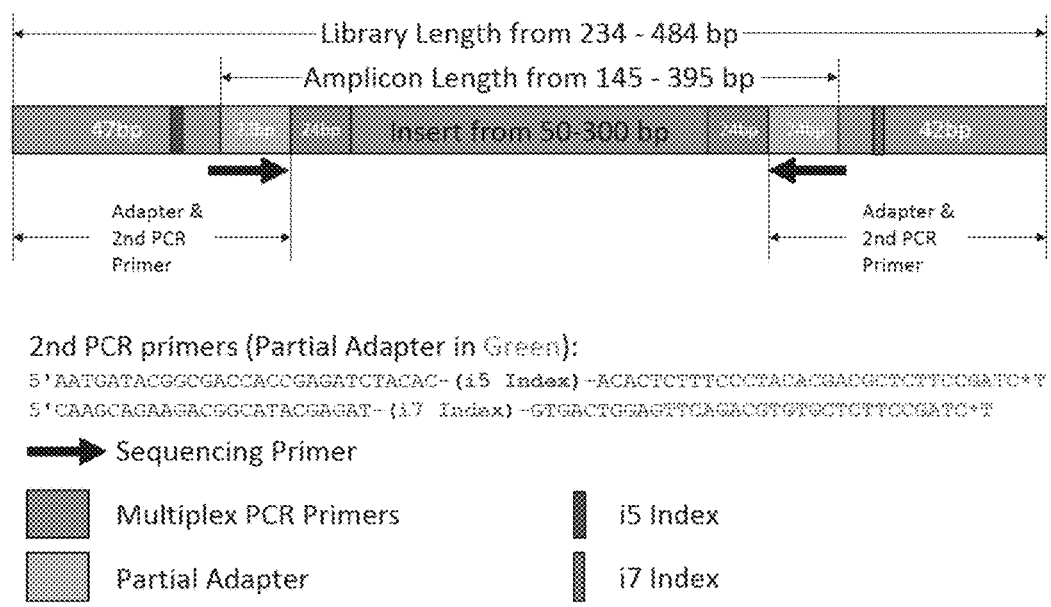
FIG. 26 is an example of a library structure (e.g., dual indexed) that may be used with any of the methods and apparatuses (e.g., kits) described herein.

FIG. 26 illustrates one example of a library structure (dual-indexed) that may be used with any of the apparatuses (including kits) and methods described herein.

Examples of single-indexed primers may include i7 Index Primer (for position of index, please refer to New England BioLab's NEBNext® Multiplex Oligos #E7335, #E7500, #E7710, #E7730 for index bases). Examples of dual-indexed primers may include i5 Index Primer (for position of index, please refer to New England BioLab's NEBNext® Multiplex Oligos #E7600S for index bases) and i7 Index Primer (for position of index refer to New England BioLab's NEBNext® Multiplex Oligos #E7600S for index bases).

Example 22

Figures 27, 29:
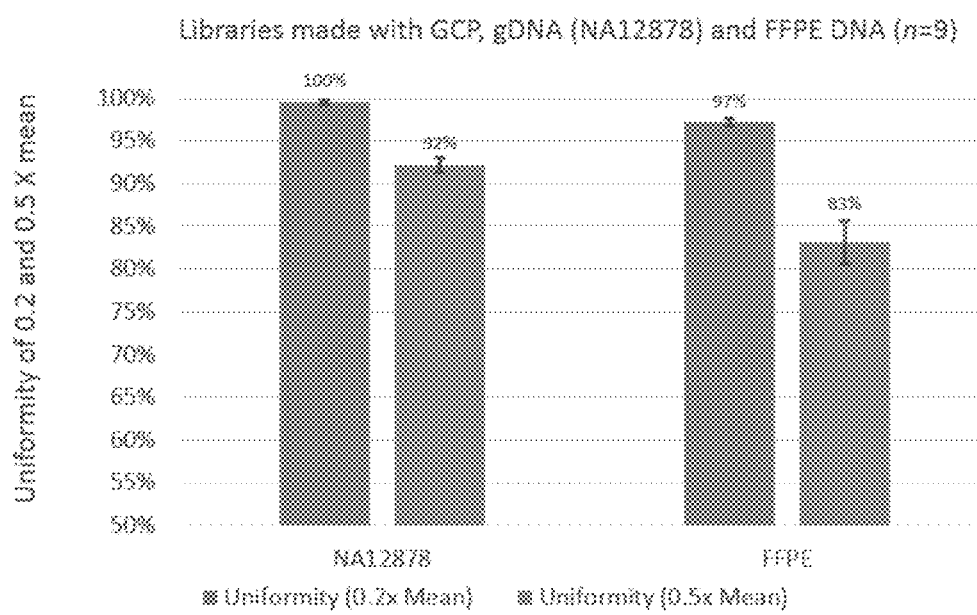
FIG. 27 is an example of the genes covered by the Paragon Genomics GCP panel.
FIG. 29 illustrates the uniformity of libraries made with GCP and genomic DNA and FFPE DNA.
Figure 28A:
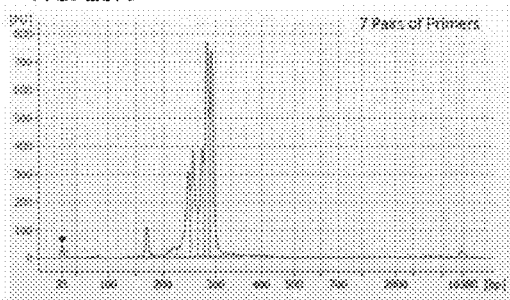
FIGS. 28A-28H illustrate the libraries and the sequencing results shown as read count per amplicon against GC content.
Figure 28B:
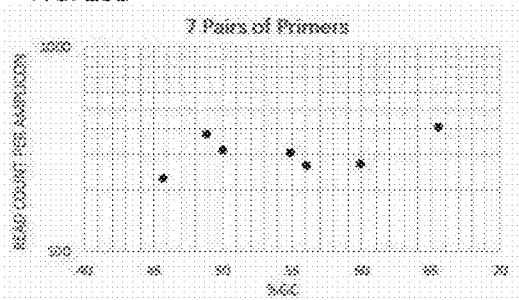
Figure 28C:
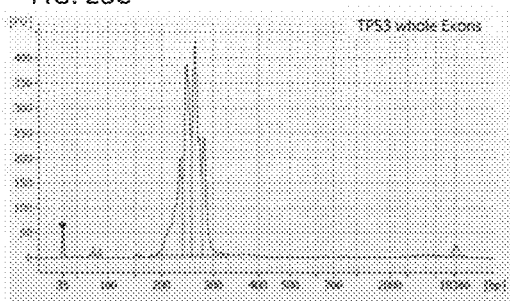
Figure 28D:
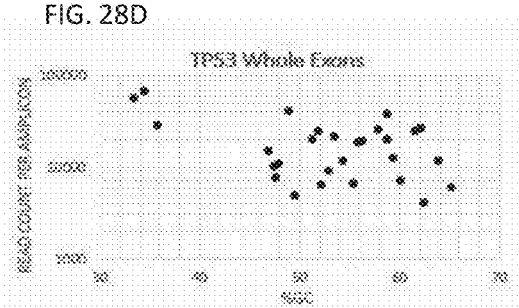
Figure 28E:
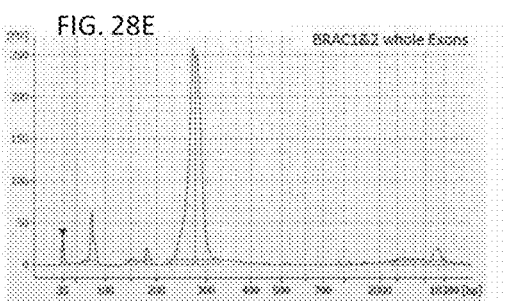
Figure 28F:
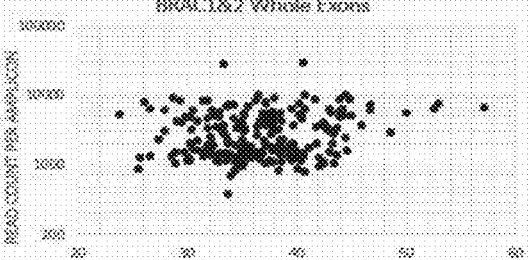
Figure 28G:
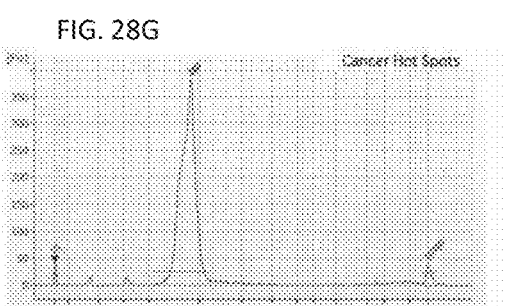
Figure 28H:
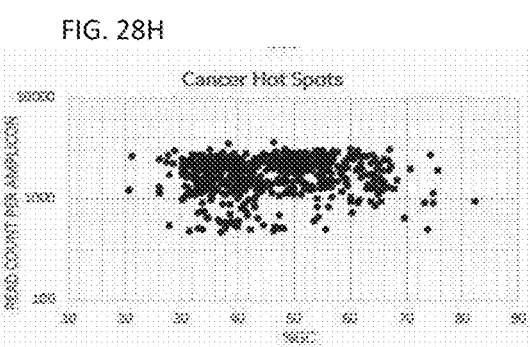

Libraries were made by using the exemplary kit and protocol described in EXAMPLE 21. These libraries were made with genomic DNA NA12878 (Coriell Institute) and multiplex PCR primer panels of TP53, BRAC1&2, and a generic cancer panel from Paragon Genomics Inc. The TP53 panel, which has two primer pools and a total of 29 pairs of primers, covers all of the exons of genes TP53, while BRAC1&2, two primer pools and 219 pairs of primers in total, covered all of the exons of gene BRAC1 and BRAC2. The generic cancer panel covers a selected group of cancer hotpots from 65 cancer related genes (see. FIG. 27). It has 601 pairs of primers in one primer pool. In addition, 7 pairs of primers were randomly selected from the generic cancer panel, and a library with NA12878 was made. These libraries were assayed by Agilent's High Sensitivity DNA Kits and BioAnalyzer 2100. FIG. 28A shows the Bioanalyzer 2100 trace of the 7-amplicon library, demonstrating the successful amplification of these 7 amplicons with minimal non-specific amplification products. Similarly, FIG. 28C demonstrate the successful making of TP53 library, FIG. 28E, the BRAC1 &2 library, and FIG. 28G, the generic cancer library. These libraries were sequenced by using Illumina's MiSeq sequencing platform. The times of each amplicon that has been sequenced (the reads) were analyzed, and the number against the GC content of each amplicon was plotted. The results are show in FIG. 28B for the 7-amplicon library; FIG. 28D, TP53 library; FIG. 28F, BRAC1&2 library; and FIG. 28H, the generic cancer library. These results demonstrate that no GC bias were found in the libraries, and the difference between the lowest and the highest reads are roughly 10 times.

Example 23

Further libraries were made with generic cancer panel and DNA purified from FFPE samples (BioChain) by using the kit and protocol described in EXAMPLE 21. These libraries were sequenced and analyzed the uniformity at 0.2× and 0.5× mean of reads. FIG. 29 illustrates that the uniformity at 0.2× mean is 100% and 97% for genomic DNA NA12878 and FFPE DNA, respectively; while the uniformity at 0.5× mean is 92% and 83%, respectively.

Example 24

Figure 30:
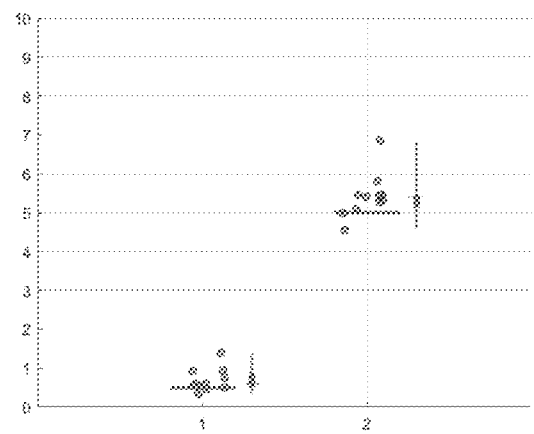
FIG. 30 illustrates the allele frequencies detected with GCP libraries made with 0.5% NA12878 in NA18507 and 5% NA12878 in NA18507.

In this example, NA12878 was spiked into genomic DNA NA18507 (Coriell Institute) at 0.5% and 5%, respectively. Since both sequences of NA12878 and NA18506 are known, we can sequence the libraries made from these DNA samples and examine if the alleles of NA12878 could be recovered at expected number and percentage (frequency), thus testing the limit of detection. These libraries were made with the generic cancer panel by using the kit and protocol described in EXAMPLE 21. The number and frequency of the NA12878 alleles covered by the generic cancer panel are depicted in FIG. 30. It shows that the number and frequency of the NA12878 alleles are recovered as expected.

Figure 31:
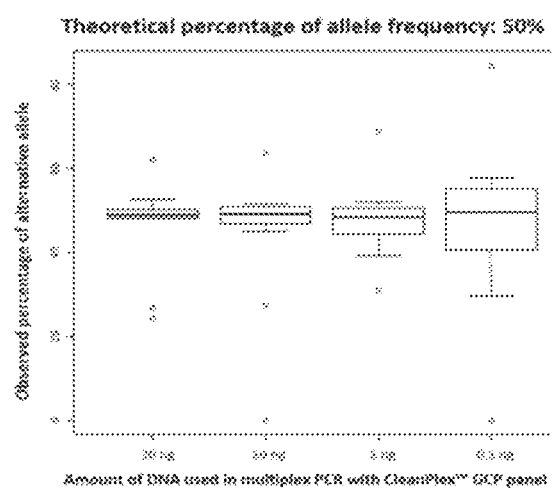
FIG. 31 illustrates the distribution of 50% allele frequencies detected with GCP libraries made with various amounts of NA12878.

We further made libraries with 0.1, 1, 10 and 20 ng of NA12878 with the generic cancer panel by using the kit and protocol described in EXAMPLE 21. We sequenced these libraries and analyzed the alleles that are expected to be 50% in allele frequency. As shown in FIG. 31, with less and less input DNA for library making, the variation at 50% allele frequency becomes larger and larger. However, it appears to be acceptable that 0.1 ng of high quality genomic DNA could be used to make libraries for massive high-throughput sequencing.

To demonstrate the accuracy of the variant calling, we further made libraries with generic cancer panel and reference cfDNA from Horizon Discovery (HD780) by using the kit and protocol described in EXAMPLE 21. This reference DNA has defined allele frequencies at specified gene loci. FIG. 32 illustrates that correct results were obtained.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of reducing non-specific amplification products formed between primers and between primers and template in a template-dependent primer extension reaction, the method comprising:

amplifying a plurality of target nucleic acids using a plurality of pairs of target-specific primers that are in a same reaction mixture, wherein said amplifying generates a plurality of target-specific amplification products and a plurality of non-specific amplification products formed between primers, between primers and template, or both;

introducing a resolvase that recognizes an aberrant DNA structure and cleaving said non-specific amplification products with the resolvase to generate a plurality of cleaved non-specific amplification products while maintaining a substantial proportion of said plurality of target-specific amplification products, wherein the resolvase recognizes an aberrant DNA structure comprising at least one of Holliday structures or junctions, branched DNAs, Y-structures, cruciforms, hetereoduplex loops, bulky adducts, single-stranded overhangs, DNA mismatches, or non-perfectly-matched DNAs.

2. The method of claim 1, further comprising degrading the cleaved non-specific amplification products and primers by an exonuclease, multiple exonucleases, or a combination of exonucleases and nucleases.

3. The method of claim 1, further comprising degrading the cleaved non-specific amplification products and primers by an exonuclease, multiple exonucleases, or a combination of exonucleases and nucleases, selected from the group comprising: S1 nuclease, P1 nuclease, mung bean nuclease, lambda exonuclease, exonuclease I, exonuclease VII, exonuclease T, RecJ, RecJf.

4. The method of claim 1, further comprising removing the cleaved non-specific amplification products, leaving the substantial proportion of said plurality of target-specific amplification products.

5. The method of claim 1, further comprising re-amplifying the target-specific amplification products by polymerase chain reaction.

6. The method of claim 1, further comprising analyzing the target-specific amplification products by length, melting curve, hybridization to a probe or probes, or nucleotide sequence by high-throughput sequencing.

7. The method of claim 1, wherein amplifying comprises performing a multiplex polymerase chain reaction (PCR).

8. The method of claim 1, wherein said target nucleic acids comprises DNA or RNA.

9. The method of claim 1, wherein said target nucleic acids is genomic DNA, cDNA, DNA purified from Formalin-fixed, Paraffin-embedded (FFPE) tissue samples (FFPE DNA), cell-free DNA (cfDNA) or Circulating tumor DNA (ctDNA).

10. The method of claim 1, wherein the length of the target-specific primers is from 16-100 nucleotides.

11. The method of claim 1, wherein said target-specific primers comprise at least 7 pairs of target-specific primers.

12. The method of claim 1, wherein said target-specific primers comprise between 7 pairs of target-specific primers and 1,000,000 pairs of target-specific primers.

13. The method of claim 1, wherein the target-specific primers comprise one or more of: unmodified oligonucleotides with no chemical modifications of nucleotides and/or chemical bonds and no degenerated bases; or modified oligonucleotides with one or more of: chemical modifications of nucleotides or chemical bonds, and degenerated bases.

14. The method of claim 1, wherein one or more of the target-specific primers in each pair of target-specific primers contains a barcode identification sequence.

15. The method of claim 1, wherein both target-specific primers in each pair of target-specific primers contain a stretch of nucleotide sequences that are compliment to parts of PCR primers used for re-amplification of the target-specific amplification products.

16. The method of claim 1, wherein cleaving said non-specific amplification products with the resolvase comprises exposing the non-specific amplification products and the plurality of target-specific amplification products to between about 0.2 U and 1000 U of resolvase for between 0.5 minutes and 60 minutes at between 16° C. and 37° C.

17. The method of claim 1, wherein the substantial proportion of said plurality of target-specific amplification products comprises greater than 50% of the plurality of target-specific amplification products.

18. The method of claim 1, wherein the resolvase is one of: a Holliday junction resolvase, a T7 endonuclease I, a T4 endonuclease VII, a homolog of T7 endonuclease I, a homolog of T4 endonuclease VII, a flap endonuclease (FEN), a homolog of FEN, an endonuclease V, a homologs of endonuclease V, an *E. coli* endonuclease V, a *Thermotoga maritima* endonuclease V, a structure-specific endonuclease; a mismatch repair enzyme, a nuclease S1, a nuclease P1, a mung bean nuclease, a CEL nuclease, an endonuclease CEL I, transcription factor SP1, and combinations, fusions, or mutations thereof.

19. A method of reducing non-specific amplification products formed between primers and between primers and template in a template-dependent primer extension reaction, the method comprising:
amplifying a plurality of target nucleic acids using a plurality of pairs of target-specific primers that are in a same reaction mixture, wherein said amplifying generates a plurality of target-specific amplification products and a plurality of non-specific amplification products formed between primers, between primers and template, or both;
introducing a resolvase that recognizes an aberrant DNA structure and cleaving said non-specific amplification products with the resolvase to generate a plurality of cleaved non-specific amplification products while maintaining a substantial proportion of said plurality of target-specific amplification products, wherein the resolvase is one of: a Holliday junction resolvase, a T7 endonuclease I, a T4 endonuclease VII, a homolog of T7 endonuclease I, a homolog of T4 endonuclease VII, a flap endonuclease (FEN), a homolog of FEN, an endonuclease V, a homologs of endonuclease V, an *E. coli* endonuclease V, a *Thermotoga maritima* endonuclease V, a structure-specific endonuclease; a mismatch repair enzyme, a nuclease S1, a nuclease P1, a mung bean nuclease, a CEL nuclease, an endonuclease CEL I, transcription factor SP1, and combinations, fusions, or mutations thereof.

20. A method of reducing non-specific amplification products formed between primers and between primers and template in a template-dependent primer extension reaction, the method comprising:
amplifying a plurality of target nucleic acids using a plurality of pairs of target-specific primers that are in a same reaction mixture, wherein said amplifying generates a plurality of target-specific amplification products and a plurality of non-specific amplification products formed between primers, between primers and template, or both;
introducing a resolvase that recognizes an aberrant DNA structure and cleaving said non-specific amplification products with the resolvase to generate a plurality of cleaved non-specific amplification products while maintaining a substantial proportion of said plurality of target-specific amplification products, wherein the resolvase is one of: a Holliday junction resolvase, a T7 endonuclease I, a T4 endonuclease VII, a homolog of T7 endonuclease I, a homolog of T4 endonuclease VII, a flap endonuclease (FEN), a homolog of FEN, an endonuclease V, a homologs of endonuclease V, an *E. coli* endonuclease V, a *Thermotoga maritima* endonuclease V, a structure-specific endonuclease; a mismatch repair enzyme, a nuclease S1, a nuclease P1, a mung bean nuclease, a CEL nuclease, an endonuclease CEL I, transcription factor SP1, and combinations, fusions, or mutations thereof;

removing the cleaved non-specific amplification products, leaving the substantial proportion of said plurality of target-specific amplification products; and re-amplifying the plurality of target-specific amplification products.

* * * * *

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cctacacgac gctcttccga tct                                             23

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ttcagacgtg tgctcttccg atct                                            24

<210> SEQ ID NO 3
<211> LENGTH: 58
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (57)..(58)
<223> OTHER INFORMATION: Phosphorothioate linkage

<400> SEQUENCE: 3
aatgatacgg cgaccaccga gatctacact ctttccctac acgacgctct tccgatct          58

<210> SEQ ID NO 4
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate
<220> FEATURE:
<221> NAME/KEY: misc_feature
<222> LOCATION: (58)..(63)
<223> OTHER INFORMATION: Phosphorothioate linkage

<400> SEQUENCE: 4
gatcggaaga gcacacgtct gaactccagt cacatcacga tctcgtatgc cgtcttctgc          60
ttg                                                                         63

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatgatacgg cgaccaccga                                                       20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caagcagaag acggcatacg agat                                                  24

<210> SEQ ID NO 7
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatgatacgg cgaccaccga gatctacact ctttccctac acgacgctct tccgatct          58

<210> SEQ ID NO 8
<211> LENGTH: 63
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 8
gatcggaaga gcacacgtct gaactccagt cacatcacga tctcgtatgc cgtcttctgc      60
ttg                                                                    63

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aatgatacgg cgaccaccga gatctacac                                        29

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (32)..(33)
<223> OTHER INFORMATION: Phosphorothioate linkage

<400> SEQUENCE: 10
acactctttc cctacacgac gctcttccga tct                                   33

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caagcagaag acggcatacg agat                                             24

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (33)..(34)
<223> OTHER INFORMATION: Phosphorothioate linkage

<400> SEQUENCE: 12
gtgactggag ttcagacgtg tgctcttccg atct                                  34
```